(12) United States Patent
Nam et al.

(10) Patent No.: US 12,307,346 B2
(45) Date of Patent: May 20, 2025

(54) LIPID NANOTABLET

(71) Applicant: Seoul National University R&DB Foundation, Seoul (KR)

(72) Inventors: Jwa Min Nam, Seoul (KR); Sungi Kim, Seoul (KR); Jinyoung Seo, Seoul (KR); Ha Hyung Park, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 213 days.

(21) Appl. No.: 17/058,981

(22) PCT Filed: May 23, 2019

(86) PCT No.: PCT/KR2019/006215
§ 371 (c)(1),
(2) Date: Nov. 25, 2020

(87) PCT Pub. No.: WO2019/231173
PCT Pub. Date: Dec. 5, 2019

(65) Prior Publication Data
US 2024/0256822 A1 Aug. 1, 2024

(30) Foreign Application Priority Data
May 29, 2018 (KR) .......................... 10-2018-0061345

(51) Int. Cl.
*G06N 3/00* (2023.01)
*C12Q 1/6816* (2018.01)
*G06N 3/123* (2023.01)

(52) U.S. Cl.
CPC .......... *G06N 3/002* (2013.01); *C12Q 1/6816* (2013.01); *G06N 3/123* (2013.01)

(58) Field of Classification Search
CPC ...... G06N 3/002; G06N 3/123; C12Q 1/6816; C12Q 2563/137; C12Q 2565/519
See application file for complete search history.

(56) References Cited

U.S. PATENT DOCUMENTS

2004/0002089 A1    1/2004  Dubertret et al.
2004/0023304 A1*   2/2004  Stefan ................... G06N 3/002
                                                       435/7.1
(Continued)

FOREIGN PATENT DOCUMENTS

CN        102586400 A        7/2012
CN        106461640 A        2/2017
(Continued)

OTHER PUBLICATIONS

International Search Report—PCT/KR2019/006215 dated Sep. 4, 2019.
(Continued)

*Primary Examiner* — Jesse P Frumkin
(74) *Attorney, Agent, or Firm* — CANTOR COLBURN LLP

(57) ABSTRACT

A lipid nanotablet according to the present disclosure includes: a supported lipid bilayer having a plurality of nanoparticles integrated in nanoparticle units; an immobile nano-receptor including at least one first surface molecule from among the plurality of nanoparticles and coupled to the surface of the nano-receptor, and a mobile nano-floater including at least one second surface molecule from among the plurality of nanoparticles coupled to the surface of the nano-floater. Interaction between the nano-receptor and the nano-floater is controlled according to the result of a reaction to an input by the at least one first surface molecule and the at least one second surface molecule, and the lipid nanotablet provides a logic result on the basis of the interaction.

20 Claims, 68 Drawing Sheets
Specification includes a Sequence Listing.

(56) References Cited

U.S. PATENT DOCUMENTS

| | | | |
|---|---|---|---|
| 2004/0161798 | A1 | 8/2004 | Kodadek |
| 2014/0106469 | A1 | 4/2014 | Wu et al. |
| 2015/0346198 | A1 | 12/2015 | Naumann et al. |
| 2017/0115286 | A1* | 4/2017 | Nam .................... C12Q 1/6816 |
| 2017/0233748 | A1 | 8/2017 | Boyden et al. |

FOREIGN PATENT DOCUMENTS

| | | |
|---|---|---|
| DE | 102013106380 A1 | 12/2013 |
| KR | 101492047 | 2/2015 |
| KR | 1020150082729 | 7/2015 |
| KR | 101725369 | 4/2017 |
| WO | 0113432 A1 | 2/2001 |

OTHER PUBLICATIONS

Maxim P. Nikitin, et al., "Biocomputing based on particle disassembly", Nature Nanotechnology, (Aug. 17, 2014), vol. 9, pp. 716-721.

Najmeh Nozhat, et al., "All-optical XOR and NAND logic gates based on plasmonic nanoparticles", Optics Communications, (Jun. 1, 2017), vol. 392, pp. 208-213.

Written Opinion—PCT/KR2019/006215 dated Sep. 4, 2019.

Chinese Office Action—Chinese Patent Application No. 201980036331.1 dated Aug. 28, 2023.

Self-assembled DNA Chain ReplacementMolecular Logic Calculation ModelScience China Press, 2012 vol. 57 Issue 31:2909~2915.

European Search Report—European Patent Application No. 19810936.5 dated Mar. 21, 2022.

Ilya L. Sokolov, et al., "Smart materials on the way to theranostic nanorobots: Molecular machines and nanomotors, advanced biosensors, and intelligent vehicles for drug delivery", Biochimica et Biophysica Acta, Elsevier, vol. 1861, No. 6, (Jan. 24, 2017), pp. 1530-1544.

Kevin L. Hartman, et al., "Supported lipid bilayers as dynamic plattorms for tethered particles", Nanoscale, vol. 7, No. 1, (Jan. 1, 2015), pp. 66-76.

Scott G. Harroun, et al., "Programmable DNA switches and their applications", Nanoscale, vol. 10, No. 10, (Jan. 1, 2018), pp. 4607-4641.

* cited by examiner

FIG. 17F

|  | Reaction type | |
|---|---|---|
|  | Assembly | Disassembly |
| Serial connection | AND | OR |
| Parallel connection | OR | AND |

# LIPID NANOTABLET

TECHNICAL FIELD

The present disclosure relates to computation using nanoparticles. Specifically, it relates to nanoparticle computation using bioinformation as an input.

BACKGROUND ART

Across many length scales, matters have been merged with computation, from micro-sized droplets and microparticles to molecular machines and biomolecules, such as enzymes and nucleic acids. However, implementing complex computation in nanoscale objects, especially in nanoparticles, remains unexplored, despite a wide range of potential applications that would benefit from controlling their potentially useful plasmonic, photonic, catalytic, and material properties.

A common approach to using nanoparticles as substrates for computation is functionalizing the "core" structures with stimuli-responsive surface ligands. A group of surface-modified nanoparticles can then carry out elementary logic operations, responding to various chemical and physical inputs, and ideally, individual nanoparticles should be used as modular "nano-parts", and desired computation should be implemented in a plug-and-play manner. However, such an existing method has been limited to installing few logic computations that are applicable to controlling only simple outputs, such as aggregation/dispersion of particles and release of surface molecules. This limitation is because of the difficulties in modular wiring of multiple logic gates in the solution phase, where inputs, logic gates, and outputs all diffuse uncontrollably in the three-dimensional space.

In particular, the following constraints have imposed limitations on computing with nanoparticles.

First, logic-embedded particles are irreversibly altered after one operation and are indiscriminately mixed with unreacted inputs in one bulk solution. The lack of compartmentalization prevents the implementation of more than one computational task per test tube.

Second, it is difficult to control or characterize structure changes, dynamic interactions, and output signals of freely diffusing individual particles in the 3D space. In most cases, only an averaged signal is obtained as the final readout, in which particle-by-particle responses of the computation are averaged.

These constraints, thus, impose limitations on employing nanoparticles as modular and composable parts that can be reconfigured to implement a desired computation in a "plug-and-play" manner.

DISCLOSURE

Technical Problem

In order to construct a complex and reliable nanoparticle circuit, it is necessary to move beyond a method that once relies on a solution step to a scalable integrated platform with in-situ readout and control functions. In addition, the desired nanoparticle circuit should be systematically designed and constructed based on the digital design principle.

Technical Solution

Nanoparticle systems equipped with computing capability can achieve complex functions that are not attainable in a simple collection of individual nanoparticles. Such a "nanosystem" autonomously performs complex tasks in response to stimuli. Then, the nanosystem can be a system that can direct the flow of matter and information at a nanoscale.

Processing molecular information with nanoparticles allows for incorporating the rich and powerful functions of nanoparticles into algorithmic and autonomous controls on molecular computing processes. In the present disclosure, a platform, termed "lipid nanotablet", is provided to construct a widely applicable system that can create nanoparticle circuits. The lipid nanotablet is a technology that constructs nanoparticle logic gates and circuits at the level of a single particle in a two-dimensional lipid bilayer. Such a lipid bilayer-based nanoparticle computing platform (with computer system/software as a basis for use) is hereinafter referred to as a lipid nanotablet (LNT).

The lipid nanotablet uses lipid bilayers as a chemical/biological board, on which surface-modified nanoparticles are placed to enable the lipid bilayers to react with molecular information, to host nanoparticles, and employ them as units of computation. A single-nanoparticle logic gate senses molecular inputs and triggers particle assembly or disassembly. Through the present disclosure, a set of Boolean logic operations such as AND, OR, and NOT computations, fan-in/fan-out of logic gates, and a circuit such as a multiplexer can be provided. As described, implementation of nanoparticle circuit modules on the lipid nanotablet may open previously unknown opportunities in information-processing nanosystems.

A lipid nanotablet according one aspect of the present invention includes: a supported lipid bilayer to which a plurality of nanoparticles are integrated in nanoparticle units; an immobile nano-receptor that includes at least one first surface molecule tethered to a surface and is immobile among the plurality of nanoparticles; and a nano-floater that includes at least one second surface molecule tethered to a surface and is mobile among the plurality of nanoparticles, wherein an interaction between the nano-receptor and the nano-floater is controlled according to a reaction result of the at least one first surface molecule and the at least one second surface molecule with respect to inputs, and a logic result based on the interaction is provided.

The lipid nanotablet may include a YES gate that generates a logic result based on an assembly reaction in which the at least one first surface molecule and the at least one second surface molecule are combined by inputs and thus the nano-receptor and the nano-floater are tethered.

The input may include a DNA input, and the at least one first surface molecule and the at least second surface molecule respectively comprise surface DNA ligands, and the surface DNA ligand of the nano-receptor and the surface DNA ligand of the nano-floater may be hybridized in response to the DNA input.

The lipid nanotablet may include a YES gate that generates a logic result based on a disassembly reaction that removes the tethering between the nano-receptor and the nano-floater by inputs, while the nano-receptor and the nano-floater are tethered by combination of the at least one first surface molecule and the at least one second surface molecule.

The input may include a DNA input, and the DNA input may remove a DNA bond through a toehold-mediated strand displacement in pre-dimerization of the nano-receptor and the nano-floater tethered through the DNA bond.

The lipid nanotablet may include an AND gate that generates a logic result through tethering of the nano-receptor and the nano-floater by combinations of a first input to the at least one first surface molecule and a second input to the at least one second surface molecule.

The at least one first surface molecule and the at least one surface molecule may include conformation-switchable first and second DNA hairpins, and the first DNA hairpin may be opened by hybridization with the first input and thus a first binding domain is exposed, the second DNA hairpin may be opened by hybridization with the second input and thus a second binding domain is exposed, and the nano-receptor and the nano-floater may be tethered through hybridization of the first binding domain and the second binding domain.

The at least one first surface molecule may include third and fourth surface molecules, the at least one second surface molecule may include fifth and sixth surface molecules, and the lipid nanotablet may include an OR gate that generates a logic result from tethering of the nano-receptor and the nano-floater by at least one of a combination of a first input and the third and fifth surface molecules and a combination of a second input and the fourth and sixth surface molecules.

The third to sixth surface molecules may be DNA ligands and may include first to fourth binding domains, and the first input may be hybridized with the first and third binding domains and the second input may be hybridized with the second and third binding domains.

The at least one first surface molecule may include third and fourth surface molecules, the at least one second surface molecule may include fifth and sixth surface molecules, the third surface molecule and the fifth surface molecule may be combined, the fourth surface molecule and the sixth surface molecule are may be, and the third surface molecule and the fifth surface molecule are may be, the fourth surface molecule and the sixth surface molecule may be combined, and the lipid nanotablet may include an AND gate that generates a logic result by removing the combination of the third and fifth surface molecules and removing the combination of the fourth and sixth surface molecules First DNA binding between the third surface molecule and the fifth surface molecule and second DNA binding between the fourth surface molecule and the sixth surface molecule may expose a first toehold domain and a second toehold domain, the first toehold domain may be a recognition area of the first input, the first input may remove the first DNA binding through strand displacement, the second toehold domain may be a recognition area of the second input, and the second input may remove the second DNA binding through strand displacement.

The at least one first surface molecule and the at least one second surface molecule may be combined, and the lipid nanotablet may include an OR gate that generates a logic result by removing the at least one first surface molecule and the at least one second surface molecule by at least one of a first input and a second input.

The combination of the at least one first surface molecule and the at least one second surface molecule may be DNA binding, the DNA binding may include first and second toehold domains, and when the first toehold recruits the first input, the first input cleaves the DNA bonding through strand displacement with at least one first surface molecule or when the second toehold domain recruits the second input, the second input may cleave the DNA binding through strand displacement with the at least one second surface molecule.

Interaction between the nano-receptor and the nano-floater may be a first logic gate that is controlled by a first input and a second input, interaction between another one first nano-receptor and another one first nano-floater among the plurality of nanoparticles may be a second logic gate that is controlled by a third input and a fourth input, and the lipid nanotablet may include a third logic gate that generates a logic result based on a first logic result of the first logic gate and a second logic result of the second logic gate.

The nano-receptor and the nano-floater may be tethered by at least one of the first input and the second input, the tethering of the first nano-receptor and the first nano-floater may be disassembled by the third input and the fourth input, and the first logic output may be a logic OFF output of the third logic gate and the second logic output may be a logic ON output of the third logic gate.

The at least one first surface molecule may include third and fourth surface molecules, the at least one second surface molecule may include fifth and sixth surface molecules, and the lipid nanotablet may include an INHIBIT gate that generates a logic result by removing the combination between the third surface molecule and the fifth surface molecule.

The second input may combine the fourth surface molecule and the sixth surface molecule.

The first input may remove DNA bonding between the third surface molecule and the fifth surface molecule.

Interaction of the nano-receptor and the nano-floater may be controlled as third and fourth surface molecules tethered to the at least one first surface molecule and the surface of the nano-receptor and fifth and sixth surface molecules tethered to the at least one second surface molecule and the surface of the nano-floater interact with each other.

At least one of a first input and a second input may remove a combination between the at least one first surface molecule and the at least one second surface molecule, at least one of a third input and a fourth input may remove a combination between the third surface molecule and the fifth surface molecule, and, at least one of a fifth input and a sixth input may remove a combination between the fourth surface molecule and the sixth surface molecule.

At least one of a first input and a second input may remove a combination between the at least one first surface molecule and the at least one second surface molecule, a third input may form a combination between the third surface molecule and the fifth surface molecule, and a fourth input may form a combination between the fourth surface molecule and the sixth surface molecule.

A first input may remove a combination between the at least one first surface molecule and the at least one second surface molecule, a second input may remove a combination between the third surface molecule and the fifth surface molecule, and a third input may form a combination between the fourth surface molecule and the sixth surface molecule.

A first interaction between the nano-receptor and the nano-floater may be controlled by a first input and a second input, among the plurality of nanoparticles, a second interaction between another one first nano-receptor and another one first nano-floater may be controlled by a third input and a fourth input, and the first input and the third input may be of the same type and the second input and the fourth input are of the same type.

A color of an image signal detected according to the first interaction and a color of an image signal detected according to the second interaction may be different from each other.

The tethering between the nano-receptor and the nano-floater may be disassembled by the first input and the second input, and the tethering between the first nano-receptor and the first nano-floater may be disassembled by the third input and the fourth input.

According to another aspect of the present invention, a lipid nanotablet in a supported lipid bilayer to which a plurality of nanoparticles are integrated in nanoparticle units, includes: a first nano-receptor; a second nano-receptor; a first nano-floater that interacts according to at least one input for the first nano-receptor; and a second nano-floater that interacts according to a first input for the second nano-receptor, wherein wiring between a first logic gate including the first nano-receptor and a second logic gate including the second nano-receptor may be determined based on the first nano-floater and the second nano-floater.

The first nano-floater and the second nano-floater may be of the same type, and the first logic gate and the second logic gate may be AND wired.

The at least one input may include two inputs, and the lipid nanetable-nanotablet may output a result of interaction of the first nano-receptor and the first nano-floater according to the two inputs and a result of interaction of the second nano-receptor according to the first input.

Tethering between the first nano-receptor and the first nano-floater may be disassembled by the two inputs and thus the first nano-floater may be released, and the first nano-floater and the second nano-receptor may be tethered by the first input.

Tethering between the first nano-receptor and the first nano-floater may be disassembled by at least one of the two inputs and thus the first nano-floater may be released, and the first nano-floater and the second nano-floater may be tethered by the first input.

Tethering between the first nano-receptor and the first nano-floater may be disassembled by one of the two inputs and thus the first nano-floater may be released, the first nano-floater and the second nano-floater may be tethered by the first input, and the first nano-receptor and the first nano-floater may be tethered by the other one of the two inputs.

The first nano-floater and the second nano-floater may be of different types, and the first logic gate and the second logic gate may be OR wired.

The at least one input may include two inputs, and the lipid nanotable may output a result of interaction of the first nano-receptor and the first nano-floater according to the two inputs and a result of interaction of the second nano-receptor and the second nano-floater according to the first input.

Tethering between the first nano-receptor and the first nano-floater may be disassembled by the two inputs and thus the first nano-floater may be released, and, the second nano-receptor and the second nano-floater may be disassembled by the first input and thus the second nano-floater may be released.

Tethering between the first nano-receptor and the first nano-floater may be disassembled by at least one of the two inputs and thus the first nano-floater may be released, and the second nano-receptor and the second nano-floater may be disassembled by the first input and thus the second nano-floater may be released.

According to another aspect of the present invention, a lipid nanotable in a supported lipid bilayer to which a plurality of nanoparticles are integrated in nanoparticle units, includes: a first logic gate where a first nano-receptor and a first nano-floater interact with each other according to a selected input and a first input; and a second logic gate where a second nano-receptor and a second nano-floater interact with each other according to the selected input and a second input, wherein one of the first logic gate and the second logic gate may release a nano-floater that corresponds according to a corresponding input among the first input and the second input according to the selected input.

The first nano-receptor and the first nano-floater may be disassembled by the first input, the first nano-receptor and the first nano-floater may be assembled by the selected input, and the second nano-receptor and the second nano-floater may be disassembled by the second input and the selected input.

The lipid nanotablet may further include: a first surface molecule and a second surface molecule that are tethered to the surface of the first nano-receptor; and a third surface molecule and a fourth surface molecule that are tethered to the surface of the first nano-floater, wherein a combination between the first surface molecule and the third surface molecule is removed by the first input, and the second surface molecule and the fourth surface molecule are combined by the selected input.

The lipid nanotablet may further include: a fifth surface molecule and a sixth surface molecule that are tethered to the surface of the second nano-receptor; and a seventh surface molecule and an eighth surface molecule that are tethered to the surface of the second nano-receptor, wherein a combination of the fifth surface molecule and the seventh surface molecule may be removed by the second input, and the sixth surface molecule and the eighth surface molecule may be removed by the selected input.

A nanobio computing method in a supported lipid bilayer to which a plurality of nanoparticles are integrated in nanoparticle units, according to another aspect of the present invention, includes: generating a plurality of interactions between a plurality of immobile nano-receptors in the lipid bilayer and a plurality of mobile nano-floaters in the lipid bilayer according to inputs; generating a plurality of signals based on the plurality of interactions; tracking signals generated only from the plurality of nano-receptors among the plurality of signals; and determining a logic result based on the tracking result.

The tracking may include: detecting a signal higher than a detection parameter in generated image data by dark-field microscopy; generating a segmented signal by distinguishing a boundary of the detected signal; providing positions of nanoparticles by localizing a center of the segmented signal; identifying a nano-receptor by comparing the positions of the nanoparticles through a plurality of frames; and sampling a signal corresponding to the identified nano-receptor.

An increase in intensity of a signal in the tracking result may indicate assembly of a nano-receptor corresponding to an input among the plurality of nano-receptors and a nano-floater corresponding to the input among the plurality of nano-floaters.

A decrease in intensity of the signal in the tracking result may indicate disassembly of a nano-receptor corresponding to an input among the plurality of nano-receptors and a nano-floater corresponding to the input among the plurality of nano-floaters.

Advantageous Effects

A lipid nanotablet that can systematically design and build circuits based on digital design principles with a scalable integrated platform having real-time readout and control functions, while overcoming the limitations of a solution-based existing approach that can only drive one kind of computation at a time, can be provided.

DESCRIPTION OF THE DRAWINGS

FIG. 17A to FIG. 17F show design principles of nanoparticle logic gates.

MODE FOR INVENTION

Figure 1A:
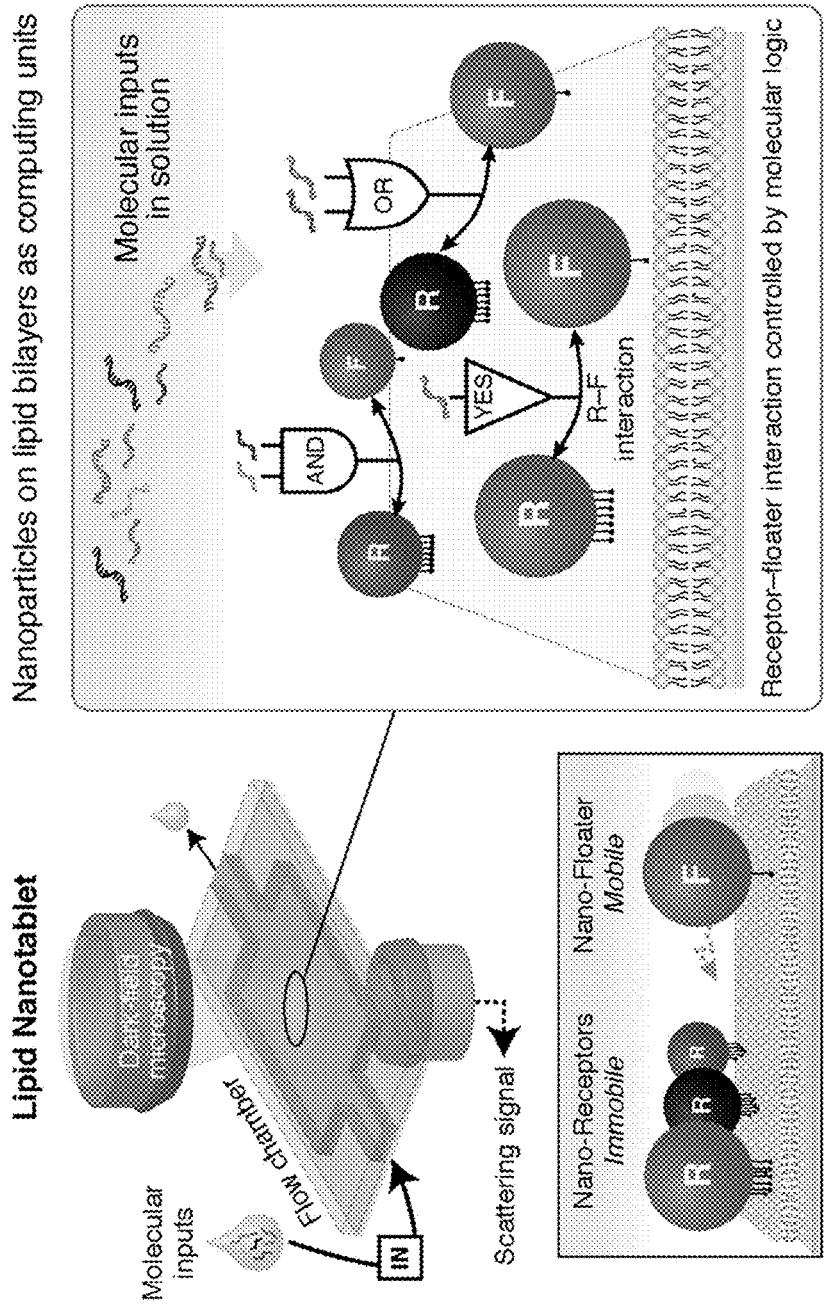
FIG. 1A to FIG. 1C show single nano-particle logic computation on LNT.

The invention disclosed in the present disclosure can be applied to overall nanoparticle computing based on a lipid membrane to which nanoparticles are attached rather than being limited to DNA molecules. Molecules that can be attached to the nanoparticle may include various chemical ligands such as DNA, RNA, proteins, peptides, metal chelators, and the like. That is, the present invention can be applied not only to biocomputing but also to nanoparticle-lipid platform-based molecular computing.

A cell membrane biologically serves the same function as a circuit board of an electronic circuit. The cell membrane compartmentalizes a receptor from an information-rich external fluid of the cell while hosing various receptor proteins in a computation unit, and performs complex functions by guiding receptors to interact laterally on the two-dimensional fluid surface. Each receptor, which is an active constituent of a biological circuit, takes chemical and physical cues as "inputs" such as binding events with ligands and changes in membrane voltage, and generate "outputs" such as conformational changes and dimerization/dissociation reactions. The membrane may allow many different computing processes to occur in parallel.

Taking inspiration from cellular membranes, a lipid nanotablet (LNT) includes a supported lipid bilayer (SLB) to which light-scattering plasmonic nanoparticles are tethered, and performs logic computation using the SLB. To perform the computation, it is programmed that the SLB-tethered nanoparticles interact with one another using surface ligands.

SLBs, which have been widely used as synthetic mimics for cell surfaces, are used as "chemical circuit boards" here, and nanoparticles that perform computation are placed on the surface. Tethering nanoparticles a lipid bilayer enables the following.

First, particle-to-particle interactions are confined to occur only through lateral diffusion at a 2D reaction space. Second, parallel in situ tracking and analysis of the nanoparticle interactions can be achieved with single-particle resolution because a large number of light-scattering nanoparticles are confined in the focal plane of dark-field microscopy (DFM). Third, nanoparticles are compartmentalized from solution containing molecular inputs. "Nano-bio" computing, which is an unconventional way to carry out computation with single nanoparticles, can be provided by using such features. The nano-bio computing occurs at the interface of the nanostructures and biomolecules. In order to prove this, in the present disclosures, nanoparticles are tethered to the lipid bilayer by using strong biotin-streptavidin interaction, and uses DNA as molecular inputs DNA and surface ligands. However, the surface ligand of the present invention is not limited to DNA, and molecules that can provide bondings capable of controlling interactions between nanoparticles by reacting specifically to molecular inputs, for example, antigen-antibody bonding, ligand-receptor bonding, chelate bonding, covalent bonding, hydrogen bonding, van der Waals bonding, bonding by hydrophobic interactions, electrostatic bonding, or bonding by chemical reaction, and bonding molecules capable of providing functional bonding, electrostatic bonding, or chemical bonding may be applied.

Figure 1B:
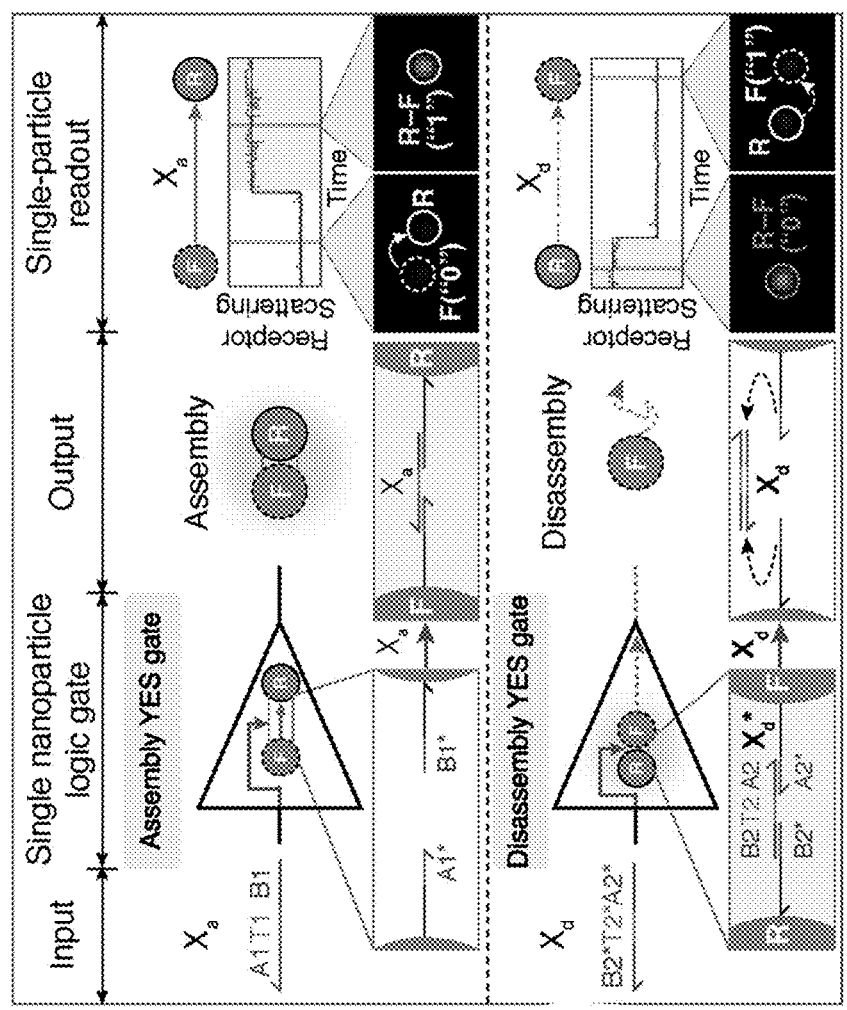
Figure 1C:
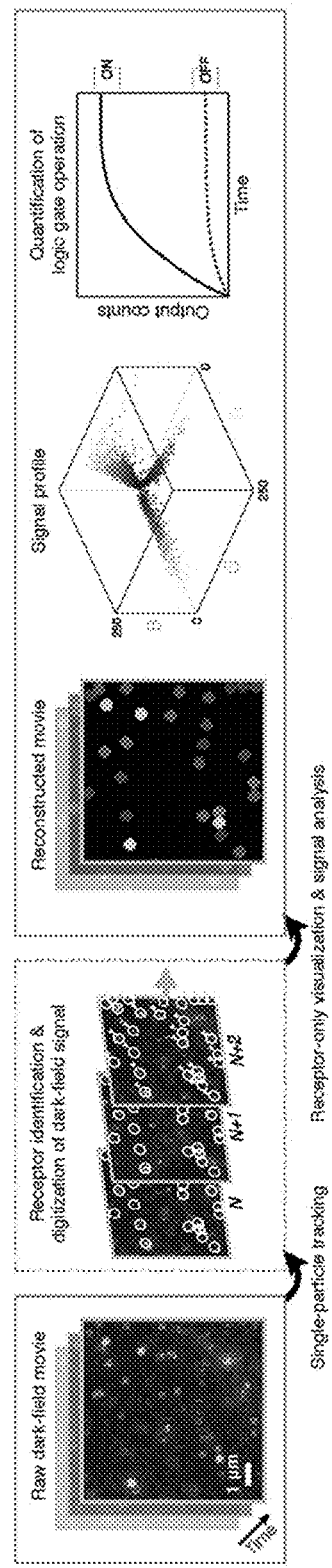

FIG. 1A to FIG. 1C show single nano-particle logic computation on LNT.

Figure 2A:
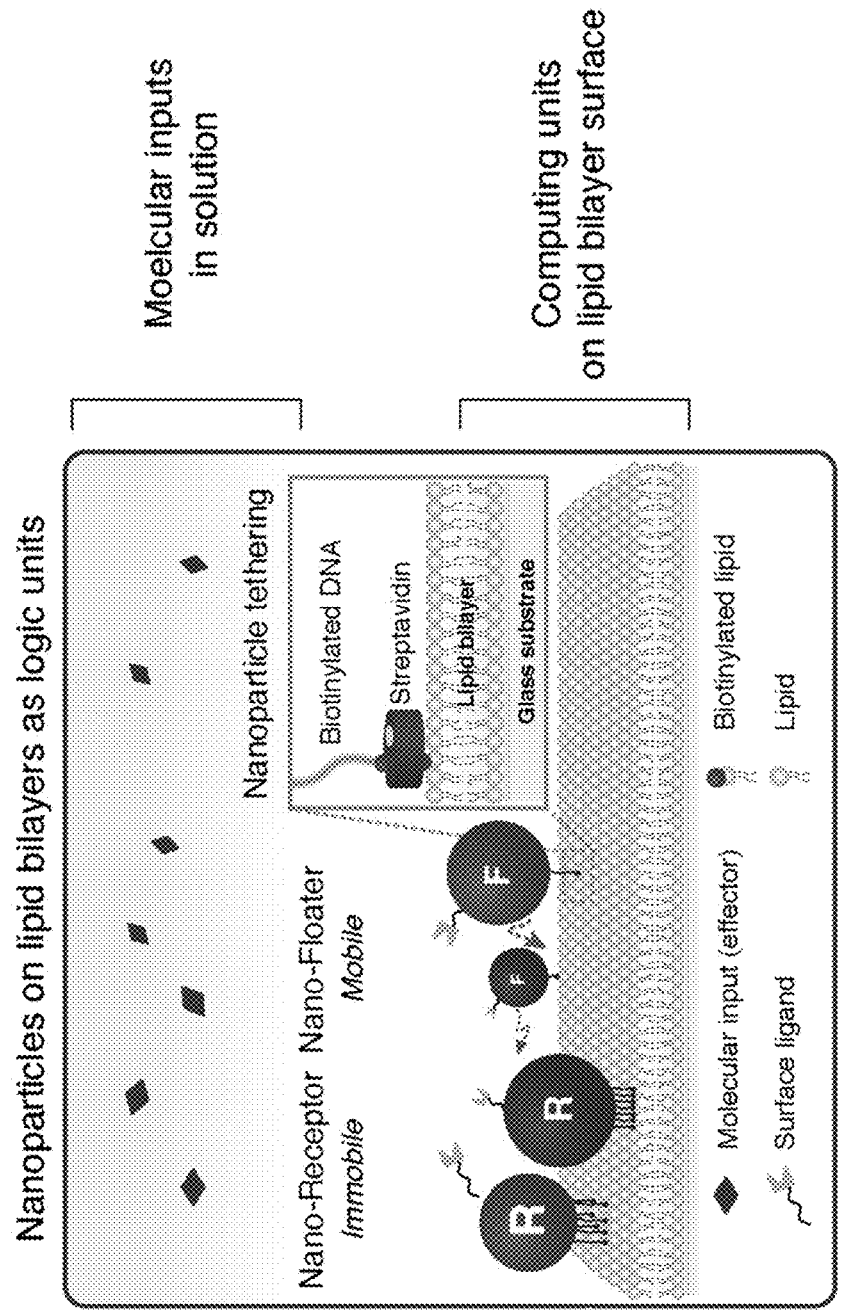
FIG. 2A and FIG. 2B are schematic views for description of an LNT platform.
Figure 2B:
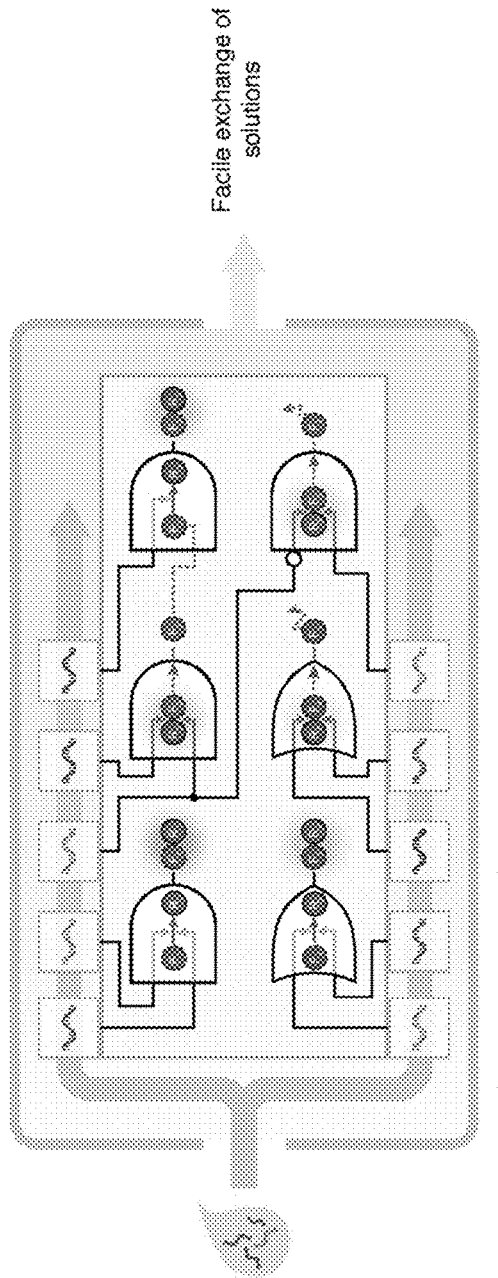

FIG. 2A and FIG. 2B are schematic views for description of an LNT platform.

As shown in FIG. 1A, FIG. 2A, and FIG. 2B, an LNT consists of a flow chamber, of which the bottom substrate is coated with an SLB chip interfaced with nanoparticles whose optical signals, mobilities, and surface DNA ligands are readily tunable.

DNA sequence and experiment conditions related to single-nanoparticle logic computation are summarized in Tables 1, 2, and 13.

In FIG. 1A, a schematic structure of the LNT platform is illustrated. Two classes of nanoparticles, immobile nano-receptors (NRs), and mobile nano-floaters (NFs) are tethered to the supported lipid bilayer (SLB). The two nano-particles take DNA as inputs, and changes interactions of the nanoparticles with output of a logic operation. Then, an assembly or disassembly reaction occurs.

As shown in FIG. 2A, the lipid nanotablet uses molecules as inputs and performs a nanoparticle logic computation through a dynamic nanoparticle network that is connected to the supported lipid bilayer, and provides optical readings in situ with an output that can be easily read and analyzed with a dark field microscope. The nanoparticle logic unit is connected to the lipid bilayer surface through strong interaction between a biotinylated DNA linker on the nanoparticle surface and streptavidins tethered to the biotinylated DOPE (1,2-dioleoyl-sn-glycero-3-phosphoethanolamine) lipid. The bound nanoparticle receptor and floater serve as logic gates, and process molecular information in the solution by using programmable stimuli-responsive surface ligands.

As shown in FIG. 2B, the supported lipid bilayer surface is a chemical breadboard for nanoparticle computation. The nanoparticle logic gate is integrated to a lipid bilayer chip through chemical tethering. Basically, many different nanoparticle logic gates are integrated to the single lipid bilayer surface and thus each logic gate can perform logic computation in parallel manner while producing a distinct optical signal. When the nanoparticle logic gate is integrated on the lipid chip, a washing buffer, a nanoparticle gate, or a solution including molecule inputs may exchange the bonded particles without the tethered particles. Also, dark field imaging can be performed in situ during a solution exchange.

Figure 3A:
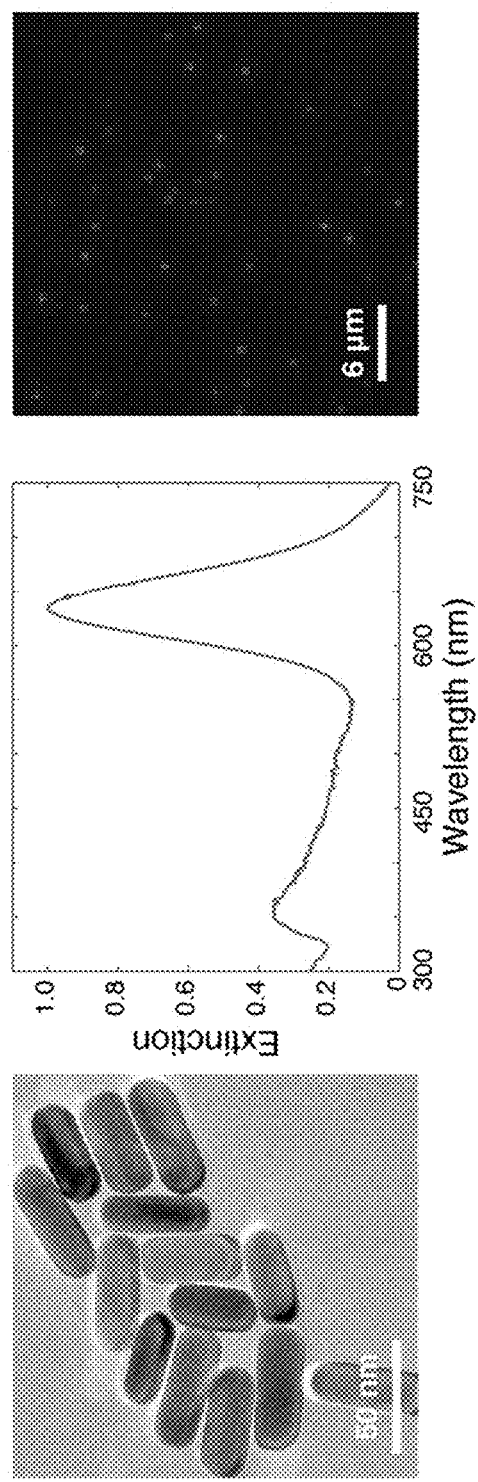
FIG. 3A to FIG. 3C show characteristics of DNA-modified nanoparticles.
Figure 3B:
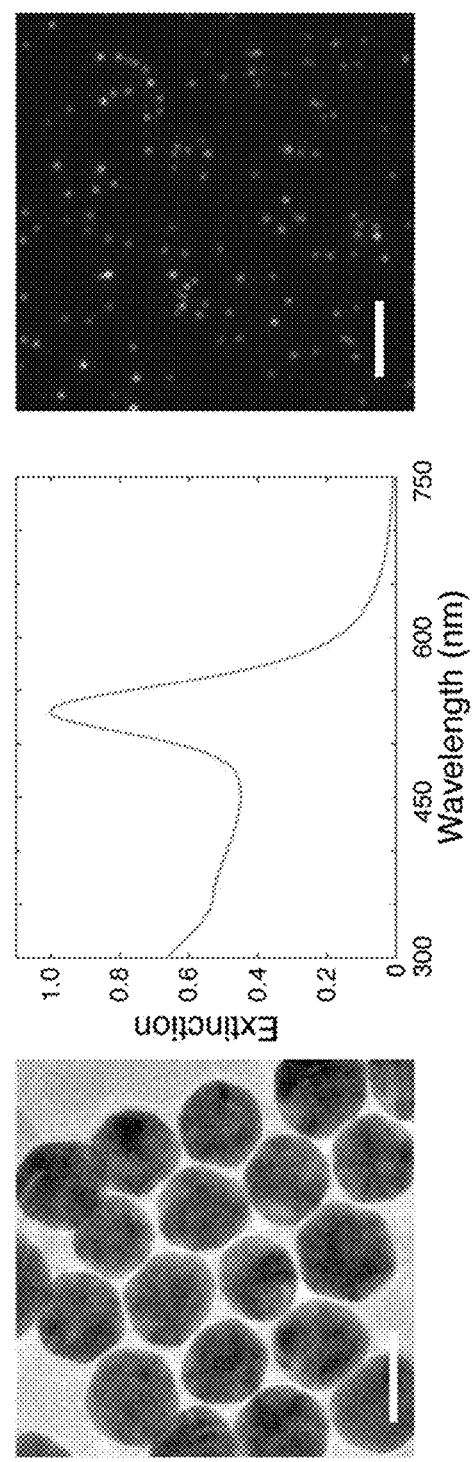
Figure 3C:
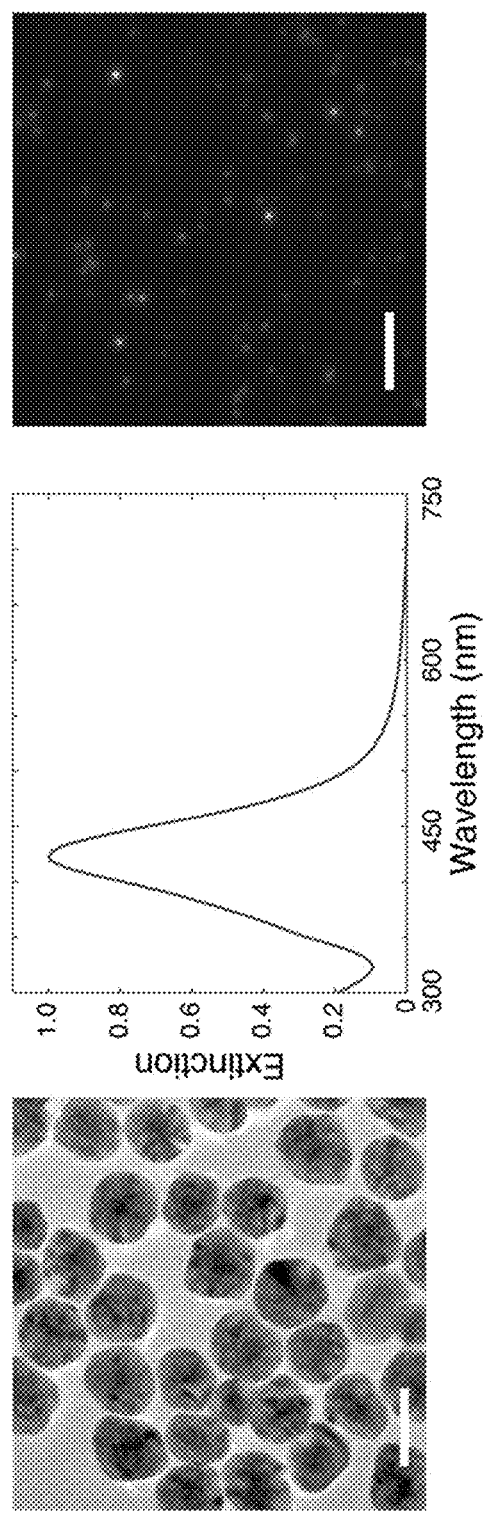

FIG. 3A to FIG. 3C show characteristics of DNA-modified nanoparticles.

In FIG. 3A, a gold nanorod with a silver nanoshell that mainly displays a red (R) scattering signal is illustrated (diameter=22.2±1.2 nm, length=55.9±2.9 nm, aspect ratio=2.5).

In FIG. 3B, a gold nanosphere that mainly displays a green (G) scattering signal is illustrated (diameter=50.0±1.8 nm).

FIG. 3C, a silver nanosphere on a gold seed that mainly displays a blue (B) scattering signal (diameter=54.8±3.1 nm).

In FIG. 3A to FIG. 3C, the first columns show transmission electron microscopy images, the second columns show extinction spectrum obtained from an ultraviolet-visible spectrophotometer, and the third spectrums are normalized with 1 optical density (OD). The third columns show darkfield microcopy (DFM) images.

As shown in FIG. 3A to FIG. 3C, there are three types of core nanoparticles, for example, the gold nanorod with the silver nanoshell, the gold nanosphere, and the silver nanosphere in the order of FIG. 3A to FIG. 3C, are used in as gold seeds that display red R, green G, and blue B scattering signals, respectively. Computation, by the nanoparticle units on LNT are directly visualized by DFM, and the use of a flow chamber enables facile exchange of solutions without washing out nanoparticle circuits in the system.

Figure 4A:
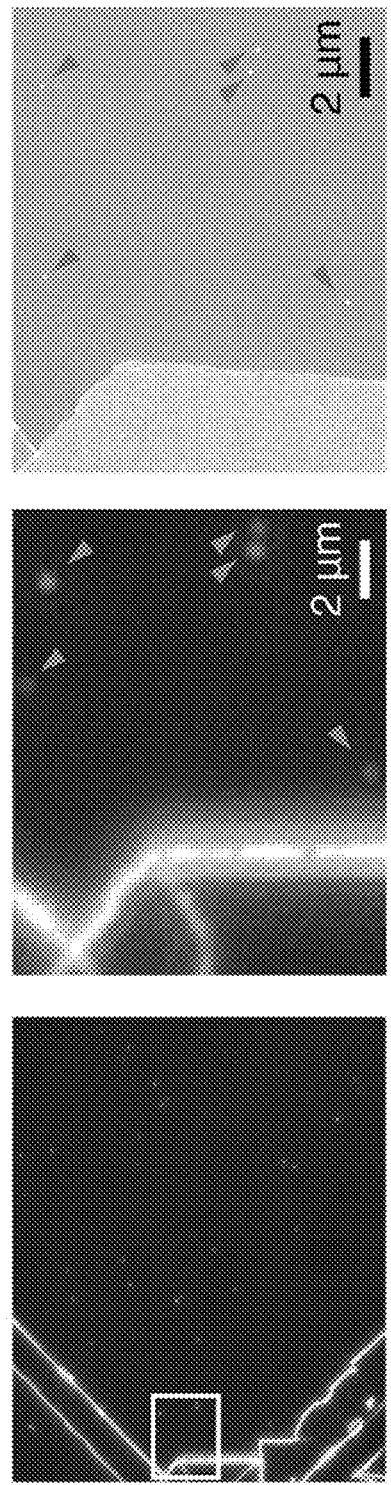
FIG. 4A to FIG. 4C show correlation DFM-SEM images for analysis of a single nanoparticle scattering signal.
Figure 4B:
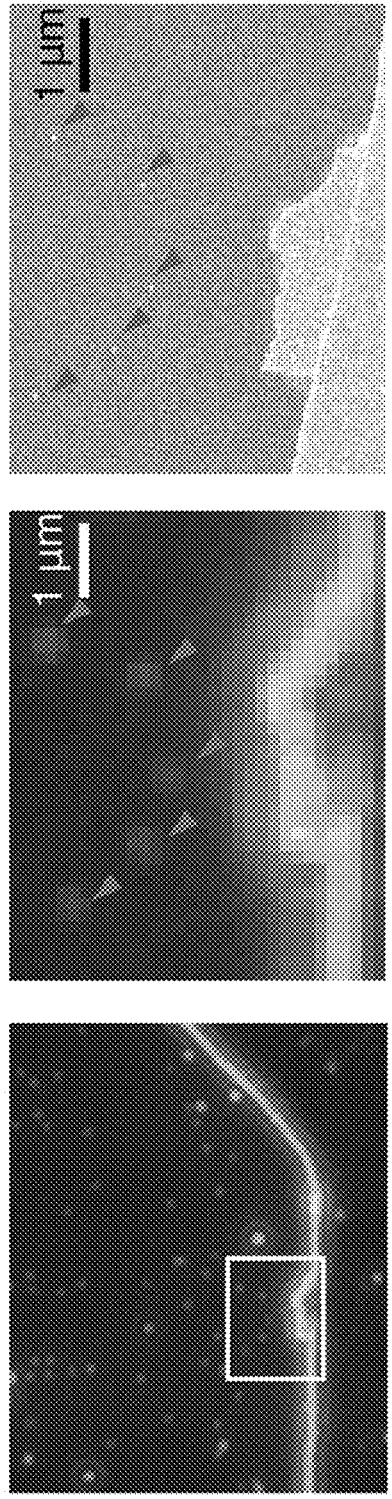
Figure 4C:
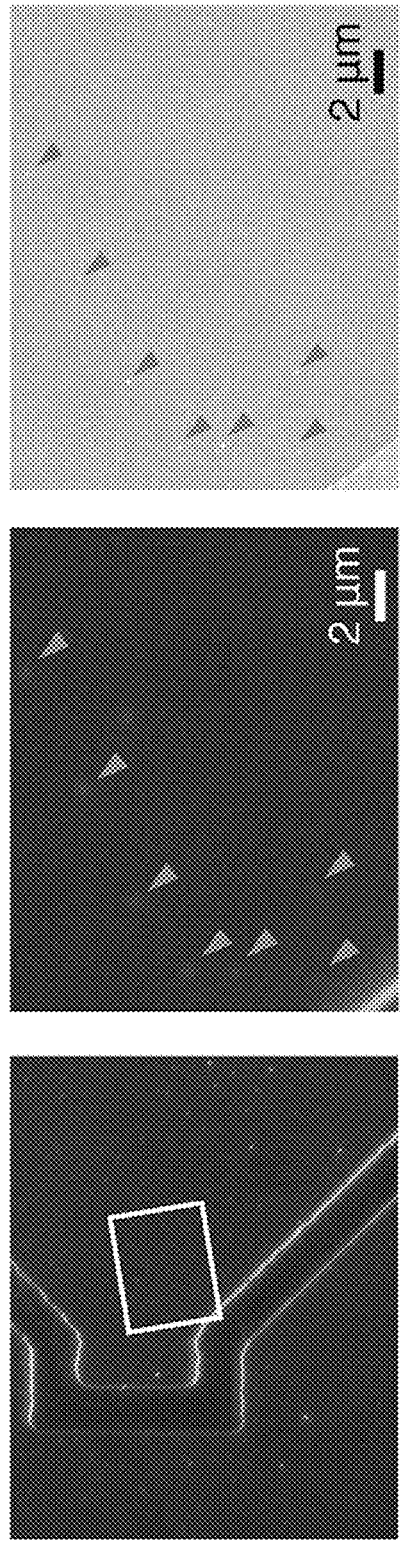

FIG. 4A to FIG. 4C show correlation DFM-SEM images for analysis of a single nanoparticle scattering signal.

In FIG. 4A to FIG. 4C, the left columns are DFM images of nanoparticles on a patterned glass substrate, the center columns are enlarged DFM images in marked areas in the images of the left columns, and the right columns are scanning electron microscopy (SEM) images at the same positions of the image of the center columns.

FIG. 4A shows DFM and scan SEM images of a gold nanorod (R nanoparticles) with a silver nanoshells, FIG. 4B shows DFM and SEM images of a gold nanosphere (G nanoparticles), and FIG. 4C shows DFM and SEM images of a gold nanosphere (B nanoparticles) with a silver nanoshell.

It can be determined that Cr-patterned glass substrates help to find the same position in both images. The co-relationship of the two image shows that characterized scattering signals shown in FIG. 3A to FIG. 3C come from a single nanoparticle.

When two plasmonic nanoparticles are in close proximity, the nanoparticles exhibit a plasmon binding effect, and thus it is possible to determine whether a bright particle is a single nanoparticle or an aggregation of nanoparticles by analyzing the scattering intensity of the DFM image. Compared with the same position in the SEM image, it can be confirmed that bright plaques in the initial state in the DFM image are from single nanoparticles.

As basic constituents of LNT, two classes of nanoparticles, nano-receptors (NRs) and nano-floaters (NFs), are used. A surface DNA ligand of each of the nano-receptor and the nano-floater is designed with a method in which the receptor-floater interaction (e.g., through assembly or disassembly) is controlled according to a result of logic computation that takes DNA molecules from the solution.

Figure 5A:
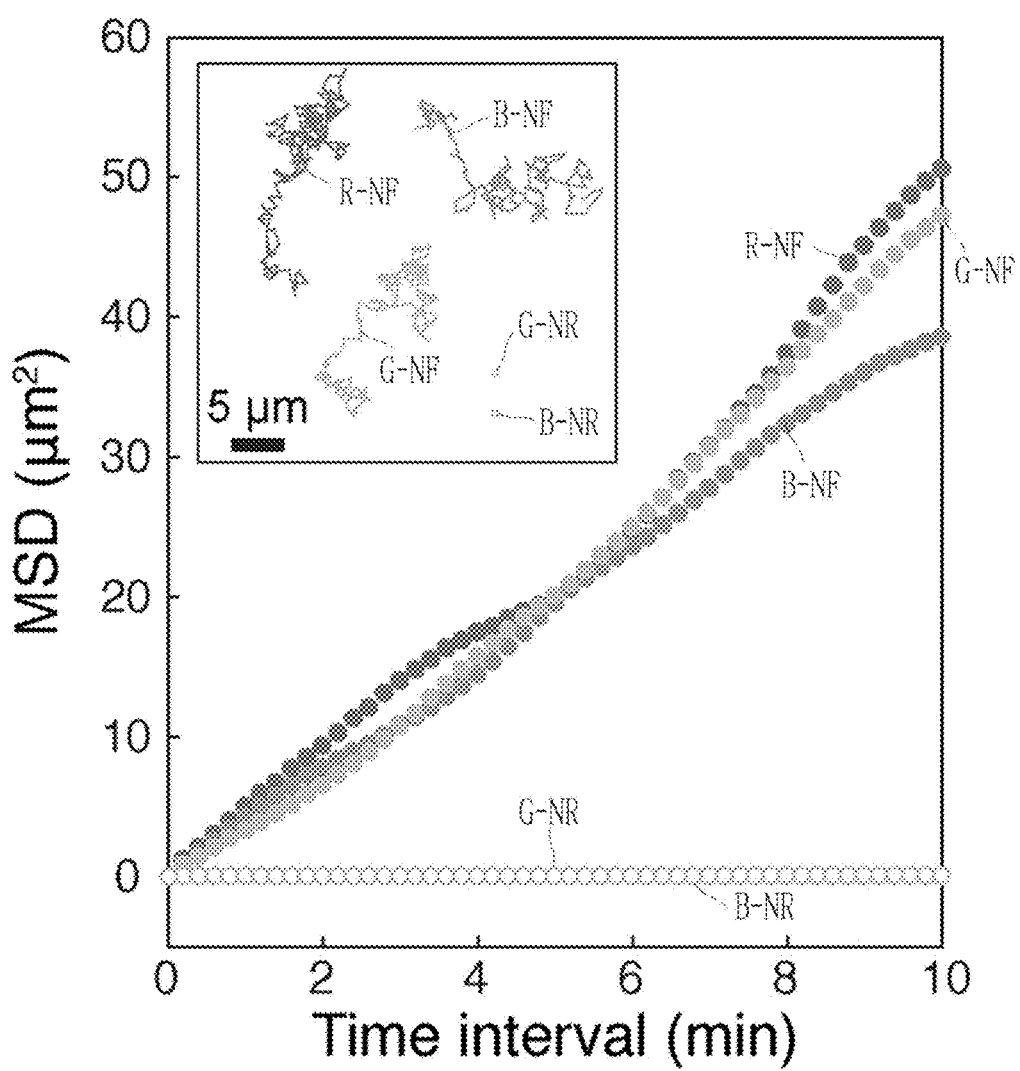
FIG. 5A to 5B show diffusion kinetics of nanoparticles tethered to the supported lipid bilayer.
Figure 5B:
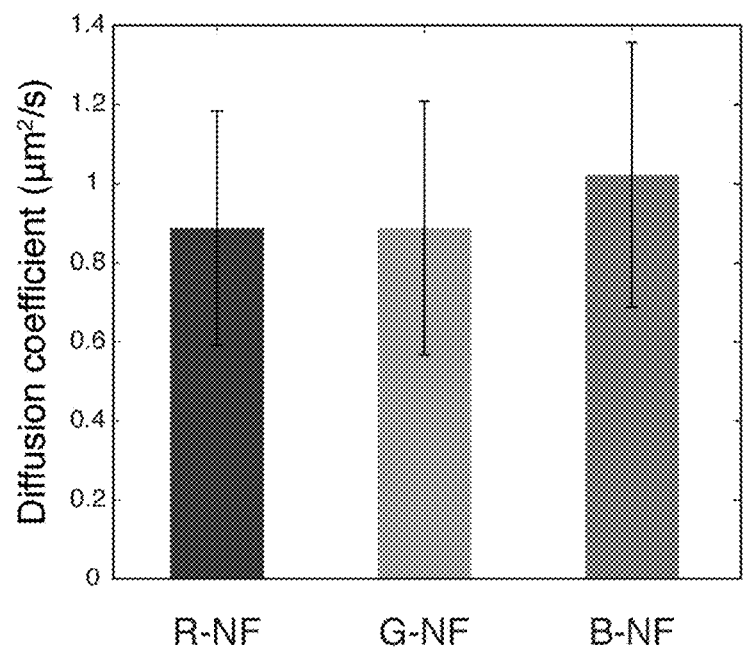

FIG. 5A and FIG. 5B show diffusion kinetics of nanoparticles tethered to the supported lipid bilayer.

In FIG. 5A, a mean square displacement (MSD) with respect to time to plot five representative diffusion orbits is illustrated. As shown in FIG. 5A, an MSD plot of three mobilities R, G, and B and nano-floaters R-NF, G-NF, and B-NF show a linear relationship of random 2D Brownian motion and an MSD plot of the G and B receptors G-NR and B-NR shows immobility thereof.

In FIG. 5B, an average diffusion coefficient of diffused R-NF (Ntot=154), G-NF (Ntot=194), and B-NF (Ntot=247) is illustrated.

As shown in FIGS. 5A and 5B, the receptors are immobile on an SLB because their lateral diffusion is limited by a large number of biotinylated DNA linkers that interact with streptavidins on an SLB. 34% to 50% of the receptor surface valency is functionalized with the linkers. The receptors are monitored throughout the computing process, serving as reporters of nanoparticle computation.

Floaters, of which biotin linker valency ranges from 0.4% and 0.5%, are highly mobile on an SLB with a diffusion coefficient of about 1.0 $\mu m^2/s$.

Due to the high mobility, NFs can actively interact with NRs across space and time, while functioning as active units of computation. The surface DNA ligands mediate a receptor-floater interaction, taking DNA molecules as inputs and inducing assembly or disassembly of the receptor-floater complex as an output.

An action of the floater tethered to the SLB is binary at the level of a single particle. That is, for a given observation period, the floater either discretely switches its state (ON) through assembly or disassembly or it does not. When digital actions of each floater are controlled with Boolean logic, a receptor-floater pair can be implemented as a single logic gate.

In FIG. 1B, a nanoparticle YES gate is illustrated as an example of a logic gate implemented by a receptor-floater pair.

In FIG. 1B, a receptor-floater pair, which is a YES logic gate, is illustrated. A green nano-receptor G-NR and a green nano-floater G-NF that exhibit a predominant green can be used in the YES gates.

When an input DNA ($X_a$) induces an assembly reaction between the receptor and the floater, the floater-receptor pair is defined as an assembly YES gate. When the input DNA ($X_d$) is output through a strand displacement disclosed by a toehold domain T2 and thus the receptor-floater (R-F) pair induces disassembly, the floater-receptor pair is defined as a disassembly YES gate. In the drawing, "T" denotes a toehold domain, "A" and "B" are building domains, and function domains may be connected in the order of A-T-B or B-T-A. The arrow head indicates a 3' end, and the asterisk "*" indicates complementarity. Each logic gate may be displayed in the reaction graph shown in FIG. 1B.

In the Assembly YES gate, a G-NF switches its conformation state from a diffusible monomer ("0") to an immobile dimer ("1") through association with a G-NR in response to a single-stranded DNA input ($X_a$) that can hybridize with the surface DNA ligands of both the receptor and the floater.

In the Disassembly YES gate, a G-NF is initially bound to a G-NR via hybridization with an oligonucleotide ($X_{d*}$). This step is termed pre-dimerization. The G-NF is then released from the G-NR and switches its state from an immobile dimer ("0") to a diffusible monomer ("1") when a DNA input ($X_d$) removes the pre-existing DNA bond $X_{d*}$ via toehold-mediated strand displacement.

DNA sequence and experimental conditions of the Assembly YES gate and the Disassembly YES gate shown in FIG. 1B are disclosed in Table 1 and Table 13.

Figure 6A:
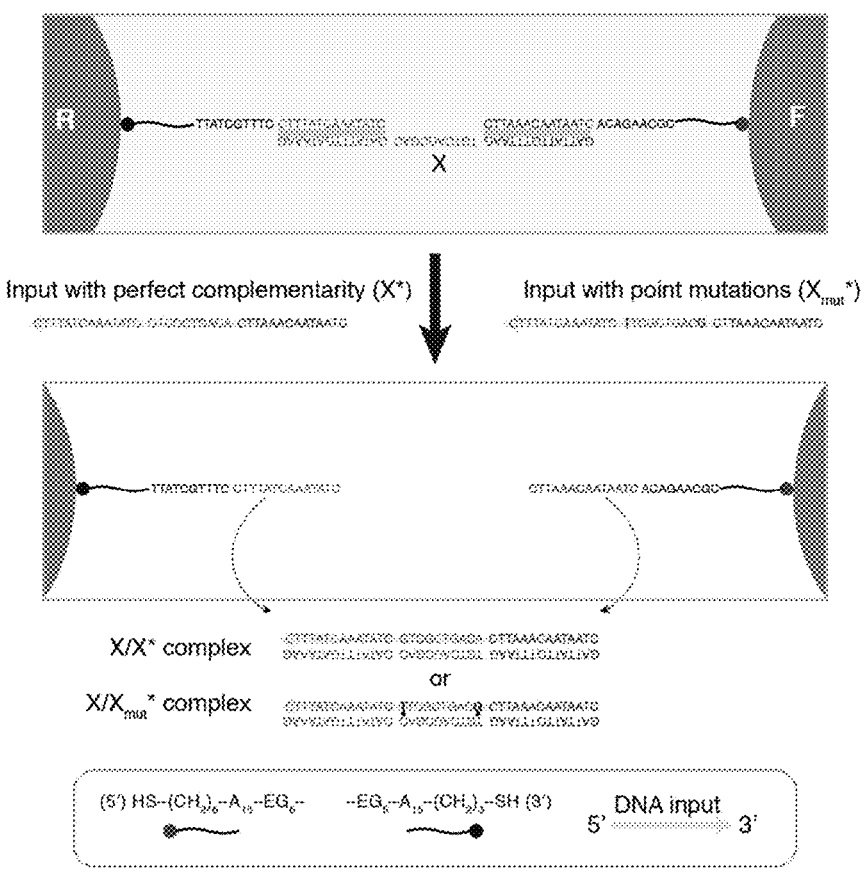
FIG. 6A and FIG. 6B show operation of the single input separation YES gate based on the toehold-mediated strand displacement.
Figure 6B:
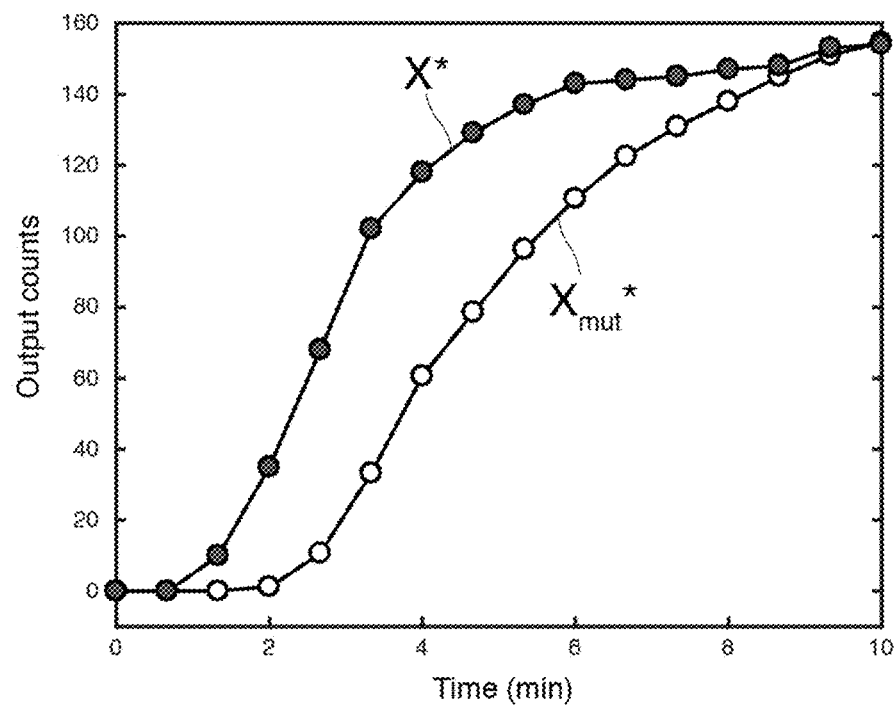

FIG. 6A and FIG. 6B show operation of the single input separation YES gate based on the toehold-mediated strand displacement.

In FIG. 6A, a separation reaction that uses a fully complementary input and a mismatched input is illustrated in a sequence level. Two point transitions and mismatched base pairs ("T" and "G" at opposite ends of "TTCGCTGACG" in Xmut* of FIG. 6A) at lateral ends of the toehold domains (from A to G, from G to T) are emphasized.

In FIG. 6B, dark-field kinetics experiment plots obtained with respect to the two inputs are illustrated. In FIG. 6B, outputs with respect to the fully complementary input and the mismatched input are respectively displayed. Due to the high concentration of 500 nM of the inputs and a long toehold domain, even if there is a base mismatch, the equilibrium is pushed back to separation. Resultantly, reactions under the two conditions are saturated after a sufficient operation time period. However, the fully complementary input induces faster response of the separation gate, and this indicates that the system can identify mismatched inputs under a specific condition by using kinetics information. In FIG. 6A, EG denotes an ethylene glycol unit.

For inputs, the logic values "0" and "1" represent the absence and presence of an input DNA in the solution. For outputs, "1" represents a G-NF bound to a G-NR (i.e., an R-F dimmer) for an Assembly gate, and a diffusible, monomeric G-NF for a Disassembly gate. "0" indicates the floaters staying in their initial states.

The information on state-switching behavior of floaters can be obtained by tracking signal changes of receptors. For example, the Assembly YES gate produces output "1" when a G-NF assembles onto a G-NR through the input DNA resulting in a step-wise increase in G intensity of the G-NR.

"Nanoparticle reaction network" abstraction may be used to represent behaviors of logic-gated nanoparticles. The abstraction is based on a directed graph where a node is represented by a nanoparticle and an edge is represented by logic, inputs, and reaction types. As shown in FIG. 1B, assembly reaction is marked by a solid arrow directed from a floater to a receptor, and disassembly reaction is marked by a dashed arrow directed from a receptor to a floater. The nanoparticle logic gate may be designed to generate a characteristic, plasmonic coupling-induced signal that is specific to a combination of a receptor-floater pair. Thus, multiple nanoparticle logic gates can be analyzed in parallel as long as each gate provides a distinct optical readout.

Figure 7:
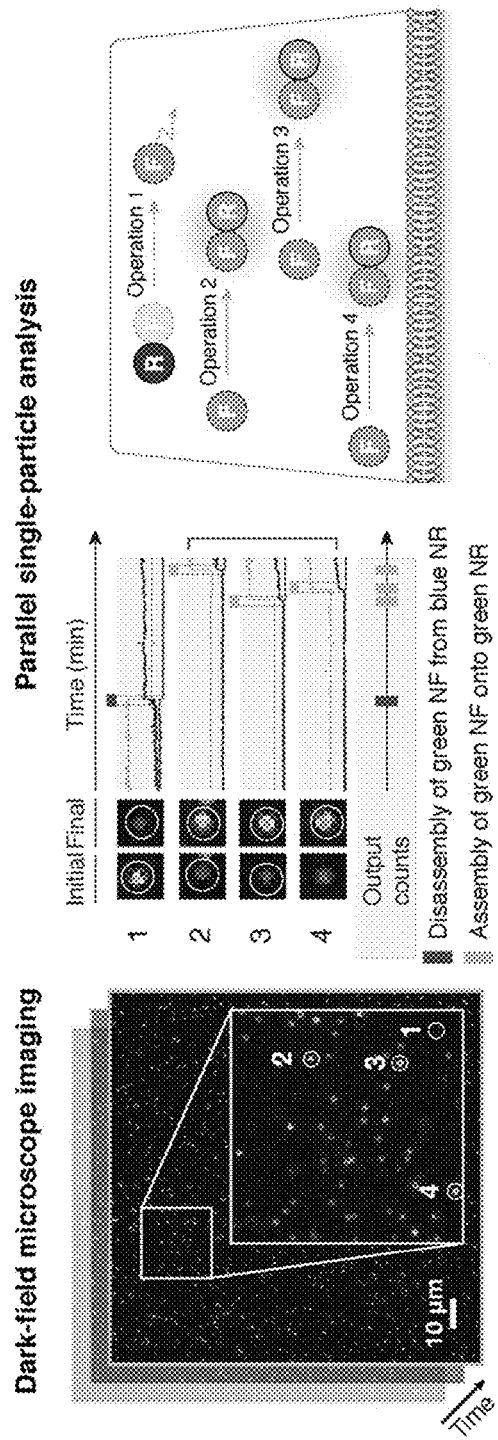
FIG. 7 shows parallel, single-particle analysis in the nanoparticle logic gate operation by a dark-field microscope.

FIG. 7 shows parallel, single-particle analysis in the nanoparticle logic gate operation by a dark-field microscope.

As shown in FIG. 7, each of the multiple nanoparticle logic gates can be analyzed in parallel as long as each gate generates a distinct optical signal as an output. In FIG. 7, in the enlarged box area of dark-field microscope imaging and parallel single-particle analysis, B-NR is indicated by a darker shade than G-NF. Since a plasmonic coupling-induced change in a nanoparticle scattering signal relies on a receptor-floater pair related to interaction, multiple logic gates that generate unique optical signals can be readily designed For example, when an Assembly gate is composed of a G-NR and a G-NF and a Disassembly gate is composed of a B-NR and a G-NF, the two gates can be simultaneously executed. In the two signals, an increase in G intensity of a G-NR and a decrease in G intensity of a B-NR are readily discernible.

A sufficiently high density of nanoparticles needs to be maintained to ensure that a large number of logic-gated nanoparticle reactions can occur within a short period of time. Approximately over 4000 nanoparticles (>3700 receptors and 300 floaters) tethered to a unit area (180×180 $\mu m^2$) are monitored for computing processes that typically last 15 minutes to 30 minutes.

Figure 8A:
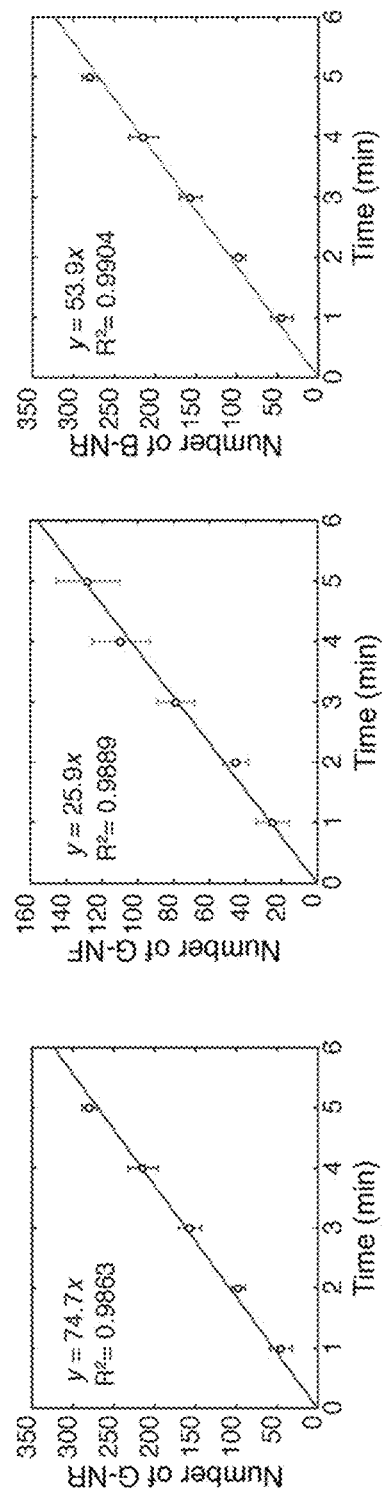
FIG. 8A and FIG. 8B show that nanoparticles are tethered to logic gates of the supported lipid bilayer.
Figure 8B:
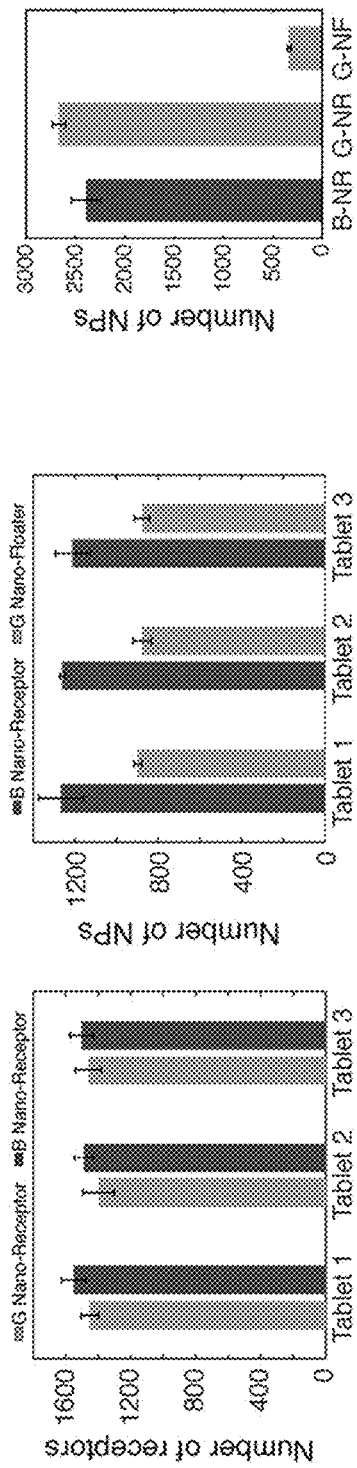

FIG. 8A and FIG. 8B show that nanoparticles are tethered to logic gates of the supported lipid bilayer.

In FIG. 8A, a plot between a number of nanoparticles NPs tethered to the supported lipid bilayer and an incubation time is illustrated In FIG. 8A, tethering processes of 2.5 pM G-NR at the left, 2.6 pM G-NF at the center, and 2.2 pM B-NR at the right are illustrated. At each time, the number of each nanoparticle was counted in a region of 90 $\mu m \times 90$ $\mu m$ for four different positions. The error bar is the standard deviation calculated based on the number of particles obtained at four positions. As shown in the plot illustrated in FIG. 8A, the number of tethered particles is linearly proportional to an incubation time of the lipid bilayer chamber together with the solution including biotinylated nanoparticles ($R^2$>0.98). In addition, as expected from a higher linker density, the plot shows that receptor tethering is faster than floater tethering. Such a linear relationship enables accurate control of nanoparticle density in the lipid bilayer.

In FIG. 8B, the number of tethered nanoparticles in three replicate lipid flow chambers (e.g., tablets Tablets 1 to 3) is illustrated. A combination of G-NR and B-NR is illustrated in the left in FIG. 8B, and a combination of B-NR and G-NF is illustrated in the center in FIG. 8B. On each tablet, the number of nanoparticles are counted at four different positions in a 90 $\mu m \times 90$ $\mu m$ area after tethering. The error bar is the standard deviation calculated based on the number of particles obtained at the four positions. The tablet-to-tablet variability in particle count is negligible.

In the right side in FIG. 8B, the number of each of the three tethered nanoparticles B-NRs, G-NRs, and G-NFs measured at the four different positions in the lipid chamber is shown. The error bar is the standard deviation calculated based on the number of NPs obtained at four positions. These results show that the tethering of nanoparticles in lipid nanotablets can be controlled and is robust over a large area of the lipid bilayer regardless of the nanoparticle type and mobility.

The numbers of receptors is set to be higher than that of floaters to minimize trimer and tetramer formation. Such a condition allows the floaters to switch exclusively between the monomer and dimer stages.

Figure 9:
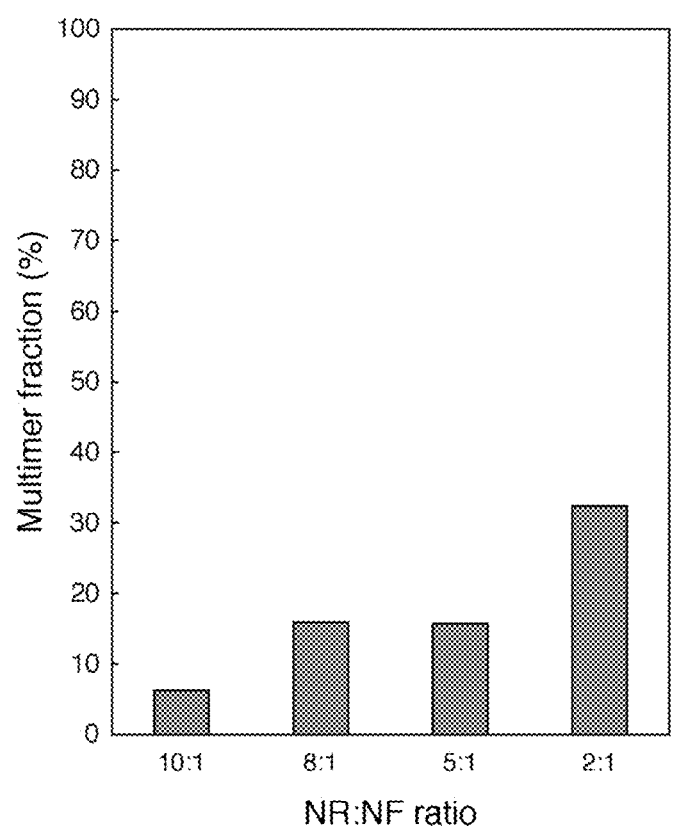
FIG. 9 is a graph that shows a degree of multimer-forming reactions by MATLAB-based simulation.

FIG. 9 is a graph that shows a degree of multimer-forming reactions by MATLAB-based simulation.

As shown in FIG. 9, an NF ratio that forms a polymer (trimer or tetramer) in an assembly reaction simulated in the lipid bilayer with respect to a given NR/NF ratio may be estimated by using MATLAB-based simulation. In NR/NF ratios of 10:1, 8:1, 5:1, and 2:1, 6%, 15%, 15%, and 34% of floaters formed the polymer with the assembly reaction. For example, two assembly reactions between one receptor and two floaters result in a trimer. A total of nanoparticles in the simulated system is set to about 1800 in the area of 128×128 $\mu m^2$. The diffusion coefficient of NF is distributed to satisfy a normal distribution of 0.9 $\mu m^2/s$ on average and a standard deviation of 0.3 $\mu m^2/s$ for consistency with the experimental results.

In FIG. 1C, receptor-only digital image processing for the clear and quantitative visualization of nanoparticle logic computation is illustrated. Immobile signals from receptors are specifically identified and digitalized for visualization. Such an analysis provides reconstructed dark-field video with enhanced signal-to-noise ratio, signal profile of individual receptors, and dynamics of logical computation. The kinetic plot can be obtained by counting the receptors that produce an accurate single particle readout value As shown in FIG. 1C and FIG. 10A to FIG. 10C, an image analysis pipeline that enables integrated detection, tracking, classification, and visualization of individual nanoparticle signals is used to analyze a large number of nanoparticle logic gates.

Figure 10A:
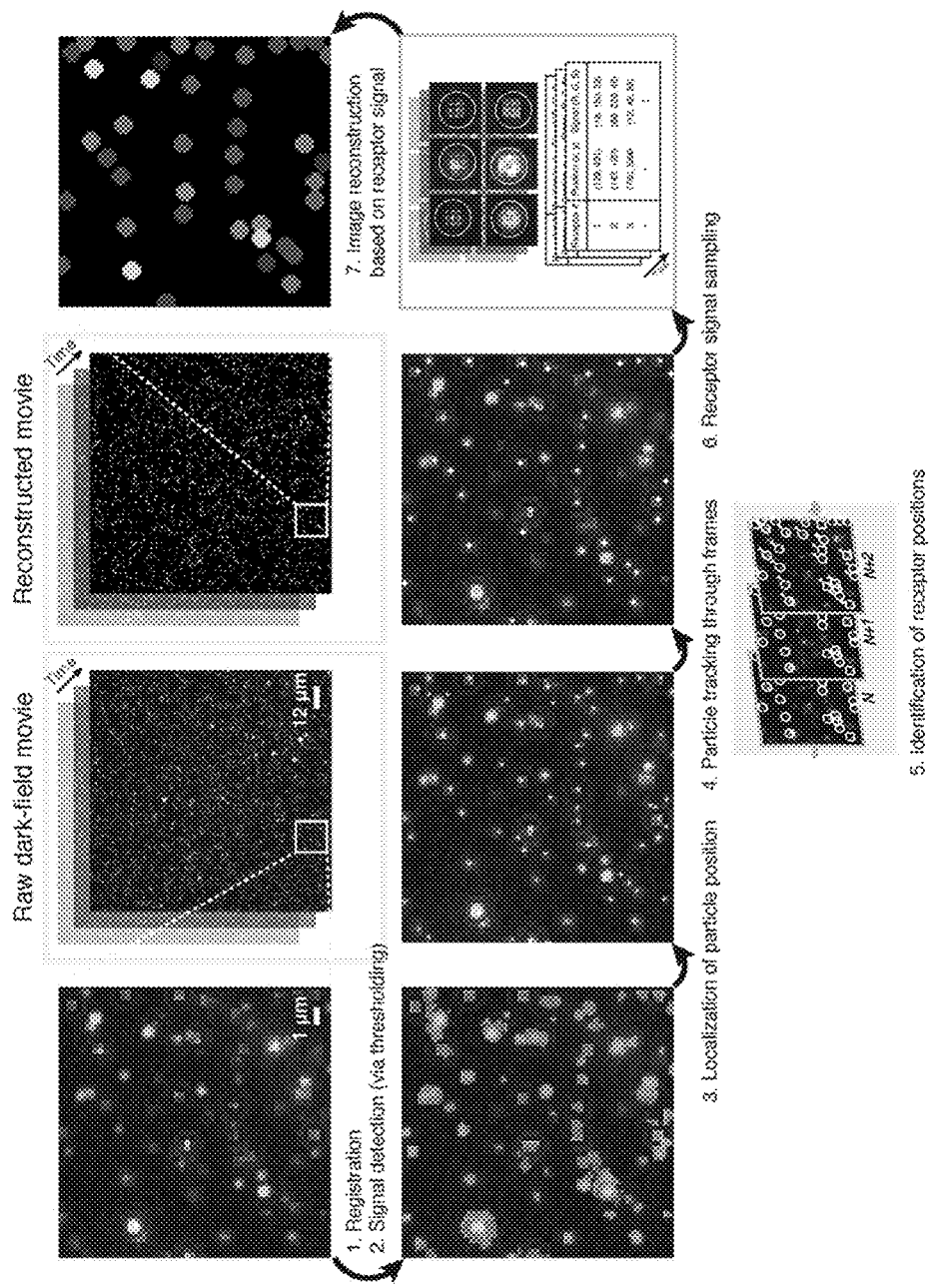
FIG. 10A to FIG. 10C show an algorithm for digital-image processing only receptors for clear and more quantitative visualization of nanoparticles of logic gates on LNT.
Figure 10B:
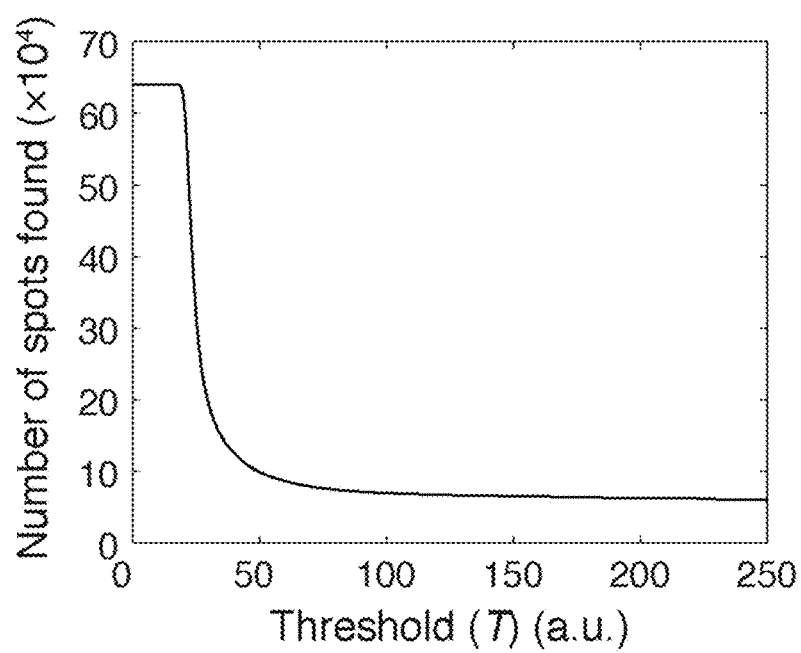
Figure 10C:
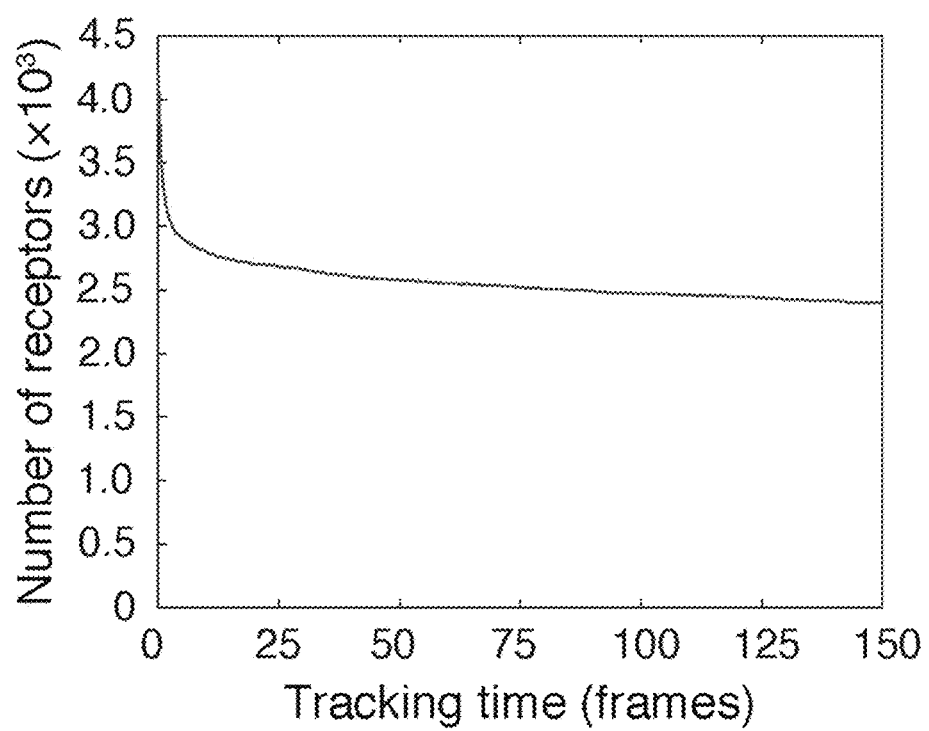

FIG. 10A to FIG. 10C show an algorithm for digital-image processing only receptors for clear and more quantitative visualization of nanoparticles of logic gates on LNT.

In FIG. 10A, computational identification of nanoparticles and receptors from time-lapse DFM data is shown. After registration (step 1), a pixel having higher signal intensity than a detection parameter is detected, and is marked with a yellow cross (step 2). A detection parameter d may vary depending on each dark-field video. This is because the type and number of nanoparticles in each tablet affect the background of the video. For example, d is defined by an equation "d=mbackground+0.5×σ background", where mbackground and σ background denote an average and a standard deviation of pixels whose gray scale intensity is less than or equal to a selected threshold value T. The boundary of the detected signal (pixel) can be easily distinguished. It is assumed that the segmented signal is from nanoparticles. The center of the segmented signal is localized to provide the nanoparticle position. Localized particles are marked with a cross (step 3). Receptors are determined by comparing local positions through frames N, N+1, and N+2 (step 4). Particles with a motionless signal are identified with a triangular dots (step 5). For each particle indicated by a triangular dot, an area for signal sampling (3×3 pixels) is set, and signals in a predetermined sampling area are sampled (step 6). Visualizing only the sampled receptor signal produces a reconstructed video with an enhanced signal-to-noise ratio (step 7).

FIG. 10B shows the number of detected signals plotted as a function of the threshold value T. The presence of a plateau shows that the number of identified signals is insensitive to the threshold value T selected for analysis.

FIG. 10C shows the number of receptors plotted as a function of a tracking frame plot. The presence of a plateau shows that the number of identified receptors is insensitive to the threshold value T selected for analysis. For example, when 70 (a.u.) is selected as the threshold value T and 31 (frames) is selected as a tracking length, receptors visually identified in the original dark-field video match those identified in the above algorithm. This comparison may show that the algorithm stably distinguishes between receptors and floaters at high density settings.

Since it is difficult to track mobile signals of floaters in the high density setting, an image analysis pipeline method exclusively trace receptors is used. Ambiguous signals that do not fall in the scatter plot categories for red, green, or blue signal clusters are eliminated for analysis. In the image analysis pipeline method, a tracking algorithm is used to reconstruct videos that visualize receptor signals only. Such videos exhibit an enhanced signal-to-noise ratio, providing a clear view of how nanoparticle circuits operate at a single-particle level in real time. First, profiling the scattering signals of R, G, and B nanoparticles is performed through the corresponding analysis method, and the profile is used for signal classification.

Figure 11A:
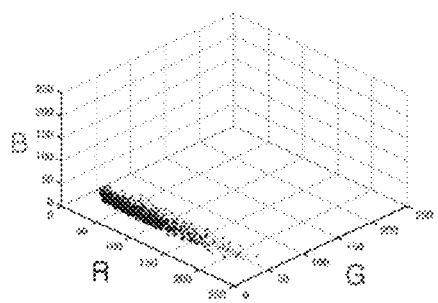
FIG. 11A to FIG. 11C show scattering signal profiles of R, G, and B nanoparticles.
Figure 11A:
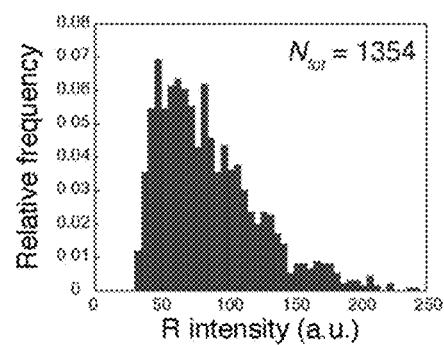
Figure 11A:
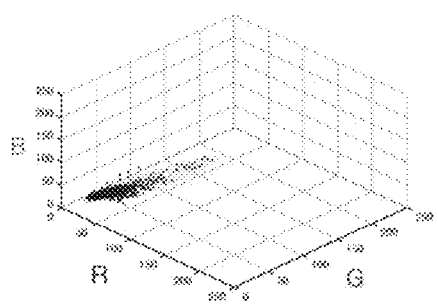
Figure 11A:
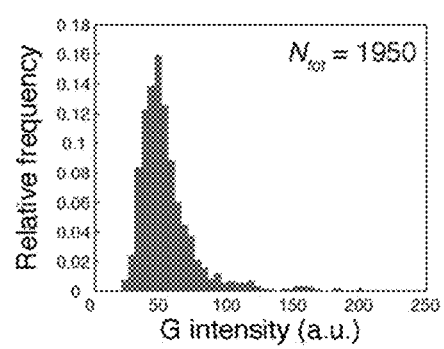
Figure 11A:
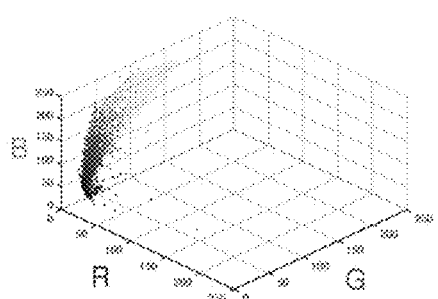
Figure 11A:
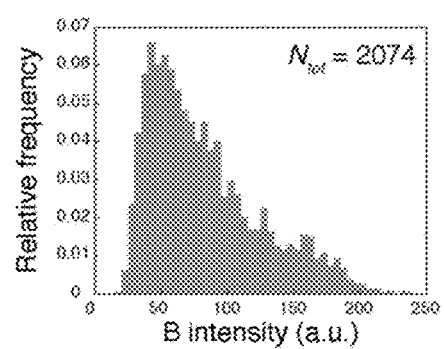
Figure 11B:
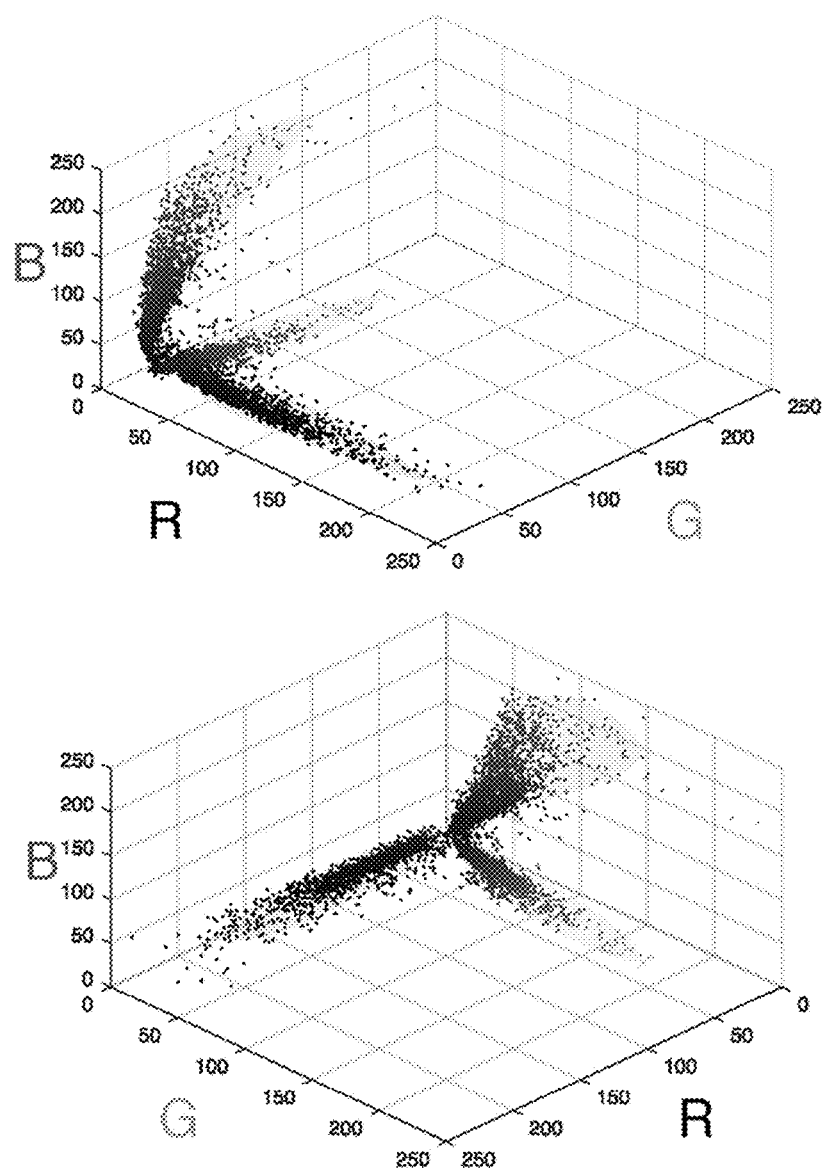
Figure 11C:
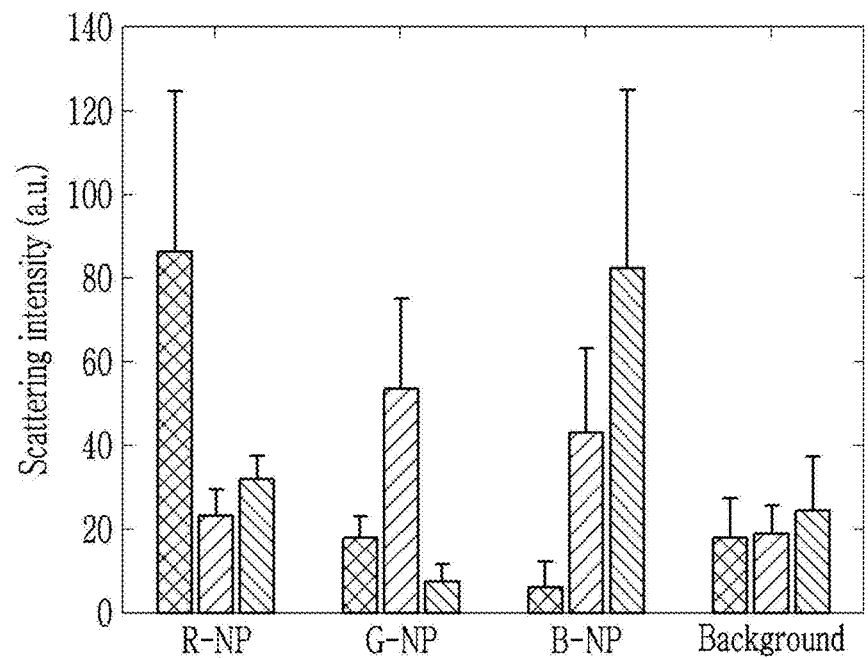

FIG. 11A to FIG. 11C show scattering signal profiles of R, G, and B nanoparticles.

In FIG. 11A and FIG. 11B, each cluster is displayed with a corresponding color, and thus clusters for each color are easily distinguished. In FIG. 11A, RGB intensity scatter plots for R nanoparticles (top), G nanoparticles (middle), and B nanoparticles (bottom) are illustrated in the 3D signal space. In FIG. 11B, two perspective views where the R, G, and B clusters are shown together in the 3D signal space is illustrated. The two perspective views are divided according to the perspective of viewing the 3D signal space.

In FIG. 11C, averages of the red, green, and blue scattering intensities for each of the R, G, and B nanoparticles and background signals are displayed as bars. As shown in FIG. 11C, bars marked by "/" denote green, bars marked by "\" denote blue, and bars marked by "X" denote red. Error bars represent standard deviation. Signal profiling of nanoparticle monomers may be used to confirm and classify logic-gated nanoparticle reaction in the lipid nanotablets.

FIG. 12A to 12D show a two-input nanoparticle logic gate on LNT.

Referring to FIG. 12A to 12D, an Assembly AND, an Assembly OR, a Disassembly AND, and a Disassembly OR gate will be described. To constructs these gates, the DNA bonds are programmed in receptor-floater interfaces in such a way that the bonds are formed via assembly or cleaved via disassembly only when two different DNA inputs satisfy AND or OR logic. Such an approach is called interface programming.

DNA sequences and experiment conditions for the two input nanoparticle logic gates are summarized in Table 3 and Table 14.

Figure 13:
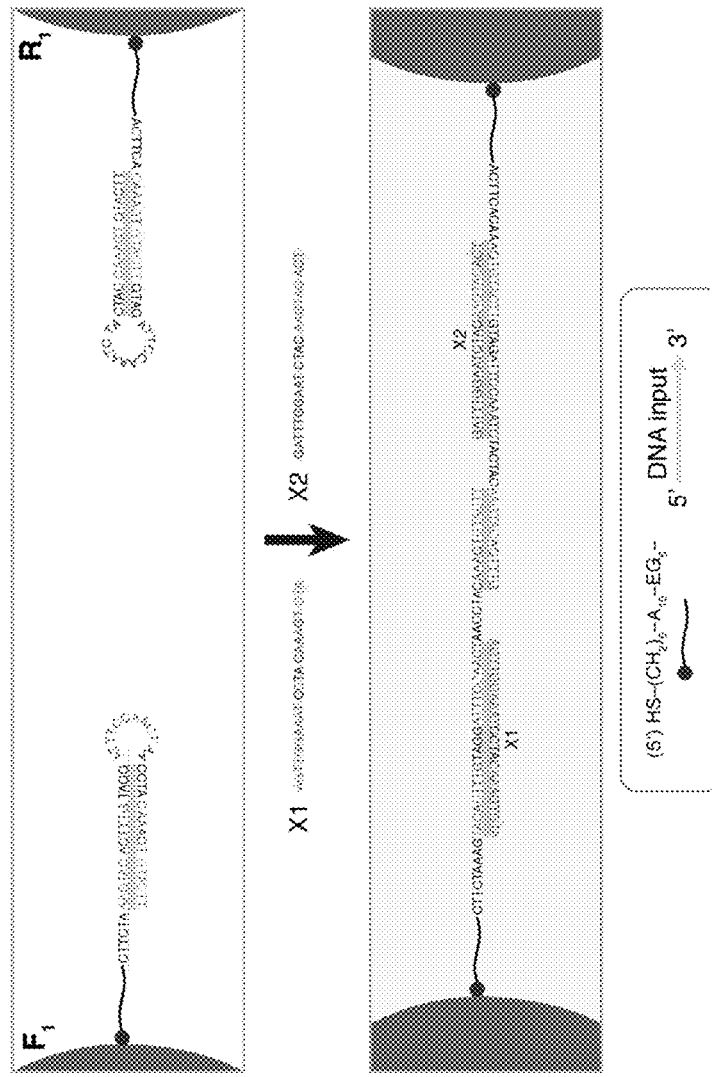
FIG. 13 shows operating principles of the two-input Assembly gate and DNA sequences.

FIG. 13 shows operating principles of the two-input Assembly gate and DNA sequences.

In FIG. 13, sequencing level figures are illustrated for description of a method for the Assembly AND gate to respond to two inputs X1 and X2. EG indicate an ethylene glycol unit.

Figure 12A:
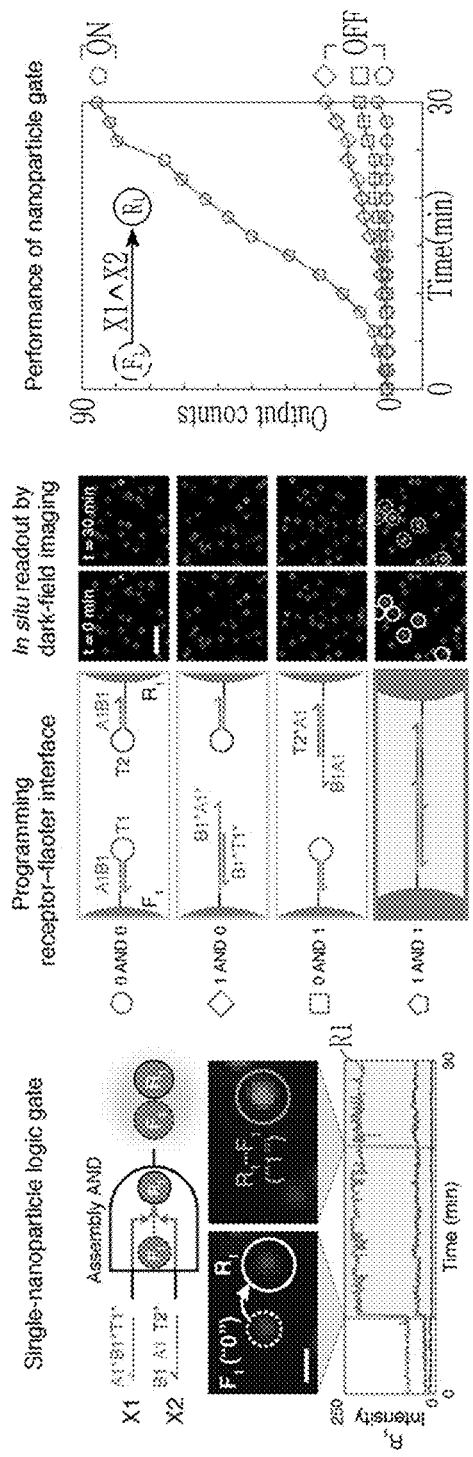
FIG. 12A to 12D show a two-input nanoparticle logic gate on LNT.

As shown in FIG. 12A and FIG. 13, in the Assembly AND gate, conformation-switchable DNA hairpins may be used as surface ligands. G-NR ($R_1$) is modified with a DNA hairpin T2, G-NF ($F_1$) is modified with a DNA hairpin T1, and each of the DNA hair pins hides its binding domain (B1A1 and A1*B1*) in the stem. Through hybridization with input strands X1 and X2 on their loop, hairpins are opened, the binding domain B1A1 of the G-NR ($R_1$) and the binding domain A1*B1* of the G-NF ($F_2$) are exposed, and G-NR ($R_1$) and G-NF ($F_2$) are assembled through hybridization between the two binding domains. That is, the receptor $R_1$ and the floater $F_1$ are assembled only if X1 and X2 are both present in the solution. In the graph of FIG. 12A, an increase of intensity of $R_1$ due to assembly is illustrated.

Figure 14:
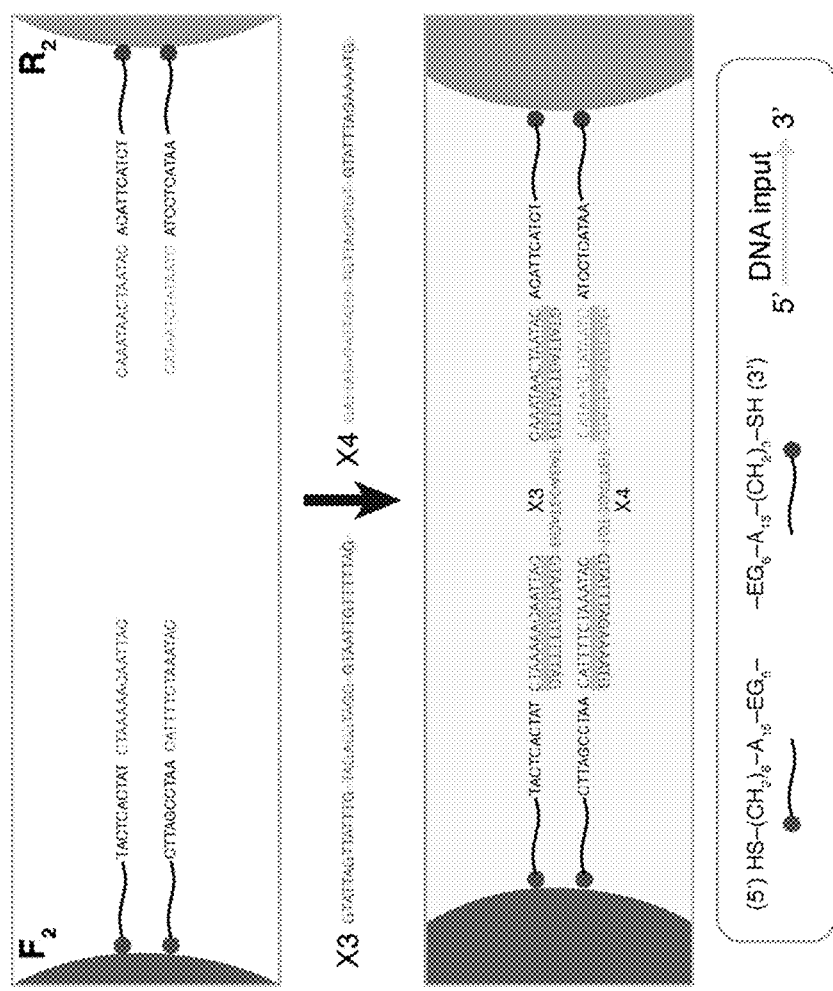
FIG. 14 shows operating principles of the two-input Assembly OR gate and DNA sequences.

FIG. 14 shows operating principles of the two-input Assembly OR gate and DNA sequences.

In FIG. 14, sequencing level figures are illustrated for description of a method for the Assembly OR gate to respond to two inputs X3 and X4. EG indicate an ethylene glycol unit.

Figure 12B:
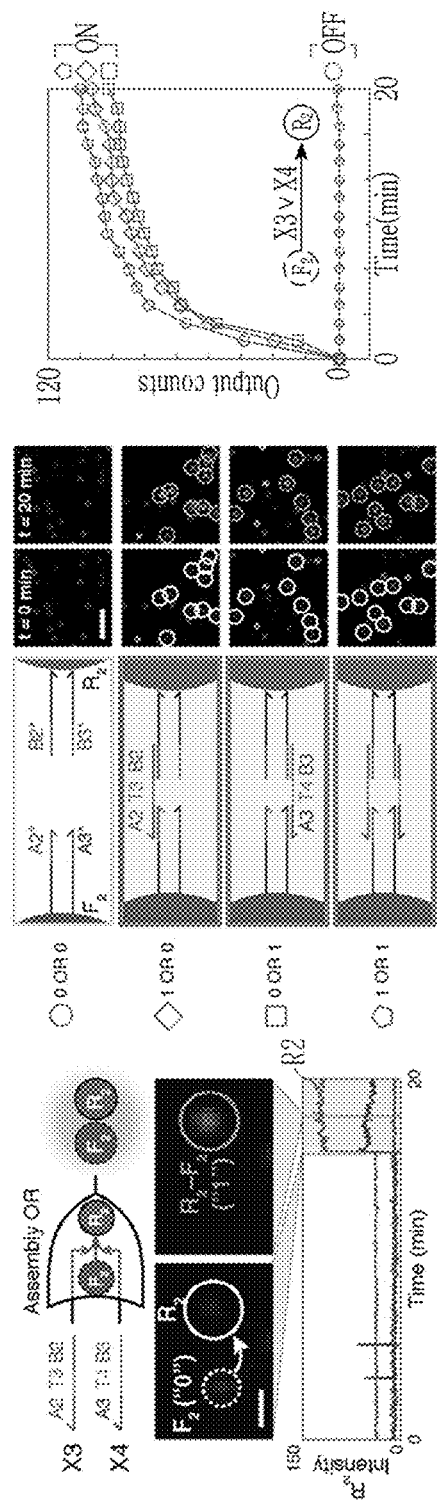

As shown in FIG. 12B and FIG. 14, in the Assembly OR gate, a G-NR $R_2$ is modified with two types of DNA ligands (B2* and B3*), and a B-NF $F_2$ is modified with two types of DNA ligands (A2* and A3*). Each DNA ligand exposes a distinct binding domain. Either input X3 or X4 can hybridize with the half-complementary domain on $F_2$ and $R_2$, resulting in dimerization. In the graph of FIG. 12B, increase of $R_2$ intensity due to binding is illustrated.

Figure 15:
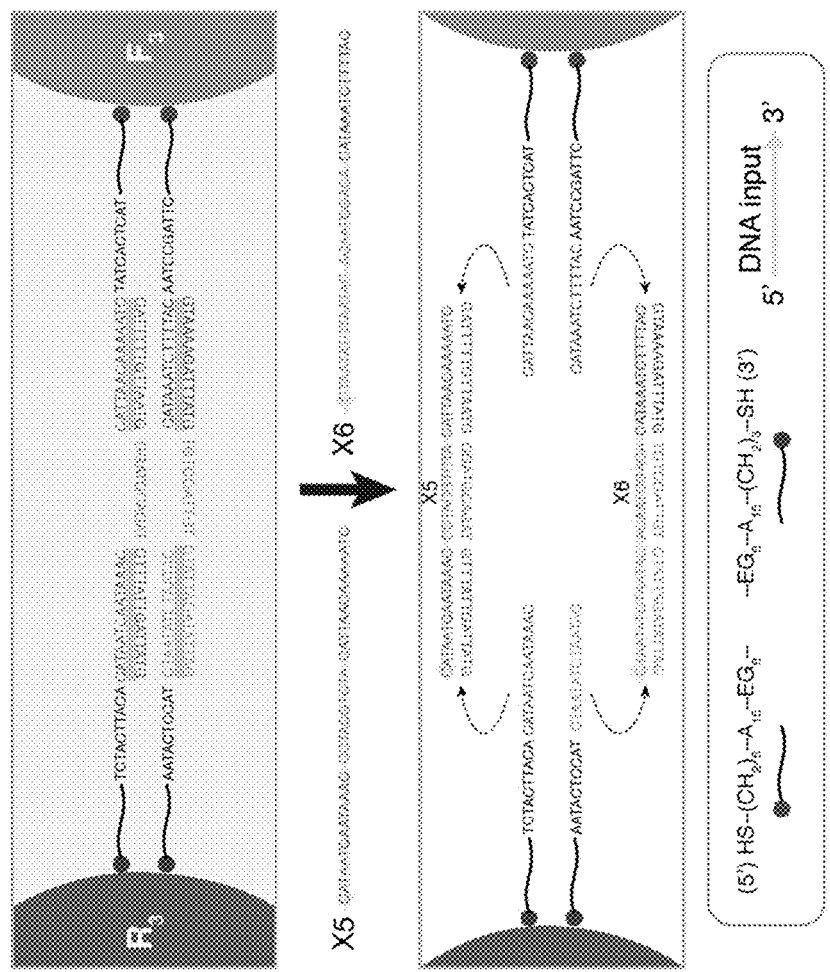
FIG. 15 shows operating principles of the two-input Disassembly AND gate and DNA sequences.

FIG. 15 shows operating principles of the two-input Disassembly AND gate and DNA sequences.

In FIG. 15, sequencing level figures are illustrated for description of a method for the Disassembly AND gate to respond to two inputs X5 and X6. EG indicate an ethylene glycol unit.

Figure 12C:
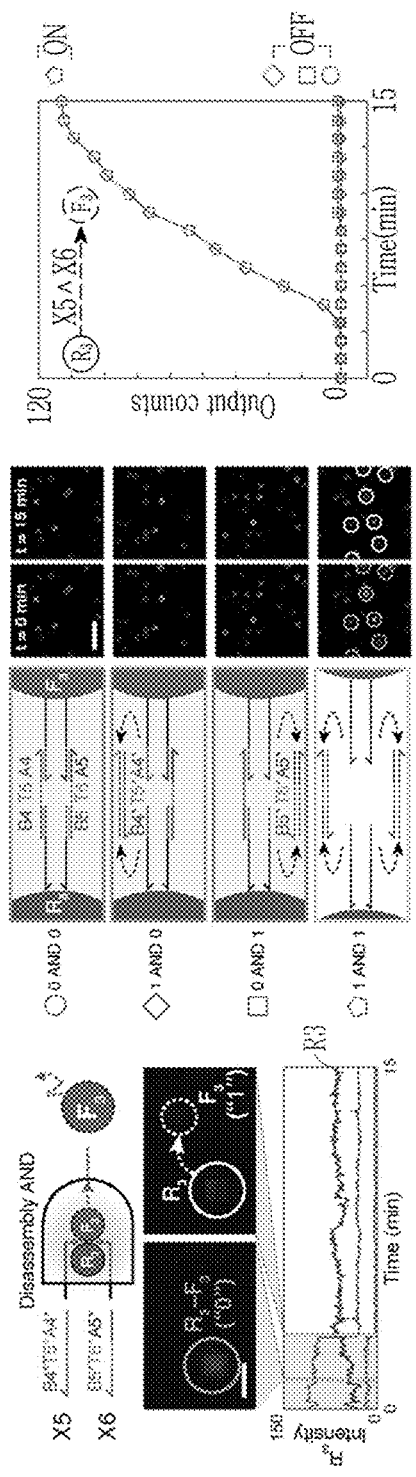

As shown in FIG. 12C and FIG. 15, in the Disassembly AND gate, a G-NF $F_3$ is bound to a B-NR $R_3$ by two different DNA bonds, each of which exposes a toehold domain (T5 and T6) within an interface between particles. The two toehold domains act as recognition regions, recruiting input strands X5 and X6, and each removes a DNA bond via strand displacement. The disassembly reaction is initiated when the two different DNA bonds are removed by X5 and X6. In the graph of FIG. 12C, an increase in $R_3$ intensity due to disassembly is shown.

Figure 16:
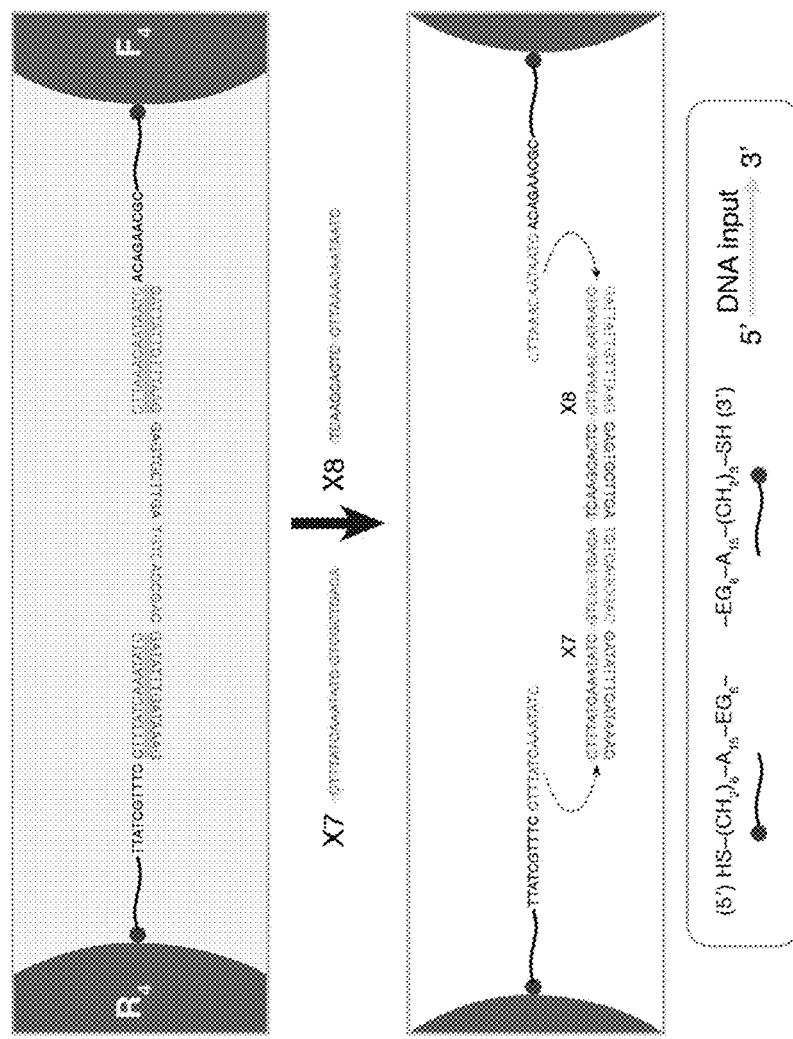
FIG. 16 shows operating principles of the two input OR gate and DNA sequences.

FIG. 16 shows operating principles of the two input OR gate and DNA sequences.

In FIG. 16, sequencing level figures are illustrated for description of a method for the Disassembly OR gate to respond to two inputs X7 and X8. EG indicate an ethylene glycol unit.

Figure 12D:
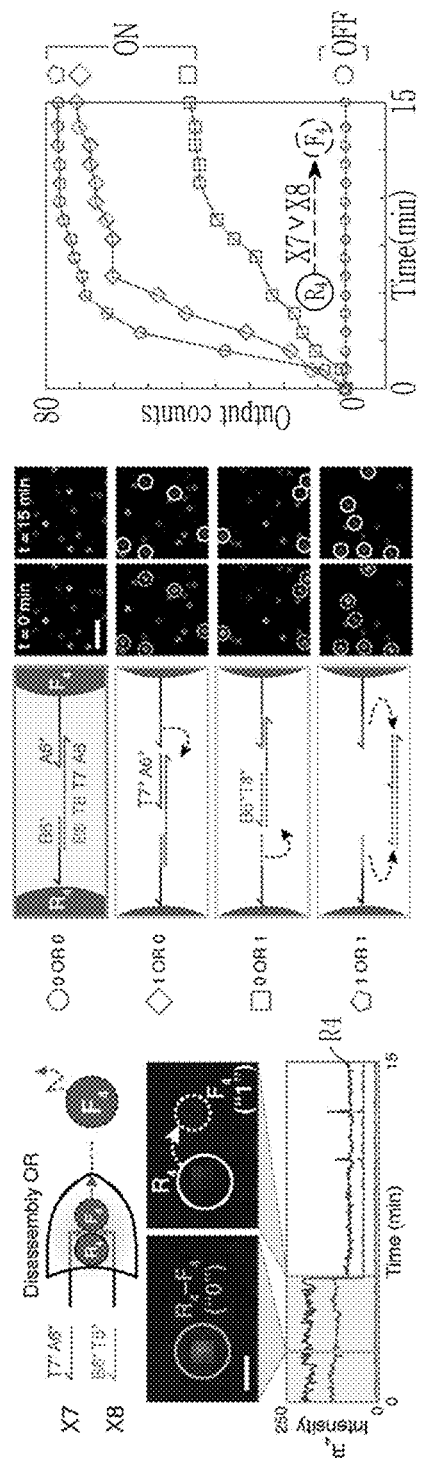

As shown in FIG. 12D and FIG. 16, in the disassembly OR gate, a B-NF $F_4$ is bound to a B-NR $R_4$ via one type of DNA bond that exposes two toehold domains T7 and T8 in the interface. One of the two toehold domains can independently recruit an input strand. Sequence domains of each of the input strands X7 and X8 are half-complementary to the existing DNA bond. For example, a sequence domain "T7*A6*" of the input strand X7 is half-complementary to the DNA bond "B6T8T7A6", and a sequence domain "B6*T8*" of the input strand X8 is half-complementary to the DNA bond "B6T8T7A6". The input strands X7 and X8 cleave the bond through strand displacement with the ligand (by X8) on B-NR $R_4$ or strand displacement with the ligand (by X7) on B-NF $F_4$. In the graph of FIG. 12D, a decrease in $R_4$ intensity due to disassembly is illustrated.

The design principles for the interface programming are schematically generalized and are illustrated in FIG. 17A to FIG. 17F.

FIG. 17A to FIG. 17F show design principles of nanoparticle logic gates.

Figure 17A:
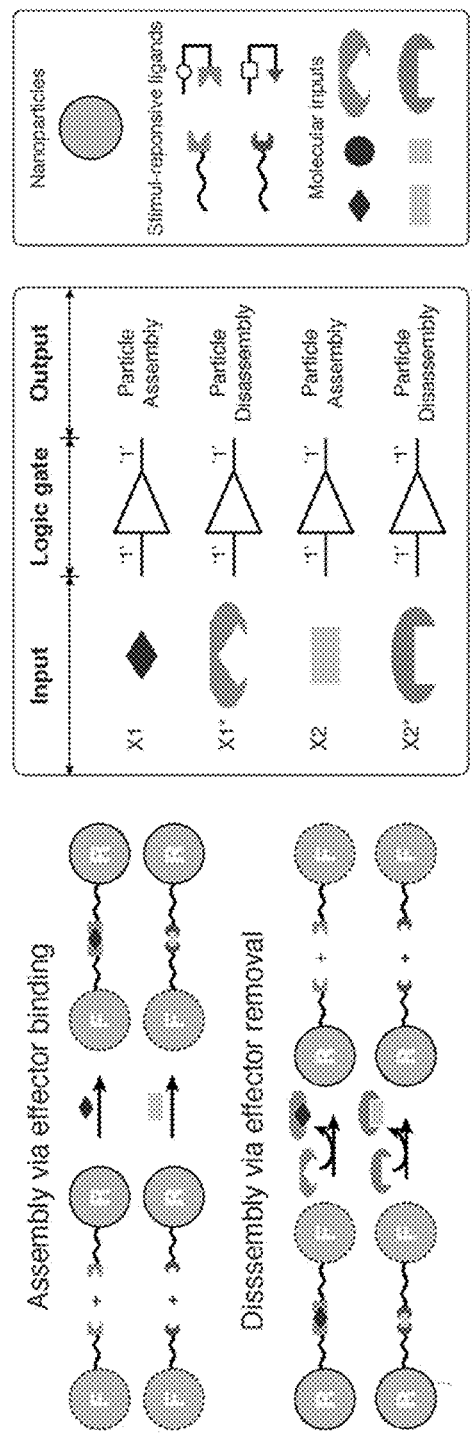

In FIG. 17A, a graphical summary of the generalization concept is shown. Assembly/Disassembly of YES gates (left) of effector-mediated nanoparticles and a truth table (right) for the concept are shown. A selective effector-ligand pair and an effector-chelator pair are required for configuration of the Assembly/Disassembly logic gates. To construct a logic gate by using two nanoparticles, bond interaction needs to be programmed in receptor-floater interfaces in such a way that the bonds are formed via assembly or cleaved via disassembly only when two molecular inputs satisfy AND or OR logic.

Figure 17B:
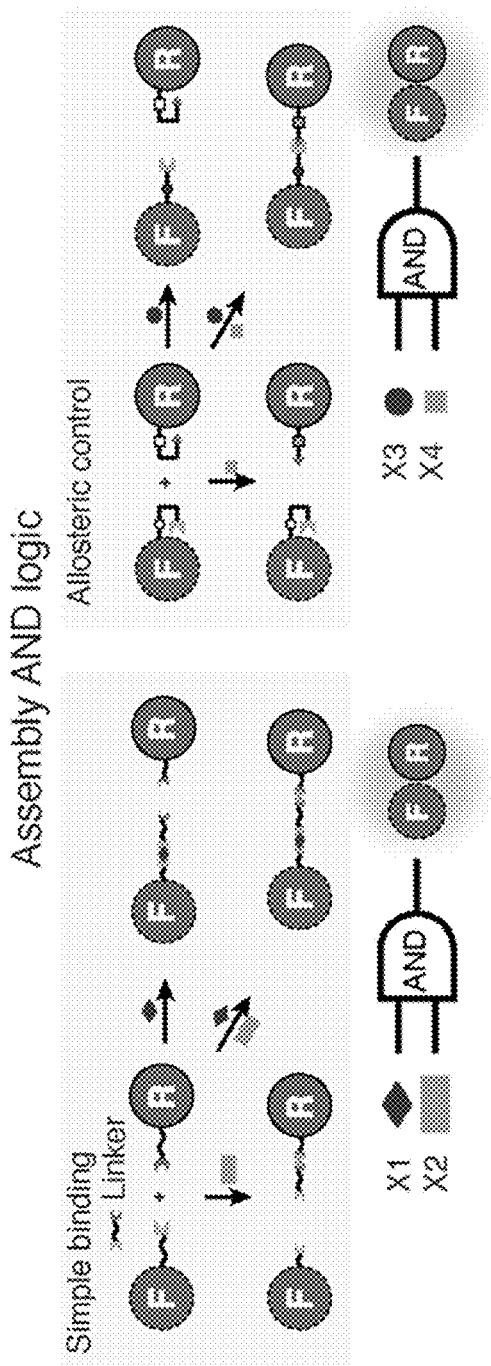
Figure 17C:
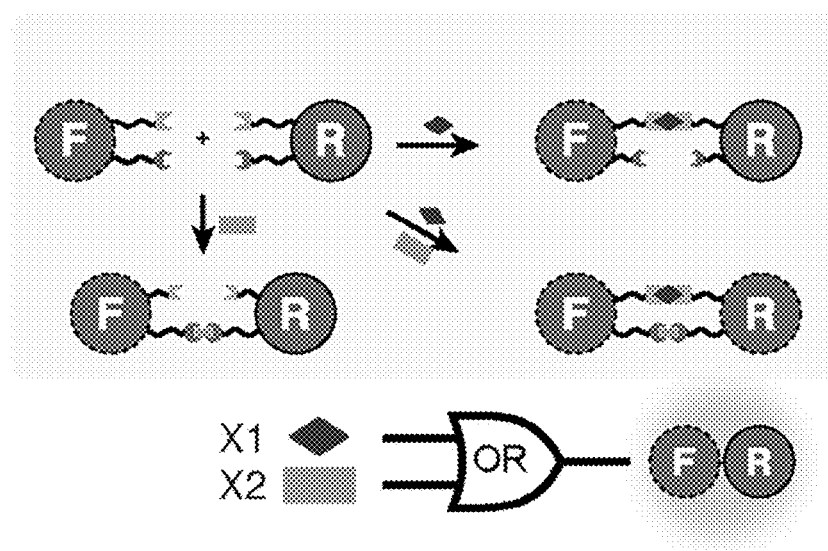

FIG. 17B shows designing of an Assembly AND gate. FIG. 17C shows designing of an Assembly OR gate.

The assembly reaction is controlled by AND logic when bond-forming interactions require serial activation by two inputs, and by OR logic when bond-forming interactions are controlled in parallel.

Figure 17D:
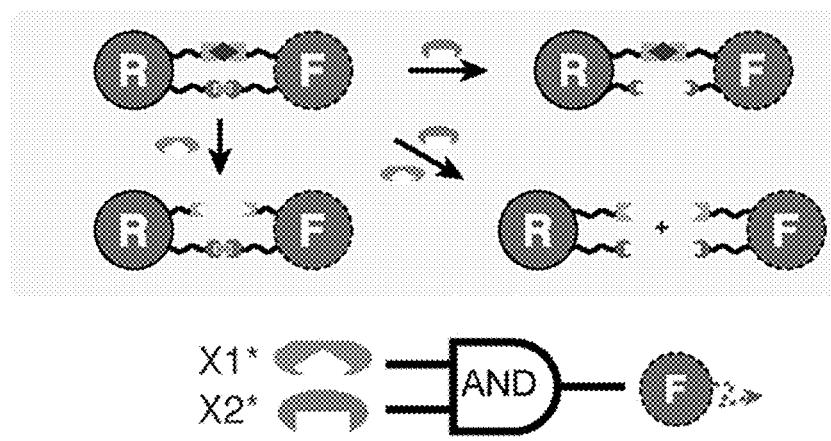
Figure 17E:
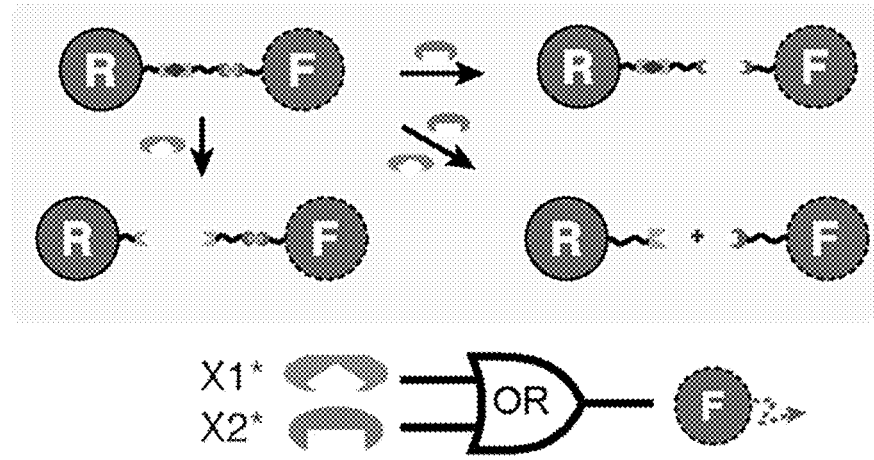

FIG. 17D shows designing of a Disassembly AND gate. FIG. 17E shows designing of a Disassembly OR gate.

The disassembly reaction is controlled by AND logic through a parallel disconnection paradigm and OR logic through a serial disconnection design.

FIG. 17F shows a generalization concept of interface programming. Sequence recognition and strand displacement of DNA are used as mechanisms to implement logic. Specifically, a single-stranded DNA molecule as an effector, thiol oligonucleotides as a ligand, and strand displacement as a chelation mechanism are used. The simplicity of design makes it possible to design a sequence with several constraints. Such a simple design rule can be applied to other ligand systems and core nanostructures.

The performances of the nanoparticle gates can be analyzed by counting output responses of the nanoparticle gates captured in dark-field videos. Whether or not a type of nanoparticle gate generates accurate digital output can be determined through a quantification process.

All four logic gates generated low output counts under the logical FALSE conditions and high output counts under the TRUE conditions. Specifically, ON/OFF levels over 5 folds, 88 folds, 93 folds, and 42 folds with fast response kinetics (t½<19 min, t½<5 min, t½<9 min, and t½<5 min) for the Assembly AND gate, the Assembly OR gate, the Disassembly AND gate, and Disassembly OR gate are provided, respectively.

The ON/OFF levels are evaluated by dividing the lowest output count obtained in the TRUE conditions by the highest output count obtained in the FALSE conditions. In Table 1, the response rate (%) (the number of floaters that react to inputs divided by the total number of floaters) is typically about 80% in the TRUE conditions.

TABLE 1

| Logic Circuit | Input condition | | | |
| --- | --- | --- | --- | --- |
| | 00 | 01 | 10 | 11 |
| Two-input Assembly AND gate | 2.80 | 7.78 | 17.74 | 84.31 |
| Two-input Assembly OR gate | 0.817 | 76.90 | 71.66 | 79.22 |

TABLE 1-continued

| Logic Circuit | Input condition | | | |
|---|---|---|---|---|
| | 00 | 01 | 10 | 11 |
| Two-input Disassembly AND gate | 0 | 0.90 | 0 | 83.46 |
| Two-input Disassembly OR gate | 0 | 42.35 | 74.24 | 79.00 |

The response rate, defined as the number of the floaters that reacted to the inputs divided by the total number of the floaters counted in the initial state, is typically over 80%. The Assembly AND gate exhibits minor output leaks at 1 AND 0 and 0 AND 1, presumably because the surface hairpins are in dynamic equilibrium between closed and opened states.

Figure 18A:
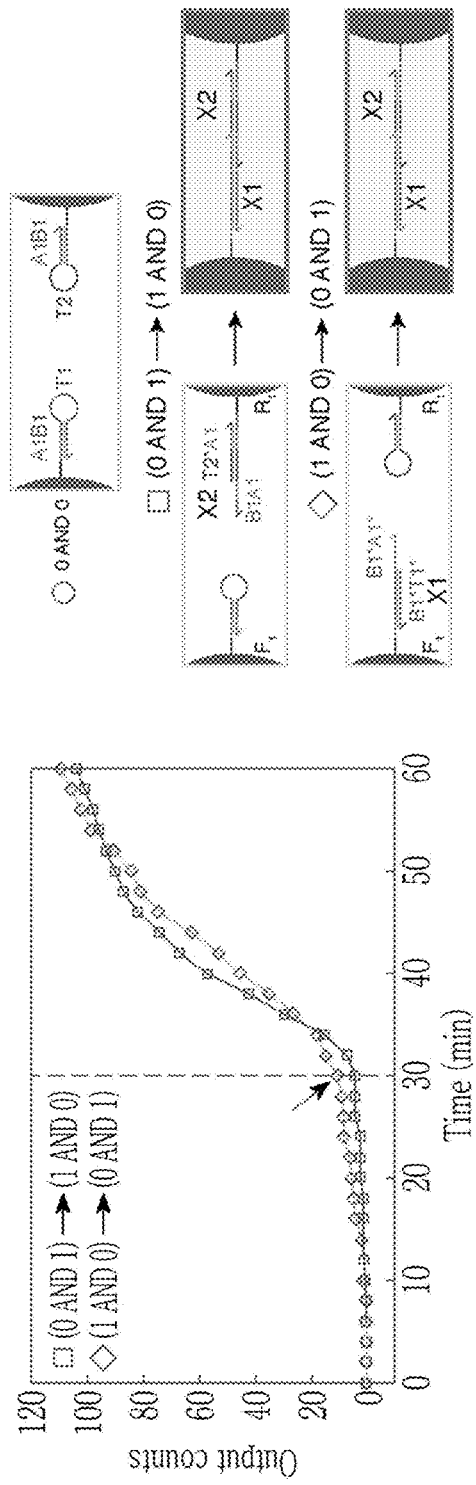
FIG. 18A to FIG. 18C show modularity in two hairpin-based input Assembly AND gates.
Figure 18B:
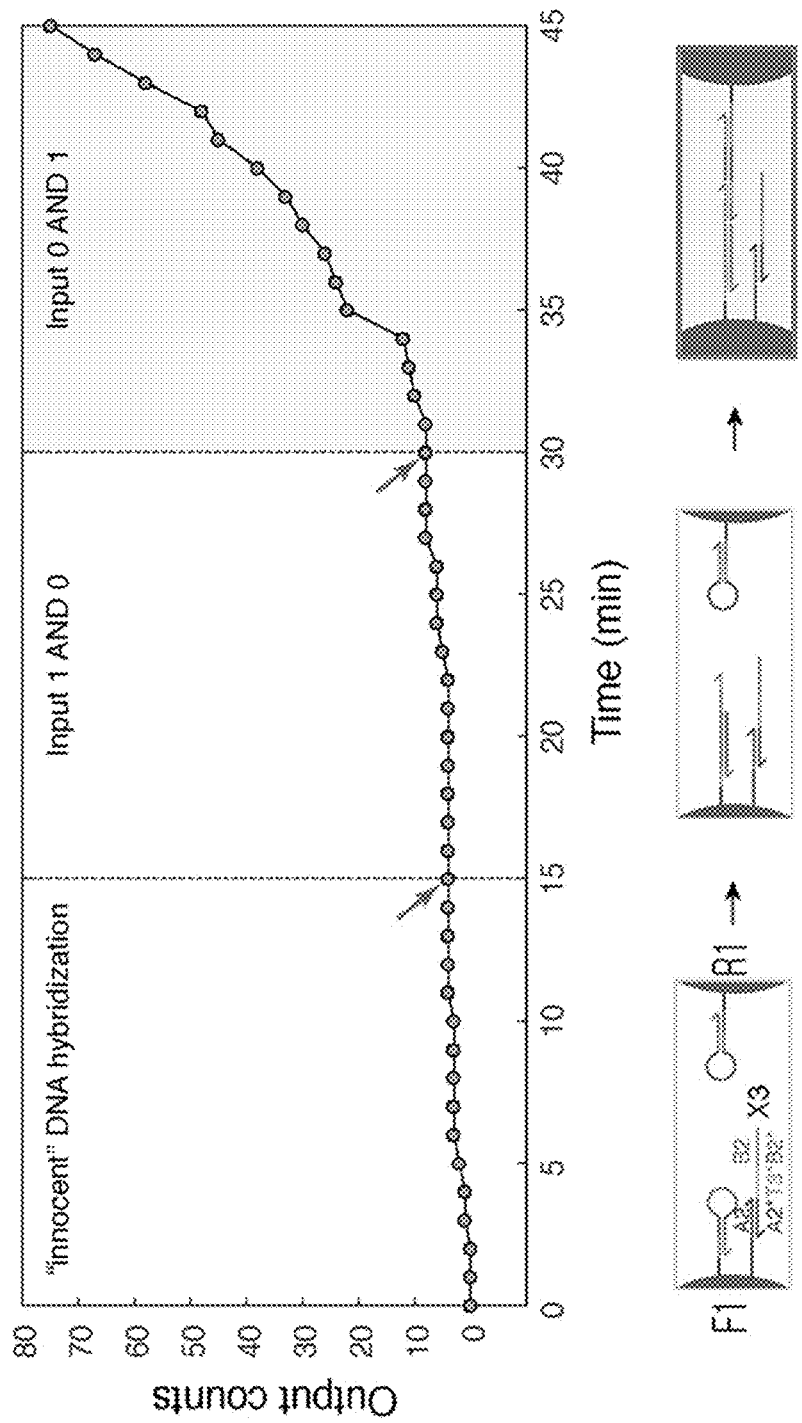
Figure 18C:
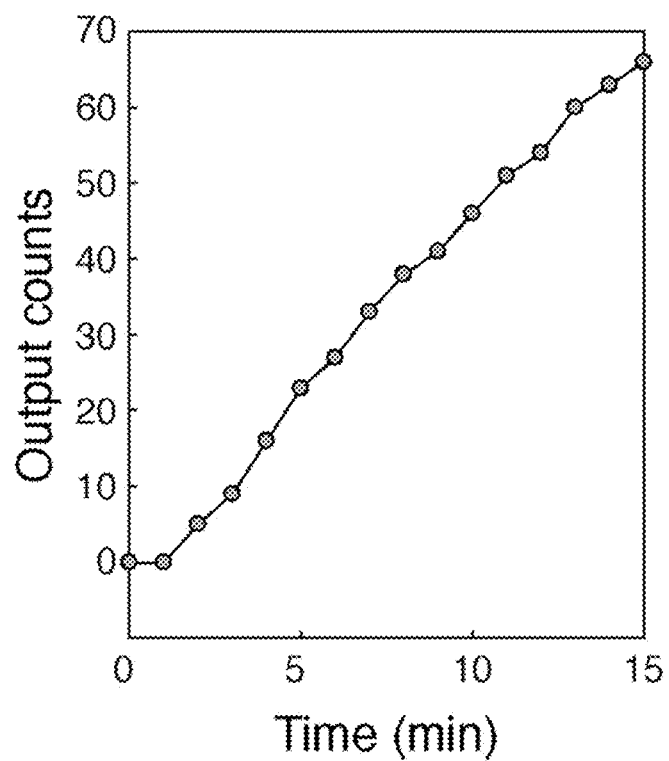
Figure 18C:
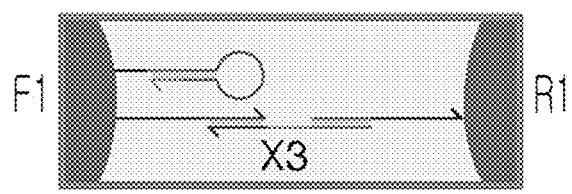

FIG. 18A to FIG. 18C show modularity in two hairpin-based input Assembly AND gates.

As shown in FIG. 18A, the hairpin-based AND assembly process is controlled by input-induced hairpin opening.

As shown in FIG. 18B, the hairpin-based assembly process occurs without interfering with other hybridization events.

In FIG. 18A, the Assembly AND gates are sequentially activated with respect to sequentially introduced inputs, resulting in generation of responses of the Assembly AND gates. In FIG. 18A, □ denotes a case that X1 is added in succession of addition of X2, and ◇ denotes a case that X2 is added after X1 is added. As shown in FIG. 18A, two hybridization events are both required to induce nanoparticle assembly.

In FIG. 18B, the Assembly AND gate operating after hybridization by DNA input X3 that interacts with a non-hairpin ligand is illustrated. As shown in FIG. 18B, the hairpin-based assembly is not sensitive to other hybridization events in the same particle.

In FIG. 18C, assembly by normal DNA input X3 is illustrated. As shown in FIG. 18C, assembly by simple hybridization (as in the Assembly OR gate) is not sensitive to existence of the hairpin ligand in the same particle. The DNA sequence and experiment conditions are summarized in Tables 7, 8, and 18.

Figure 19:
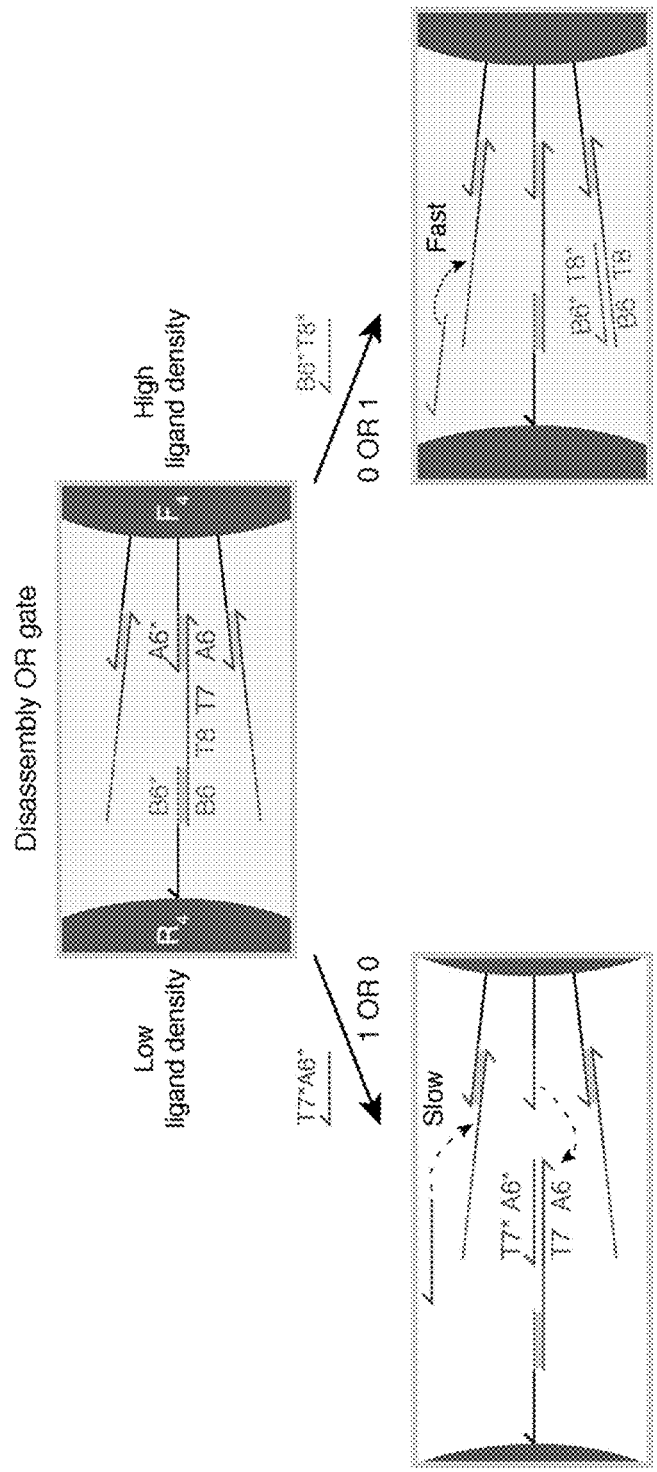
FIG. 19 shows uneven responses of two input disassembly OR gates.

FIG. 19 shows uneven responses of two input disassembly OR gates.

As shown in FIG. 19, the disassembly OR gate exhibits uneven responses, where TRUE output under the 0 OR 1 condition results in a fraction of 57% of other TRUE outputs in other input conditions. This result occurs due to a difference in density of surface ligands between receptors and floaters.

In FIG. 19, a response rate in the 1 OR 0 condition may be higher than a response rate in the 0 OR 1 condition because the density of surface ligands is higher in $F_4$ than in $R_4$. Due to the high ligand density, $F_4$ exposes more single-stranded domains (B6-T8-T7) than $R_4$. The exposed strand may interact with the incoming input strand. An interaction between an input B6*-T8* and an exposed bond in the 0 OR 1 condition is more effective than an interaction between an input A6*-T7* and a bond in the 1 OR 0 condition. This is because the recognizable sequence is longer and more accessible to previous interactions. As a result, the inputs B6*-T8* are more easily trapped by the exposed strands, without causing effective strand displacement that induces particle disassembly.

Additionally, the LNT system is compatible with a "dual-rail" convention, where the Boolean values of a logic gate are represented by the presence of either one signal ("0") or another ("1"). This formalism is used for systems where it is difficult to define the NOT function. With this representation, AND and OR gates are sufficient to compute any Boolean function.

Figure 20A:
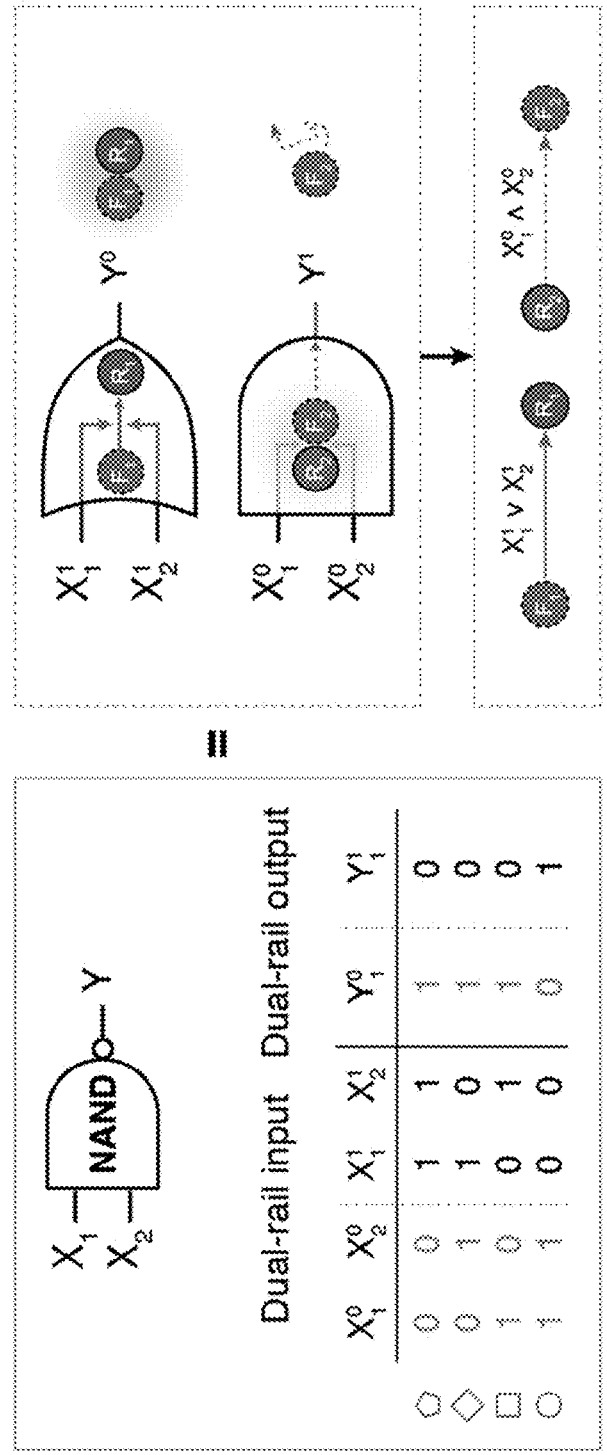
FIG. 20A to FIG. 20B show a dual-rail of a NAND gate.
Figure 20B:
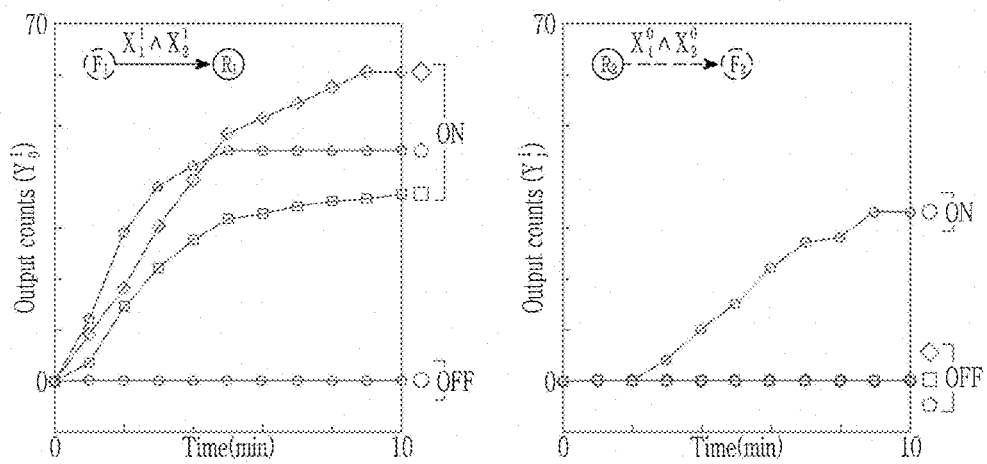

FIG. 20A to FIG. 20B show a dual-rail of a NAND gate.

In FIG. 20A, two input dual rail NAND gates are illustrated. Dual-rail inputs of Xi are marked with $x_i^0$ and $x_i^1$ (respectively denoting logic OFF and logic ON), and outputs are also marked with the same rule. A two-input Assembly OR gate ($x_1^1$ OR $x_2^1$) and a two-input Disassembly AND gate ($x_1^0$ AND $x_2^0$) are implemented in parallel to process dual-rail NAND logic.

FIG. 20B illustrates dark-field kinetic experiment results. Two gates generate accurate logic outputs while providing an ON/OFF level of over 37 folds ($Y^0$, 2 input Assembly OR) and 33 folds ($Y^1$, 2 input Disassembly AND) without interfering with each other. This result may prove modularity of the nanoparticle logic gate. DNA sequence and experimental conditions are summarized in Table 9 and Table 19.

Interface programming may be expanded to enable nanoparticle logic gates to process INHIBIT logic (X1 AND NOT X2), and generate multiple outputs (fan-out) with multiple inputs (fan-in).

Figure 21A:
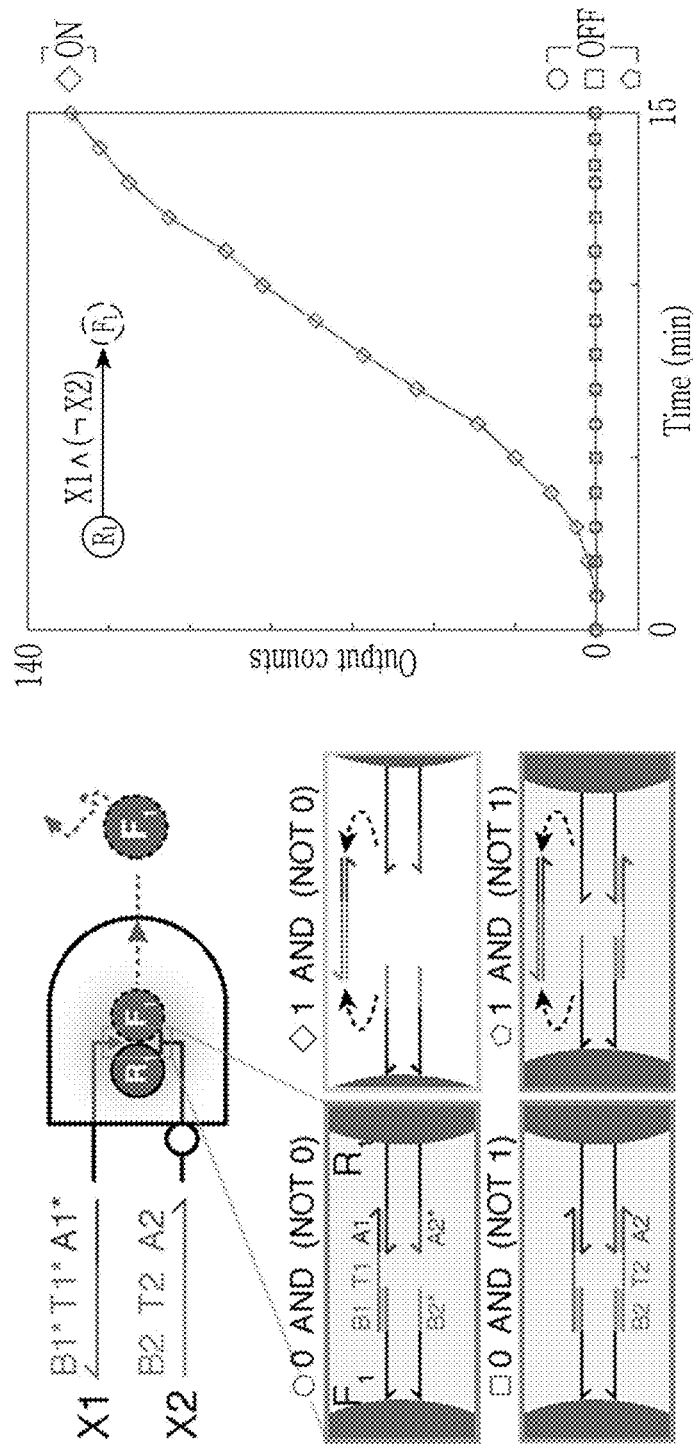
FIG. 21A to FIG. 21C show nanoparticle logic gates processing INHIBIT operations and having multiple inputs (fan-in) and multiple outputs (fan-out).
Figure 21B:
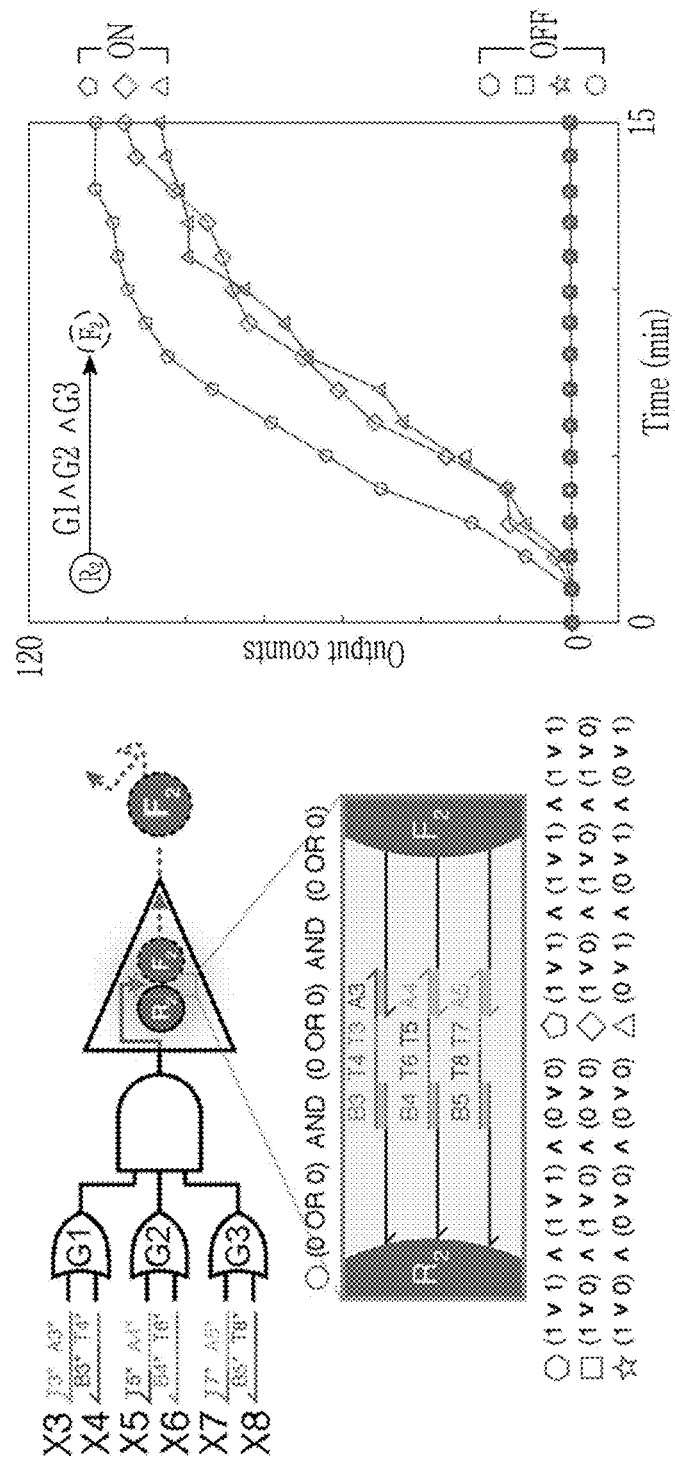
Figure 21C:
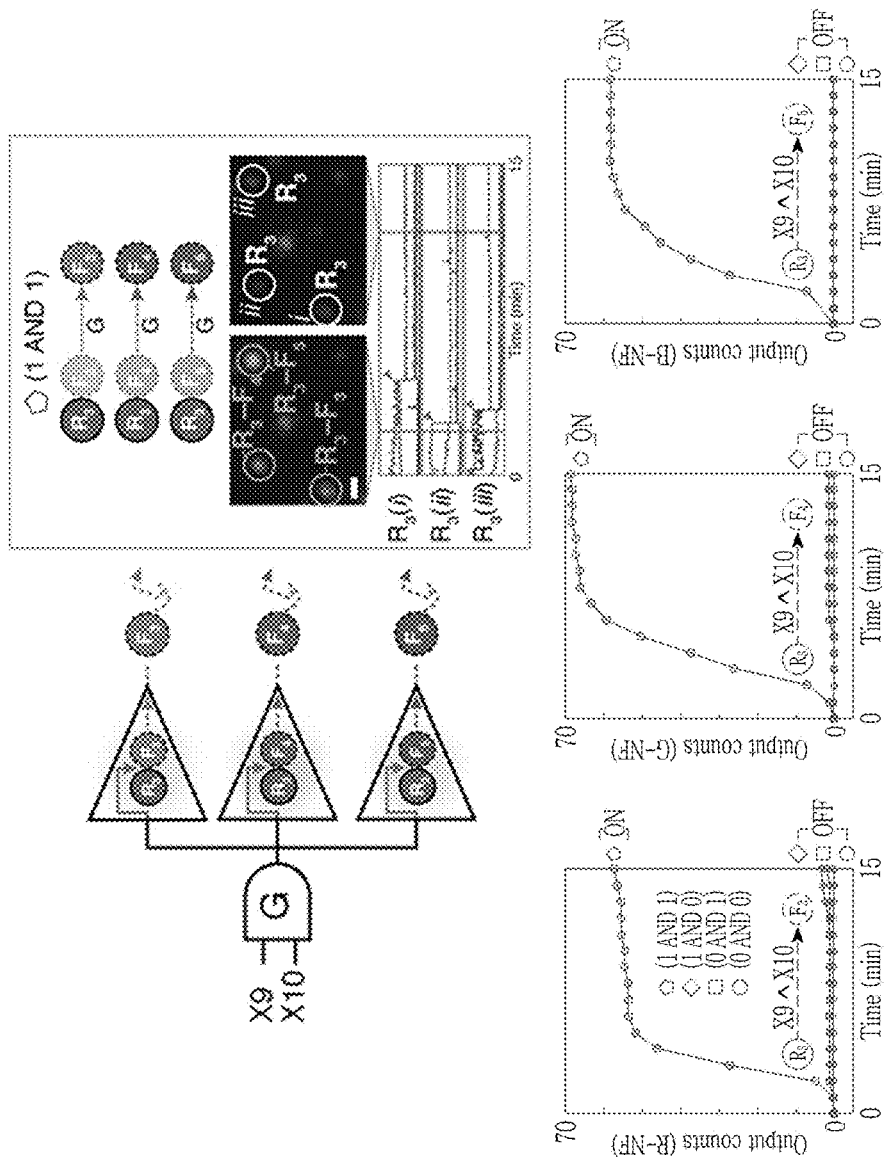

FIG. 21A to FIG. 21C show nanoparticle logic gates processing INHIBIT operations and having multiple inputs (fan-in) and multiple outputs (fan-out).

In FIG. 21A to FIG. 21C, $\wedge$, $\vee$, and $\neg$ respectively denote logic symbols with respect to AND, OR, and NOT. Each plot contains a reaction graph that corresponds to each gate. DNA sequence and experimental conditions are summarized in Tables 4-1, 4-2, and 15. Experiments are carried out at 25° C. in a 1× PBS buffer solution.

First, in FIG. 21A, a two-input Disassembly INHIBIT gate implemented in $R_1$-$F_1$ is illustrated. To achieve the logic function, the ligands for Assembly YES and Disassembly YES gates are simultaneously used to control the disassembly between a G-NR ($R_1$) and a G-NF ($F_1$). The assembly input X2 is used to form other DNA bonding, but the disassembly input X1 is used to remove existing DNA bonding.

In the two-input Disassembly INHIBIT gate shown in FIG. 21A, the NOT logic required for the INHIBIT gate can be implemented through competition between DNA bond removal triggered by X1, and DNA bond formation triggered by X2. The INHIBIT gate releases $F_1$ as an output if and only if the assembly input X1 is present and the assembly input X2 is absent.

Figure 22A:
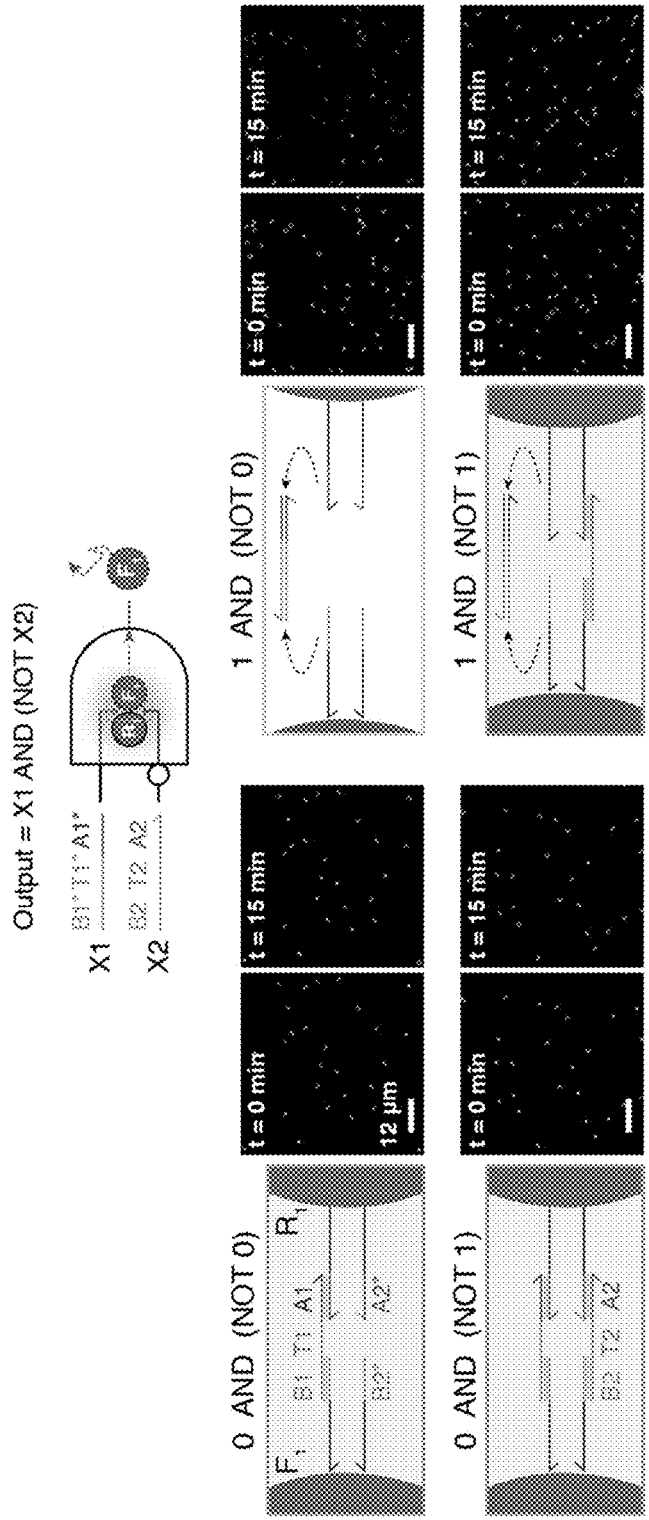
FIG. 22A to FIG. 22B show the operation of the two-input Disassembly INHIBIT gate.
Figure 22B:
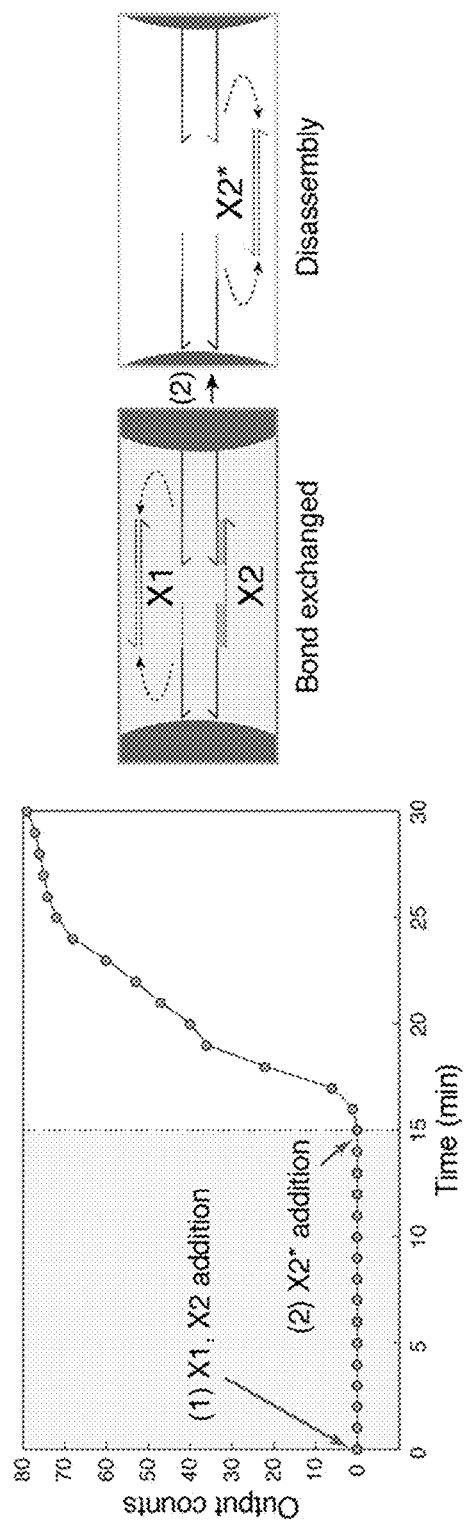

FIG. 22A to FIG. 22B show the operation of the two-input Disassembly INHIBIT gate.

In FIG. 22A, domain-level figures and a reconstructed dark-field image of operation of a two-input Disassembly INHIBIT gate are illustrated. The reconstructed image provides only a receptor signal. A Disassembly reaction is observed only in a state of logic 1 AND (NOT 0).

As shown in FIG. 22A, the INHIBIT gate generates an output count only in the TRUE state with an ON/OFF level of over 129 folds. No output leakage was observed when both inputs were present, indicating that the bond formation was faster by X2 than the bond removal by X1.

As shown in FIG. 22B, two competing reactions proceed without interfering with each other.

FIG. 22B illustrates characteristics of a strand displacement reaction in the INHIBIT gate. According to such a design, bonding of the gates is changed to B2-T2-A2 X2 from B1-T1-A1 when adding two inputs X1 and X2. Conformation-switch is valid in the receptor-floater interface, and the disassembly reaction should take place upon subsequent addition of X2*. The dark-field kinetics plot shows that the INHIBIT gate functions as designed. DNA sequence and experimental conditions are summarized in Tables 4-1, 4-2, and 15.

Demonstration of an INHIBIT gate is significant because two-input AND, OR, and INHIBIT operations constitute a functionally complete set of Boolean functions.

Second, increasing the number of distinct DNA bonds, which can be disassembled, in a receptor-floater dimer enables the fan-in of a Disassembly gate.

In FIG. 21B, a circuit diagram of a six-input Disassembly gate implemented with $R_2$-$F_2$ and operation of the gate (left), and a kinetic experiment graph (right) are illustrated.

As shown in FIG. 21B, when the release of a G-NF ($F_2$) from a G-NR ($R_2$) requires the disconnection of three different DNA bonds, each of which can be cleaved by two-input OR logics, the disassembly is regulated by a six-input expression (X3 OR X4) AND (X5 OR X6) AND (X7 OR X8).

Figure 23:
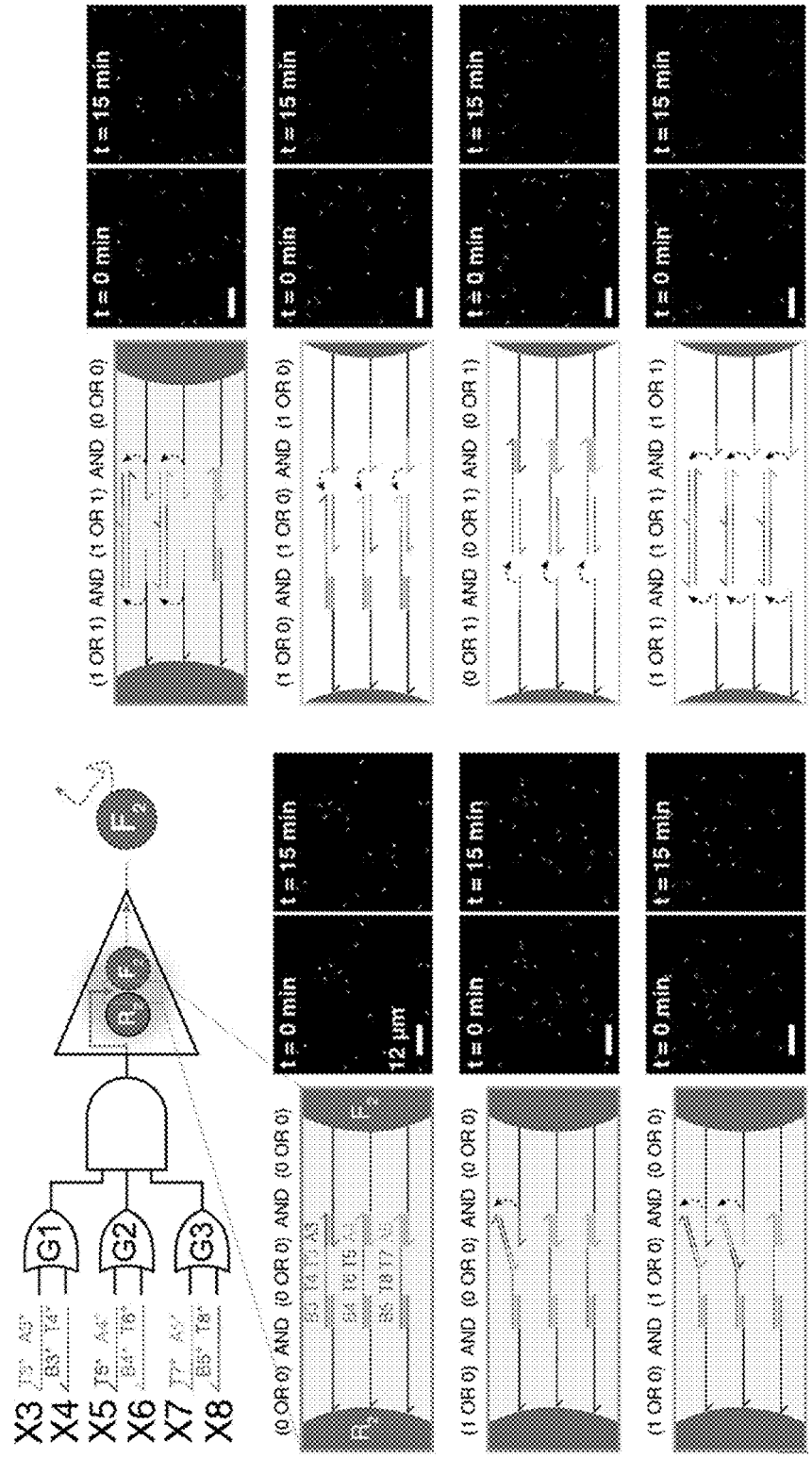
FIG. 23 shows an operation of a six-input disassembly gate.

FIG. 23 shows an operation of a six-input disassembly gate.

In FIG. 23, a domain-level diagram (left) and a reconstructed dark-field image of the six-input Disassembly gate that processes (X3 OR X4) AND (X5 OR X6) AND (X7 OR X8) logic are illustrated. DNA sequence and experimental conditions are summarized in Tables 4-1, 4-2, and 15. As shown in FIG. 23, dark-field imaging confirms that the six-input logic gate produces outputs only in the TRUE states with an ON/OFF level of over 88 folds.

Figure 24A:
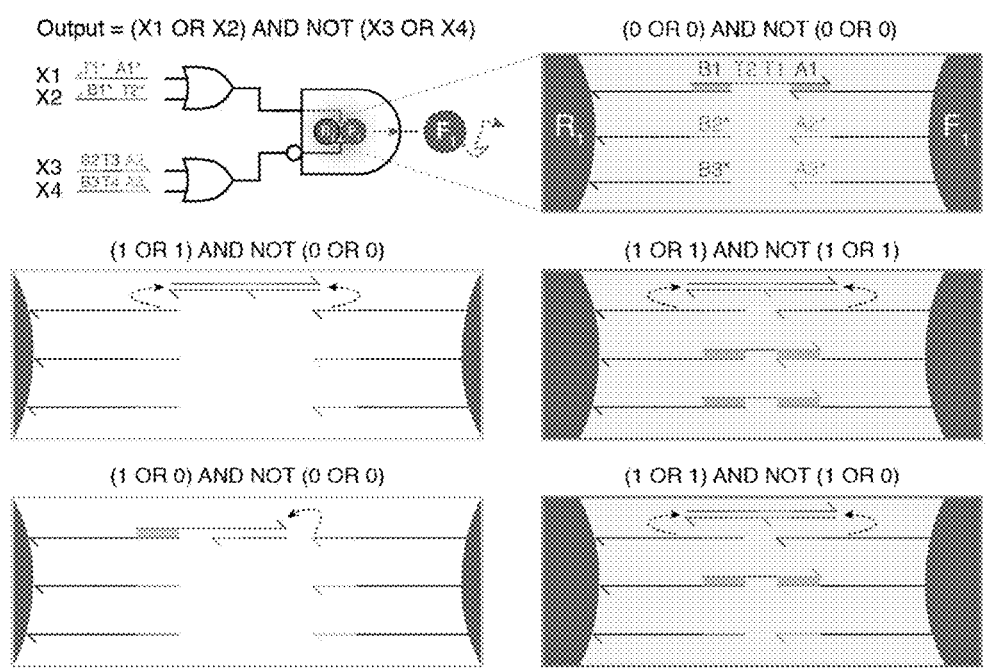
FIG. 24A to FIG. 24B show a multiple-input Disassembly gate.
Figure 24B:
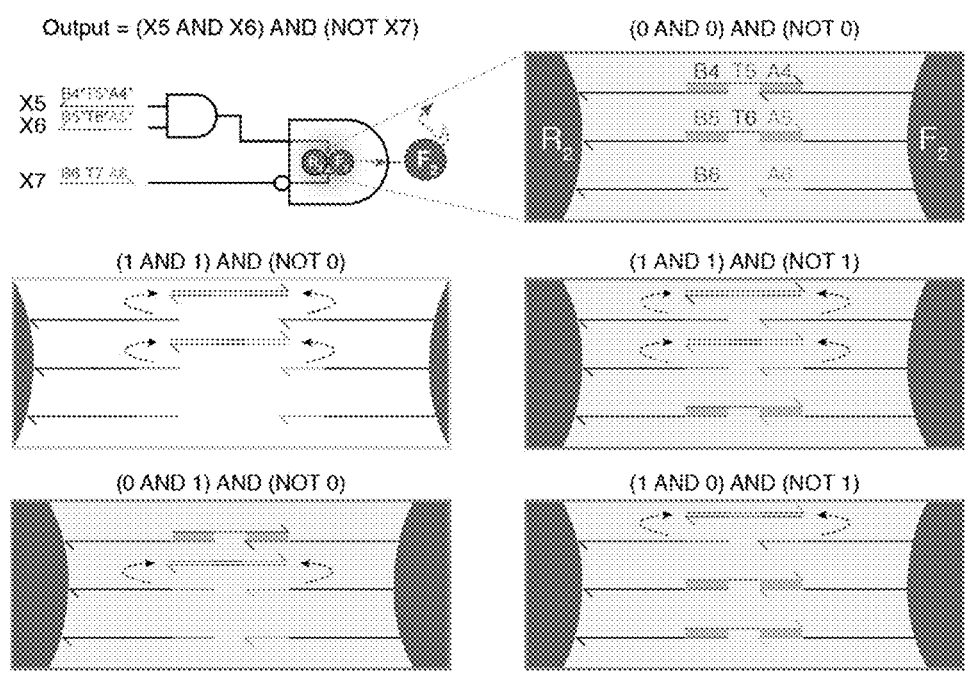

FIG. 24A to FIG. 24B show a multiple-input Disassembly gate.

In FIG. 24A and FIG. 24B, a Disasembly gate that is capable of more complex logic expression by combining the INHIBIT logic and the approach method used in implementation of fan-in.

In FIG. 24A, a four-input Disassembly gate that process (X1 OR X2) AND NOT (X3 OR X4) logic expression is illustrated. In this design, X1 or X2 may cleave the DNA bond (in the pre-formed $R_1$-$F_1$ dimer), and X3 or X4 may form a bond in the dimer. In order for disassembly to occur, in the absence of X3 and X4, bond cleavage reactions must proceed.

In FIG. 24B, a three-input Disassembly gate that processes (X5 AND X6) AND (NOT X7) logic is illustrated. For disassembly, X5 and X6 need to remove two different DNA bonds without forming an additional bond by X7.

As shown in FIG. 24A and FIG. 24B, two strategies based on kinetic competitions and increased "bond orders" can be used to yield Disassembly logic gates with complex multi-input Boolean logic, such as (X1 OR X2) AND NOT (X3 OR X4) and (X1 AND X2) AND (NOT X3).

Third, a two-input Disassembly AND gate having three outputs is illustrated in FIG. 21C. The Disassembly gate processes two types of DNA input with AND logic and generates three different mobile floaters $F_3$, $F_4$, and $F_5$ as outputs. Three representative R-F pairs are marked as $R_3$-$F_3$, $R_3$-$F_4$, and $R_3$-$F_5$.

As shown in FIG. 21C, the fan-out of the logic gate is demonstrated by implementing identical two-input Disassembly AND logic in three different receptor-floater pairs, each having a distinct floater signal. The disassembly reactions of the three floaters are readily analyzable owing to the characteristic signal of each floater. Dissociations of R-NFs, G-NFs, and B-NFs from the respective receptors results in step-wise decreases in the R, G, and B intensities of the receptor signals. The Disassembly gate releases all three outputs $F_3$, $F_4$, and $F_5$ according to the logic, with ON/OFF levels over 20 holds.

As the complexity of reactions within the reactor-floater increases, incomplete reactions or spurious interactions also arise. Thus, relying on engineering the floater-receptor surface interface is not an efficient and scalable strategy for constructing complex circuits. Thus, in the present disclosure, nanoparticle "network programming", which can connect two single particle logic gates with AND logic or OR logic, is used.

Figure 25A:
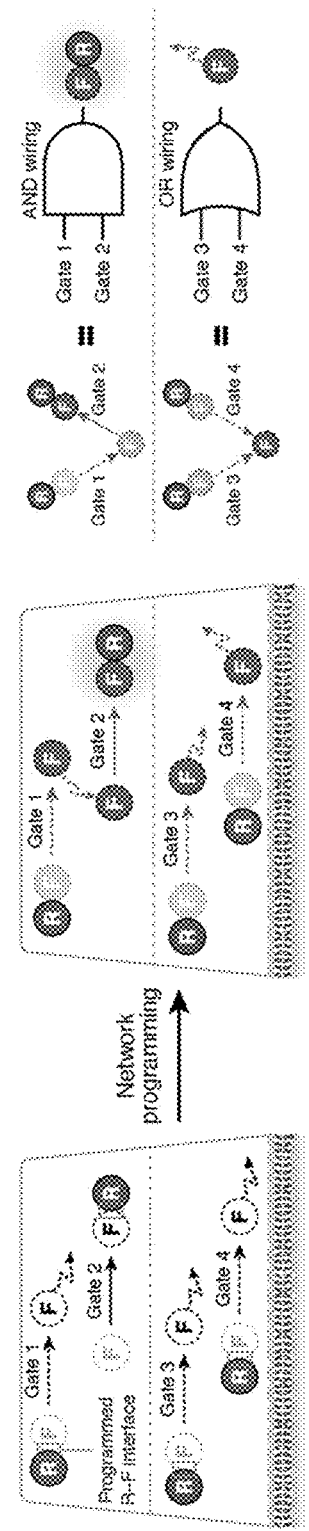
FIG. 25A to FIG. 25C illustrate connection of nanoparticle logic gates through network programming.
Figure 25B:
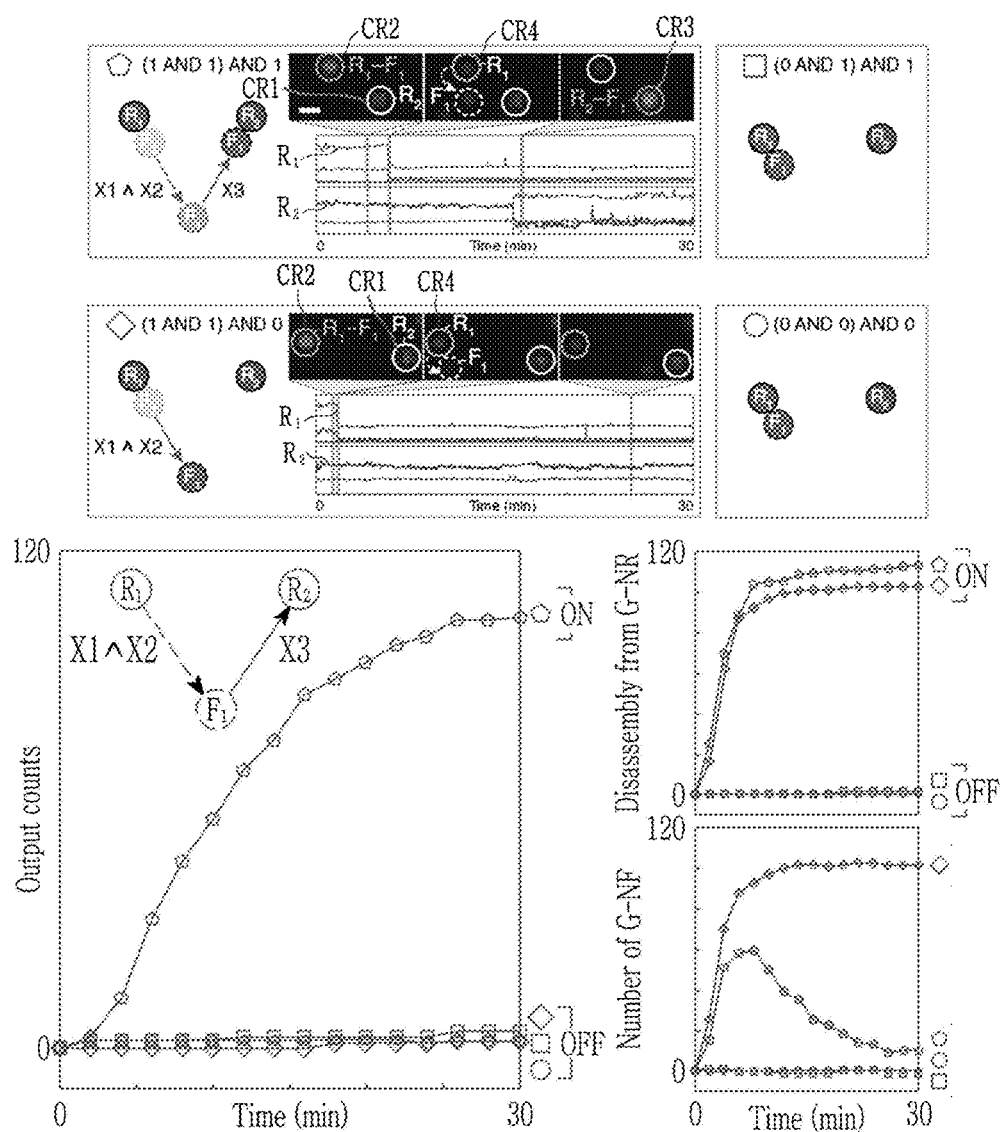
Figure 25C:
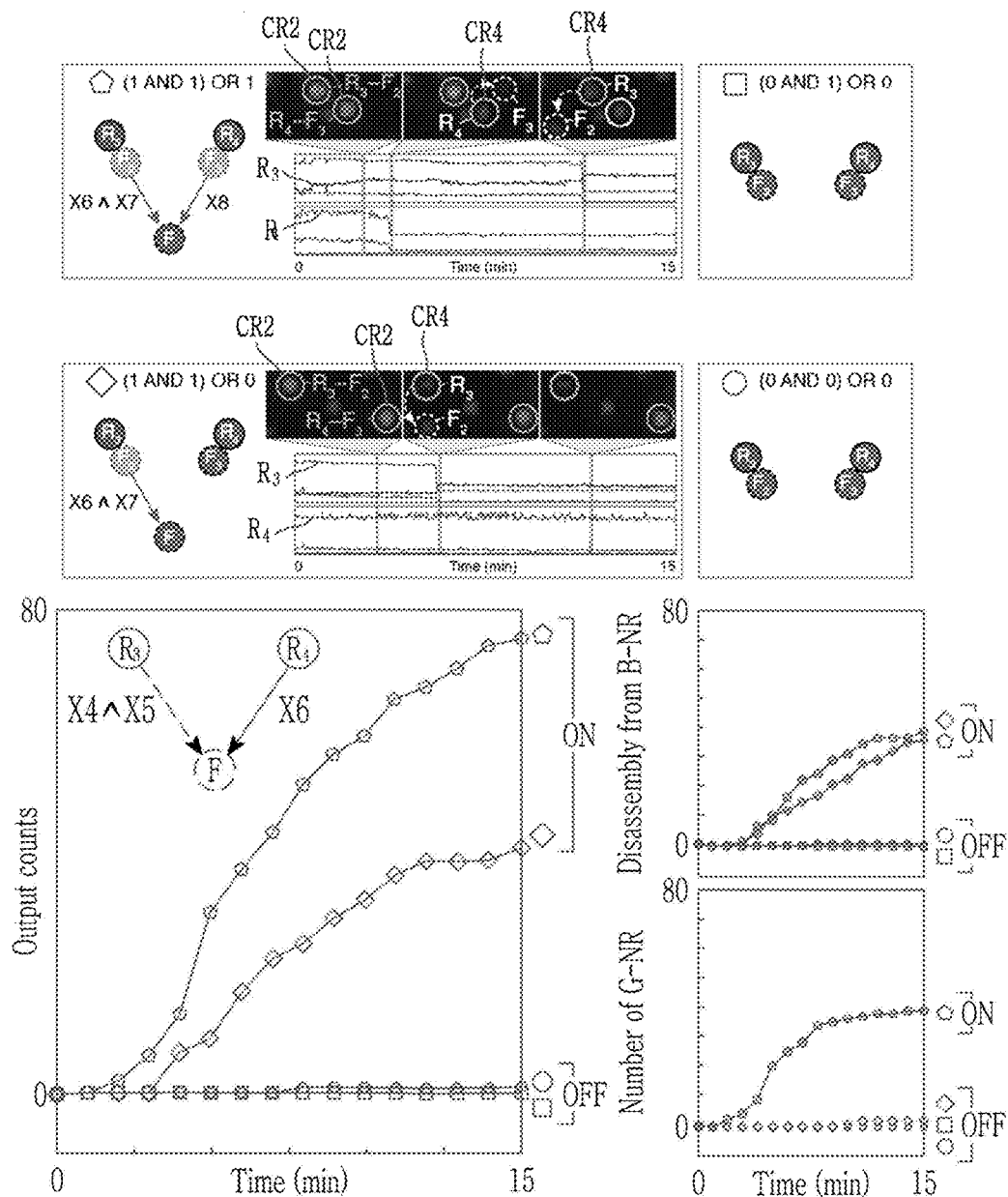

FIG. 25A to FIG. 25C illustrate connection of nanoparticle logic gates through network programming.

DNA sequence and experimental conditions are summarized in Table 5 and Table 16. Experiments are carried out at 25° C. in a 1× PBS buffer solution.

In the network programming illustrated in FIG. 25A, two nanoparticle gates, in each of which the R-F interface is programmed with desired logic, may be modularly wired in the nanoparticle network level. A floater designed to sequentially participate in Disassembly gate 1 and Assembly gate 2 enables wiring of the two gates with AND logic (upper). When two Disassembly logic gates (gate 3 and gate 4) generate floaters with the same signal, the two gates are wired with OR logic (lower).

FIG. 25B and FIG. 25C illustrate a circuit diagram of a network-level wiring strategy using a representative single-particle dark-field analysis (black-colored background figure) in the left column, and assembly and disassembly processes in the wiring strategy circuit diagram are respectively marked with the solid line and dotted arrow. Reactive receptors $R_1$, $R_2$, $R_3$, and $R_4$ are marked with a before-assembly circle CR1 or before-disassembly circle CR2 and an after-assembly circuit CR3 or after-disassembly circuit CR4. Kinetic experiment results are illustrated in lower ends in FIG. 25B and FIG. 25C, and the final output counts (left) and quantifications of intermediate reactions are illustrated (right). $\wedge$ denotes AND logic, and $\vee$ denotes OR logic.

FIG. 25B illustrates wiring of logic gates with AND logic. A floater $F_1$, which is bound to the first receptor $R_1$ in its initial state, is designed to act as a Disassembly AND logic gate (X1 AND X2), and subsequently as an Assembly YES gate (X3) with the second receptor $R_2$. The generation of the $R_2$-$F_1$ dimer is a final output. In FIG. 25B, the receptor $R_1$ before disassembly is marked by a circle CR2, the first receptor $R_1$ after disassembly is marked by a circle CR4, and the second receptor $R_2$ after assembly is marked by a circle CR3.

The logic gates shown in FIG. 25C are wired with OR logic. The Disassembly AND gate (X4 AND X5) and the Disassembly YES gate X6 are both designed to release a G-NF, and thus generation of the G-NF is controlled by a circuit that combines the two gates with OR logic. In FIG. 25C, the receptors $R_3$ and $R_4$ before disassembly are marked with a circle CR2, and the receptors $R_3$ and $R_4$ after disassembly are marked with a circle CR4.

First, network-level AND wiring can be demonstrated by enabling the use of the floater in the Disassembly and Assembly gates as shown in FIG. 25B. For example, in the Disassembly AND gate formed of a G-NR $R_1$ and a G-NF $F_1$, the G-NF $F_1$ is released, and the G-NF $F_1$ released later acts as Assembly YES with another receptor B-NR $R_2$.

In this network-level wiring scheme, the formation of a B-NR ($R_2$)-G-NF ($F_1$) dimer becomes an output of the AND-AND cascade circuit (X1 AND X2) AND X3.

Figure 26:
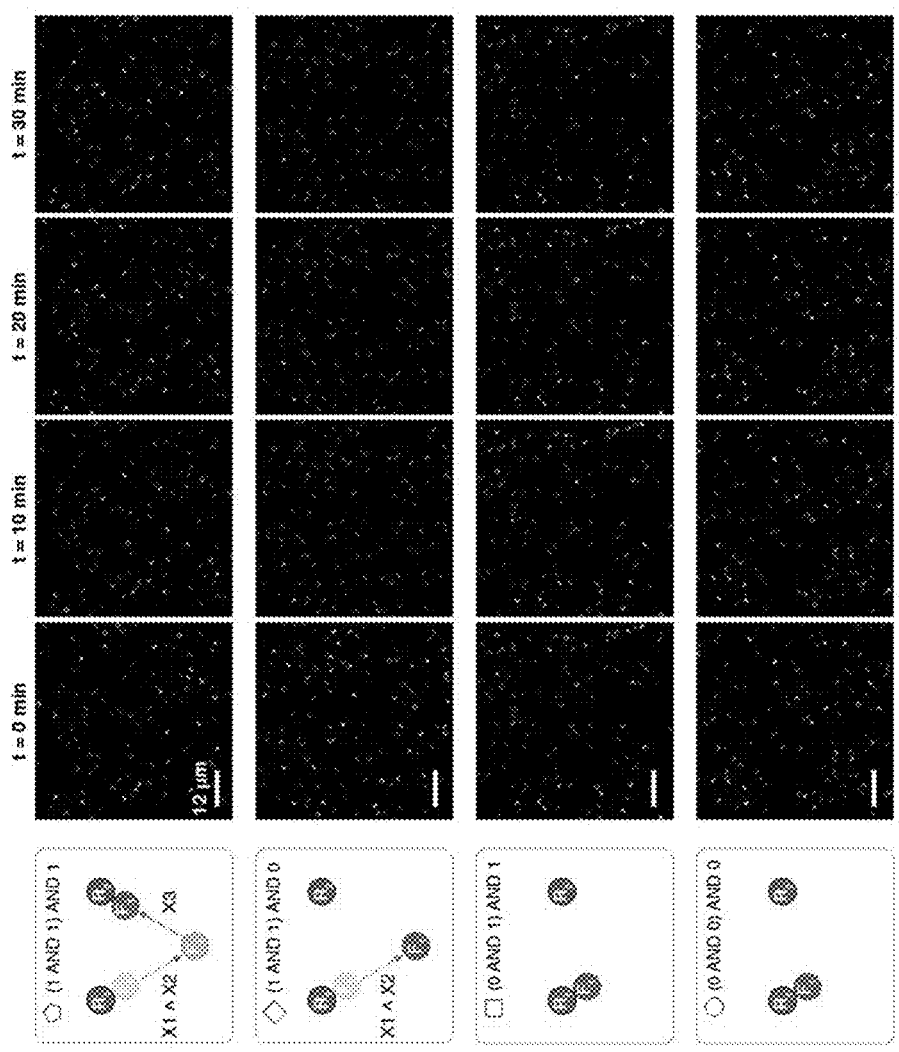
FIG. 26 shows a reconstructed dark-field snapshot of two-layer AND-AND cascade circuit.

FIG. 26 shows a reconstructed dark-field snapshot of two-layer AND-AND cascade circuit.

Release of the G-NF $F_1$ from the G-NR $R_1$ is controlled by AND logic (X1 and X2). The released $F_1$ may be tethered to $R_2$ only when an assembly input X3 is present. The final circuit output is controlled by a three-input logic equation (X1 AND X2) AND X3. Green intensity in the first condition (1 AND 1) AND 1 is decreased in the receptor $R_1$ and increased in the receptor $R_2$ and thus is successfully cascaded by the G-NF $F_1$. Only a decrease in green intensity is observed in the second condition (1 AND 1) AND 0. Lack of signal increase indicates that the released floater $F_1$ is not tethered to another receptor. No reaction was seen in the two drawings below.

The AND-AND cascade circuit is described by a reaction graph, where two receptors $R_1$ and $R_2$ are serially connected to a floater $F_1$. The circuit provides an ON/OFF level of 36 folds. As shown in FIG. 26, the intermediate disassembly reactions can also be monitored and analyzed simultaneously owing to their distinct optical signals. The upstream Disassembly AND gate results in an ON/OFF level of over 89 folds. Through this parallel analysis, floater $F_1$ population over time in response to the four input combinations is estimated, and the released floater $F_1$ can be subsequently bound to receptor $R_2$ only when the input X3 is TRUE.

For the (1 AND 1) AND 1 condition, over 92% of $F_1$ responds to the assembly input X3. This result indicates that the sequential disassembly-assembly cascade is highly efficient. Other two-input Disassembly gates, such as OR and INHIBIT gates, can be modularly rewired without optimization, resulting in the OR-AND cascade shown in FIG. 27 and the INHIBIT-AND cascade shown in FIG. 28.

Figure 27:
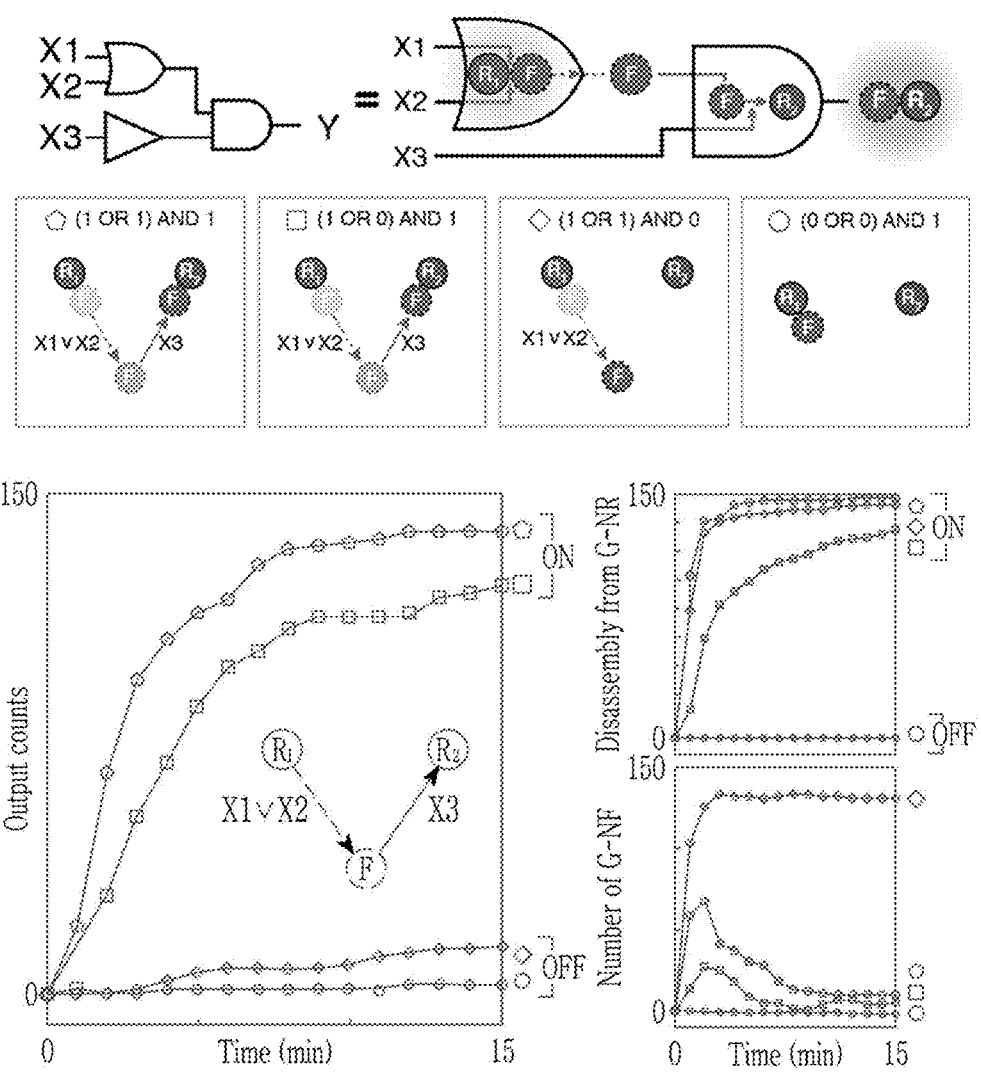
FIG. 27 shows a two-layer OR-AND cascade circuit.

FIG. 27 shows a two-layer OR-AND cascade circuit.

In the two-layer OR-AND cascade circuit shown in FIG. 27, network-level AND wiring is applied in construction of a nanoparticle circuit that performs (X1 OR X2) AND X3 logic computation. The circuit provides an ON/OFF level of over 11 folds by generating an accurate output corresponding to the logic. The upstream disassembly gate shows an ON/OFF level of over 128 folds. As in the AND-AND cascade circuit shown in FIG. 25B, the population dynamics of G-NF can be estimated in the circuit. According to analysis, the released G-NF is bound to a B-NR only when the input X3 that is required for assembly reaction exists. DNA sequence and experimental conditions are summarized in Table and Table 20.

Figure 28:
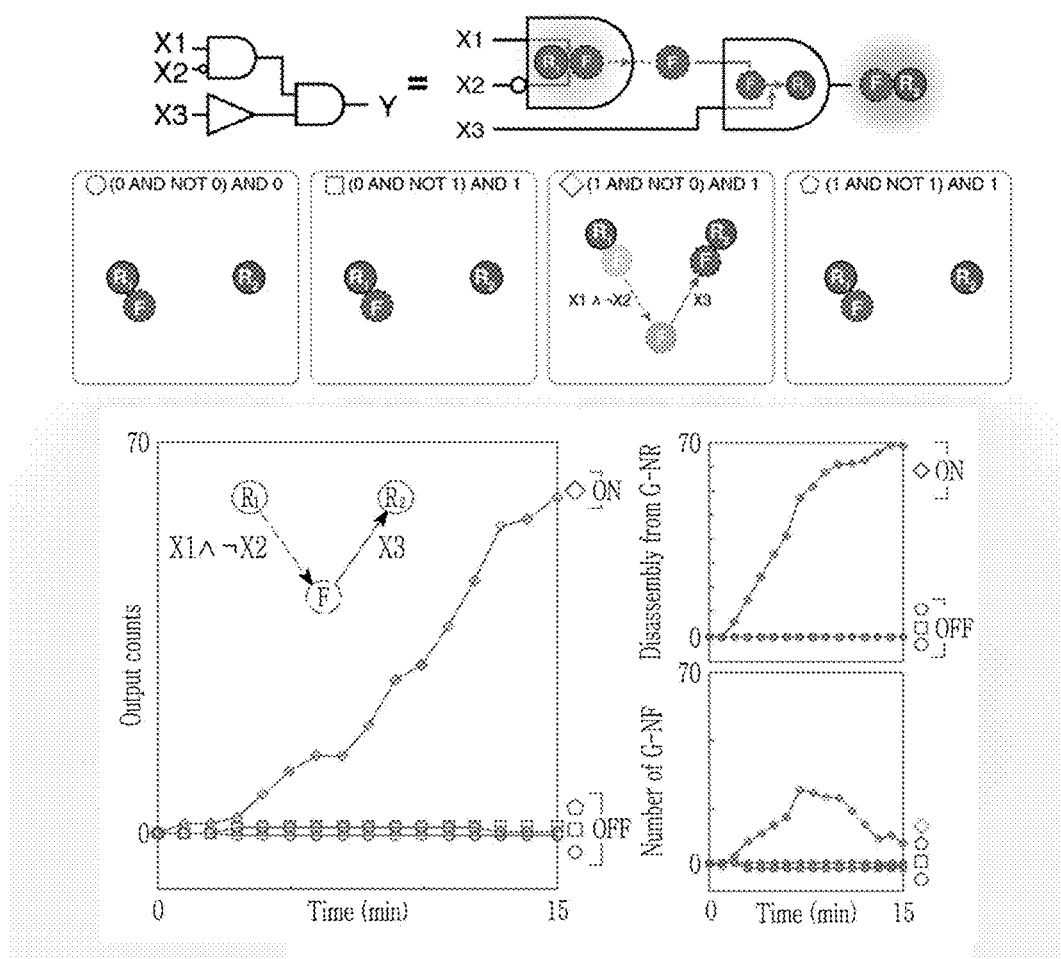
FIG. 28 shows a two-layer INHIBIT-AND cascade circuit.

FIG. 28 shows a two-layer INHIBIT-AND cascade circuit.

In the two-layer INHIBIT-AND cascade circuit shown in FIG. 28, a network-level AND wiring is applied to construct a nanoparticle circuit that performs (X1 AND NOT X2) AND X3 logic computation. This circuit performs logic computation as designed and thus an ON/OFF level is over 37 folds. The upstream INHIBIT gate provides an ON/OFF level of over 70 folds. The released G-NF is bound to a B-NR only when the input X3 exists. DNA sequence and experimental conditions are summarized in Table 11 and Table 21. Second, the OR wiring may be implemented to produce floaters with identical optical signals in parallel by designing two Disassembly gates.

As shown in FIG. 25C, for example, a Disassembly AND gate formed of B-NR ($R_3$) and G-NF ($F_2$) is installed along with a Disassembly YES gate formed of a G-NR ($R_4$) and another G-NF ($F_3$). In the circuit ((X4 AND X5) OR X6), G-NFs can be produced from either the AND gate or the YES gate such that the two gates are thus wired with OR logic.

Figure 29:
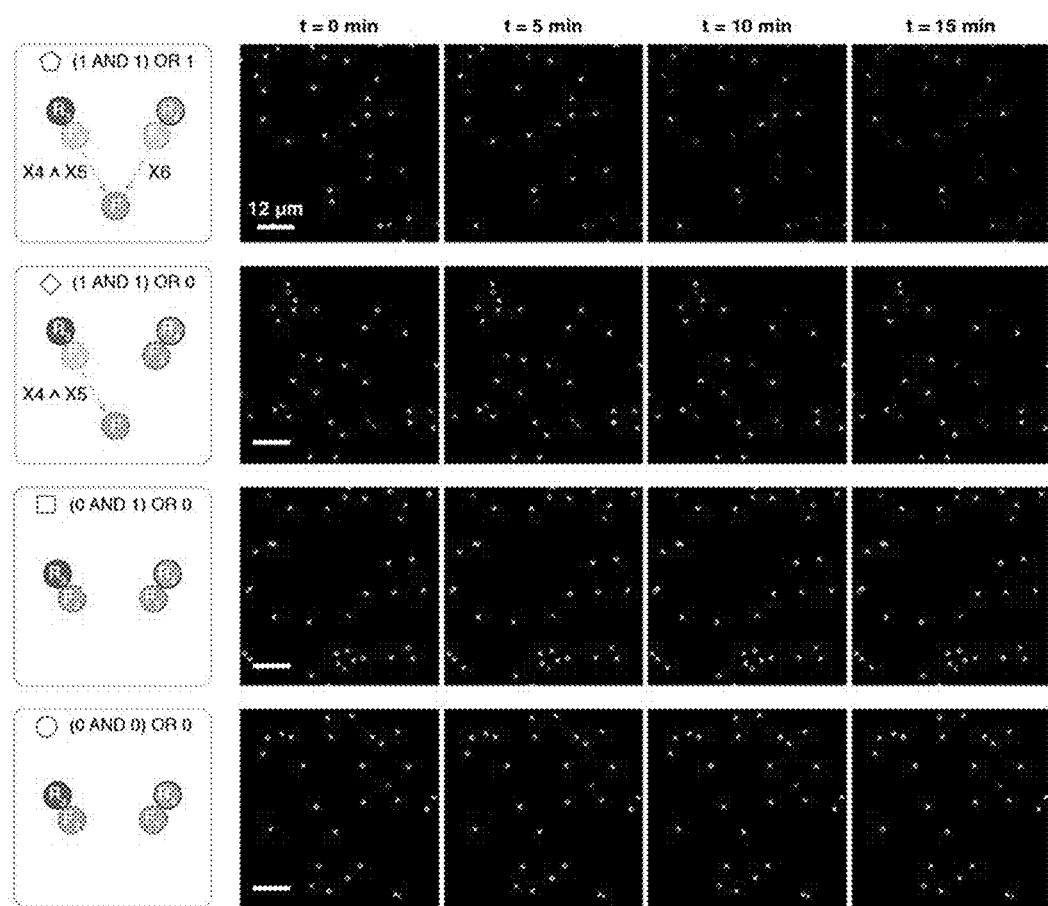
FIG. 29 shows a dark-field snapshot of the two-layer AND-OR cascade circuit.

FIG. 29 shows a dark-field snapshot of the two-layer AND-OR cascade circuit.

Referring to FIG. 29, dark-field snapshots of the two-layer AND-OR cascade circuit, the release of G-NFS ($F_2$) from B-NR ($R_3$) is controlled by AND logic (X4 AND X5), and the release of another G-NF ($F_3$) from G-NR ($R_4$) is controlled by YES logic (X6). The final circuit output is controlled by three-input logic expression (X4 AND X5) OR X6. In the first condition (1 AND 1) OR 1, the green intensity is reduced in $R_3$ and $R_4$ and thus G-NF is successfully released from each receptor. In the second condition (1 AND 1) OR 0, a decrease in the green intensity is observed only in B-NR. That is, the $R_3$-$F_2$ pair is cleaved as a result of the AND logic computation.

As shown in FIG. 29, the AND-OR cascade outputs an ON/OFF output level of over 55 folds. The operations of the two upstream Disassembly gates are evaluated separately to show that each gate carried out computation with high ON/OFF levels without interfering with each other.

Figure 30:
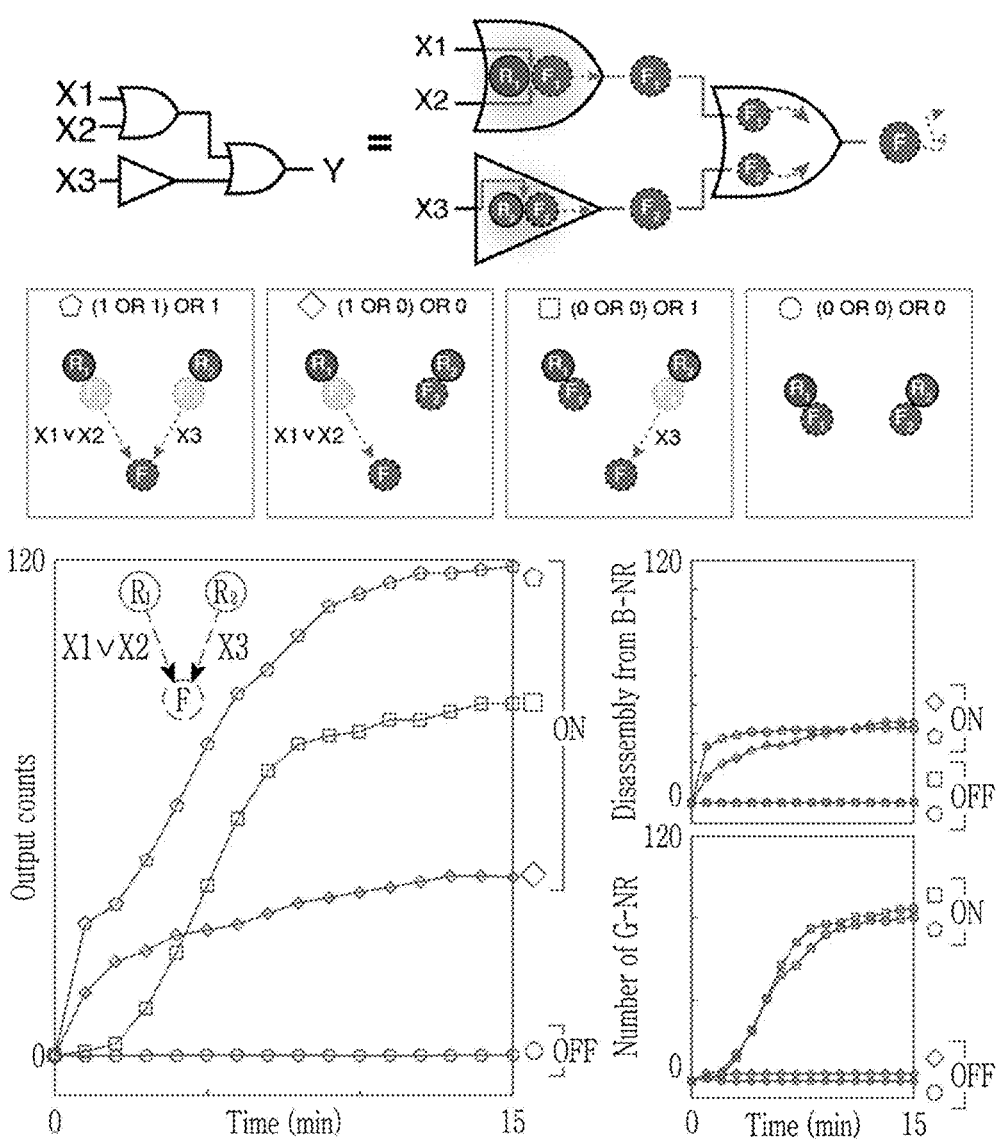
FIG. 30 shows a two-layer OR-OR cascade circuit.

FIG. 30 shows a two-layer OR-OR cascade circuit.

As shown in FIG. 30, a disassembly OR gate may also be connected to yield an OR-OR cascade circuit.

In the two-layer OR-OR cascade circuit shown in FIG. 30, a network-level OR wiring scheme is applied to form a nanoparticle circuit that performs (X1 OR X2) OR X3 logic computation. This circuit performs computation as designed such that an ON/OFF level becomes over 43 folds. The upstream Disassembly OR gate and the YES gate respectively provide ON/OFF levels over 37 folds and 24 folds. DNA sequence and experimental conditions are summarized in Table 12 and Table 22.

Since Disassembly gates support fan-out, any upstream Disassembly gates should be able to readily generate multiple floaters, each responsible for a distinct downstream computation. The released floaters can be subsequently "plugged" into another layer of Assembly gate through network-level AND wiring. This approach enables complex multi-layer cascades.

To demonstrate the modularity of circuit design on LNT, a multiplexer MUX 2-to-1 is implemented by wiring previously introduced logic gates via network programming.

Figure 31A:
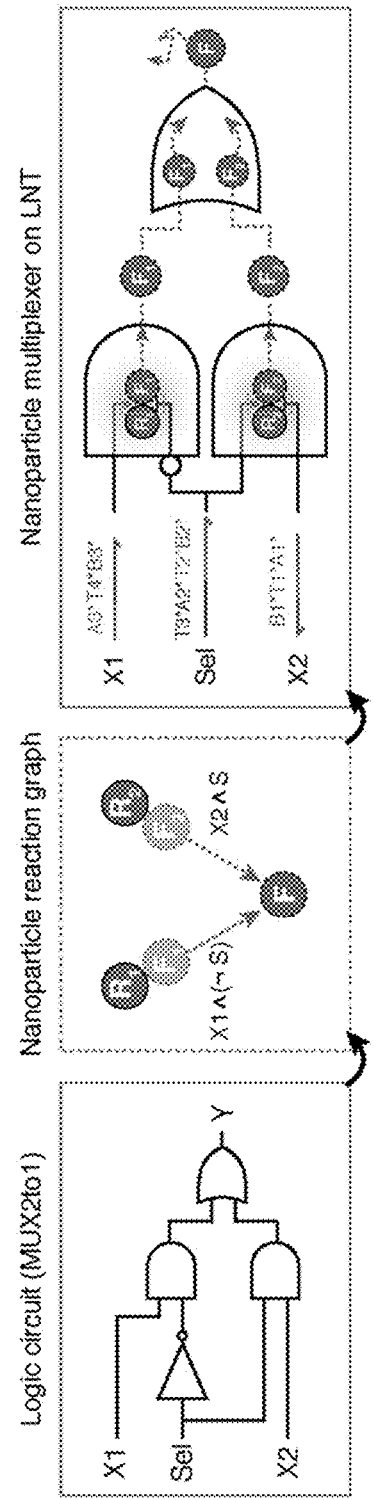
FIG. 31A to 31C show design and implementation of a nanoparticle multiplexer circuit.
Figure 31B:
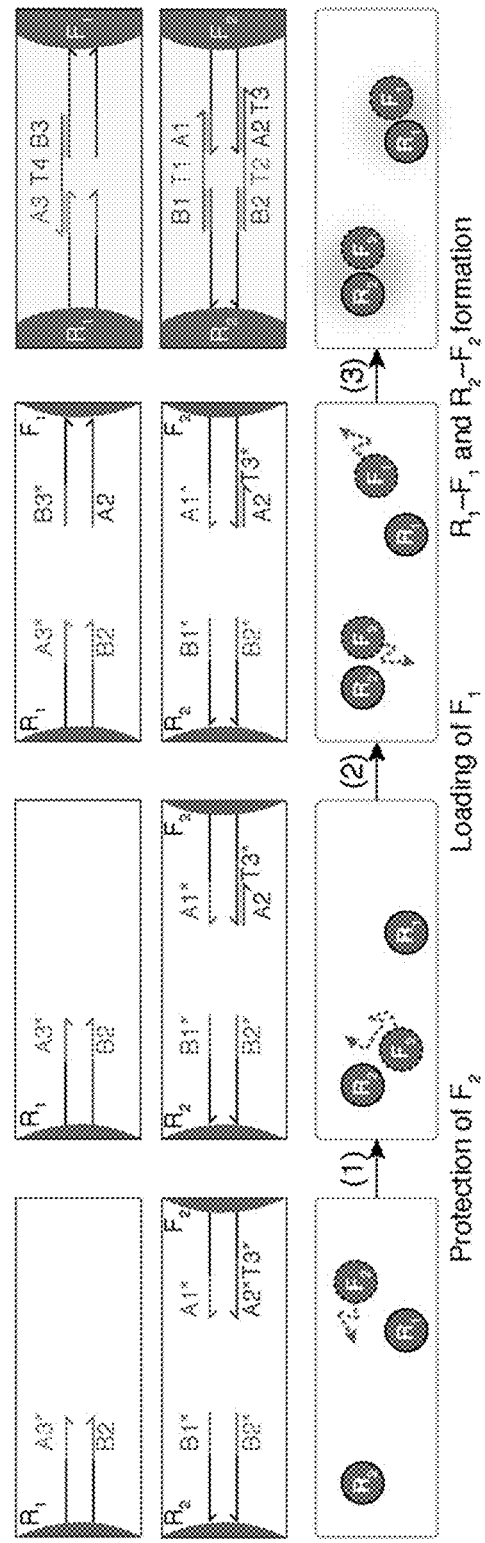
Figure 31C:
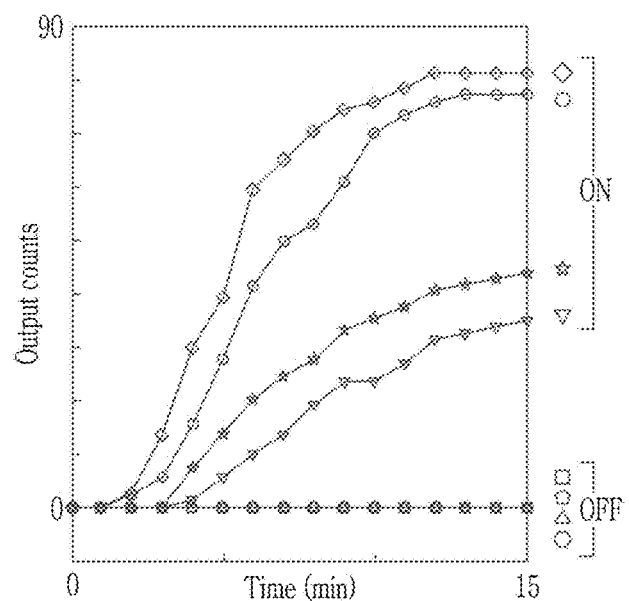

FIG. 31A to 31C show design and implementation of a nanoparticle multiplexer circuit.

In FIG. 31A, a multiplexer circuit MUX 2-to-1 implemented with a nanoparticle network is illustrated. The multiplexer is formed by connecting a Disassembly INHIBIT gate (X1 AND NOT Sel) and a Disassembly AND gate (Sel AND X2) with OR logic. Four nanoparticles $R_1$, $R_2$, $F_1$, and $F_2$ form the multiplexer circuit.

In FIG. 31B, modularized implementation of a nanoparticle multiplexer on a lipid bilayer is illustrated. Circuit constituent elements can be highly controlled and loaded in a module manner. To prevent undesired natural interactions between $F_1$ and $F_2$, $F_2$ is protected by a guard strand A2 prior to tethering $F_1$.

In FIG. 31C, measured performance of the multiplexer circuit and a truth table are illustrated. A domain-level diagram for a circuit operation is described in FIG. 32. In analysis of time-lapse dark-field images where operation processes of the circuit are recorded, the nanoparticle multiplexer yielded the expected responses to eight different input combinations with an ON/OFF level of over 35 folds. DNA sequence and experimental conditions are summarized in Table 6 and Table 17. Experiments are carried out at 25° C. in a 1× PBS buffer solution.

The circuit diagram of FIG. 31A can be translated into a reaction graph diagram that guides the design of surface DNA ligands for each nanoparticle. At the nanoparticle level, the multiplexer circuit is formed of two R-F pairs: $R_1$-$F_1$ (X1 AND NOT Sel) and $R_2$-$F_2$ (Sel AND X2). Two Disassembly gates that produce a G-NF as an output are wired with OR logic. In particular, in the multiplexer circuit, selectors Sel, which are selected inputs, should be simultaneously processed by two different logic operations in INHIBIT logic (within $R_1$-$F_1$) and AND logic (within $R_2$-$F_2$). Under such a design limitation, each nanoparticle should expose a sequence domain (A2 or B2) that is fully complementary to a domain of another particle. Due to such a condition, nanoparticle circuit constituent elements can spontaneously form aggregates in a solution step. In order to prevent such spontaneous interaction, the nanoparticle circuit constituent elements are loaded in a specific order and the guard strand A2 is introduced.

As shown in FIG. 31B, the multiplex circuit can be readily constructed in the LNT platform because undesired spontaneous interactions between nanoparticles can be compartmentalized and controlled during a tethering and pre-dimerization process. $R_1$ and $R_2$ did not collide with one another because of their immobility, and $F_1$-$F_2$ interaction is temporarily blocked by protecting the A2* domain of $F_2$ by introducing the guard strand A2 in the tethering process. After four types of nanoparticles are loaded in the lipid bilayer, two Disassembly logic gates are prepared by forming corresponding $R_1$-$F_1$ and $R_2$-$F_2$ dimers.

Figure 32:
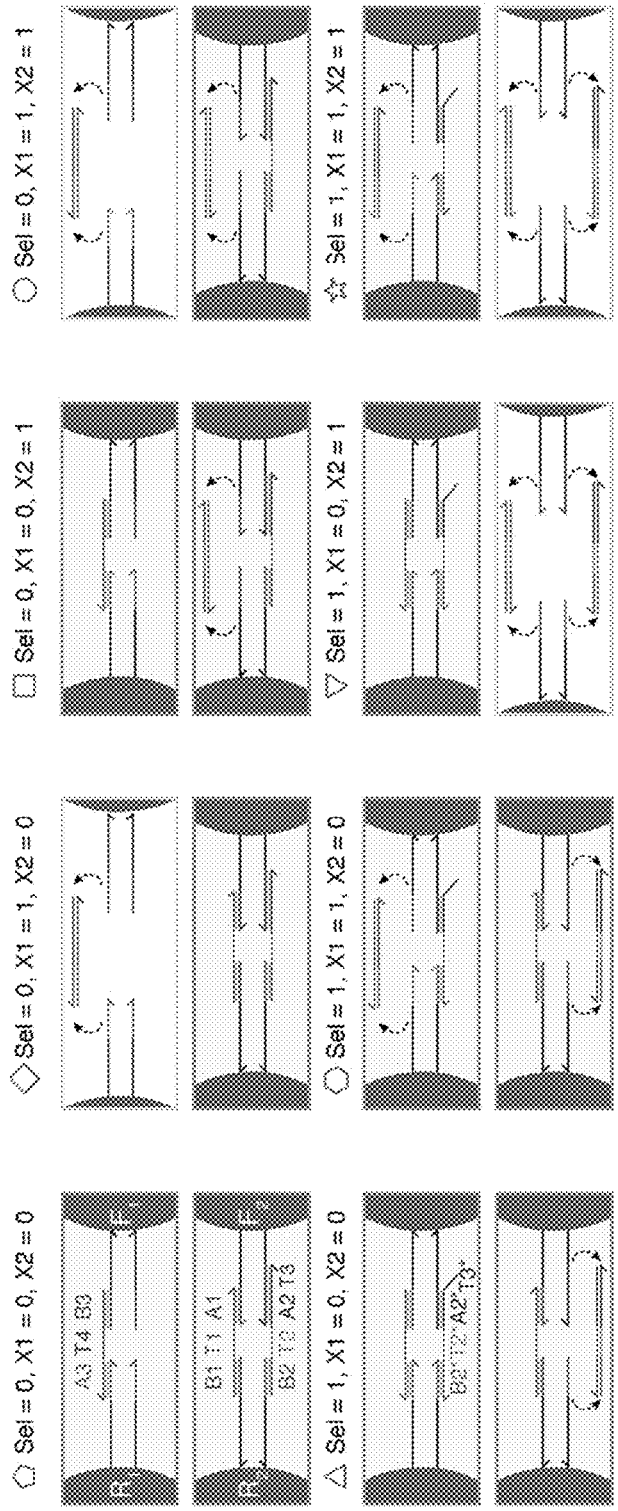
FIG. 32 shows a multiplex circuit operation in a domain level.

FIG. 32 shows a multiplex circuit operation in a domain level.

The nanoparticle surface ligand is designed to allow two different receptor-floater pairs to simultaneously process selector strands (Sel). The multiplexer selects one of two inputs X1 and X2 by using the selector strand (Sel) and translates the selected input into a single output.

The demonstration of the nanoparticle multiplexer shows that it is possible to design and operate nanoparticle circuits on the LNT platform in a modular and controllable manner.

Operating principles of LNT are unit in the following three aspects.

First, the computation is solely driven by SLB-tethered nanoparticles whose particle-by-particle interactions are programmable and readable in situ. A dynamic network of individual nanoparticles is equivalent to a logic circuit.

Second, since the cascading is exclusively driven by floaters, a process d does not require signal restoration or amplification. That is, floaters are "wires" carrying information of upstream gates into downstream gates via lateral diffusion that is robust to external conditions.

Figure 33A:
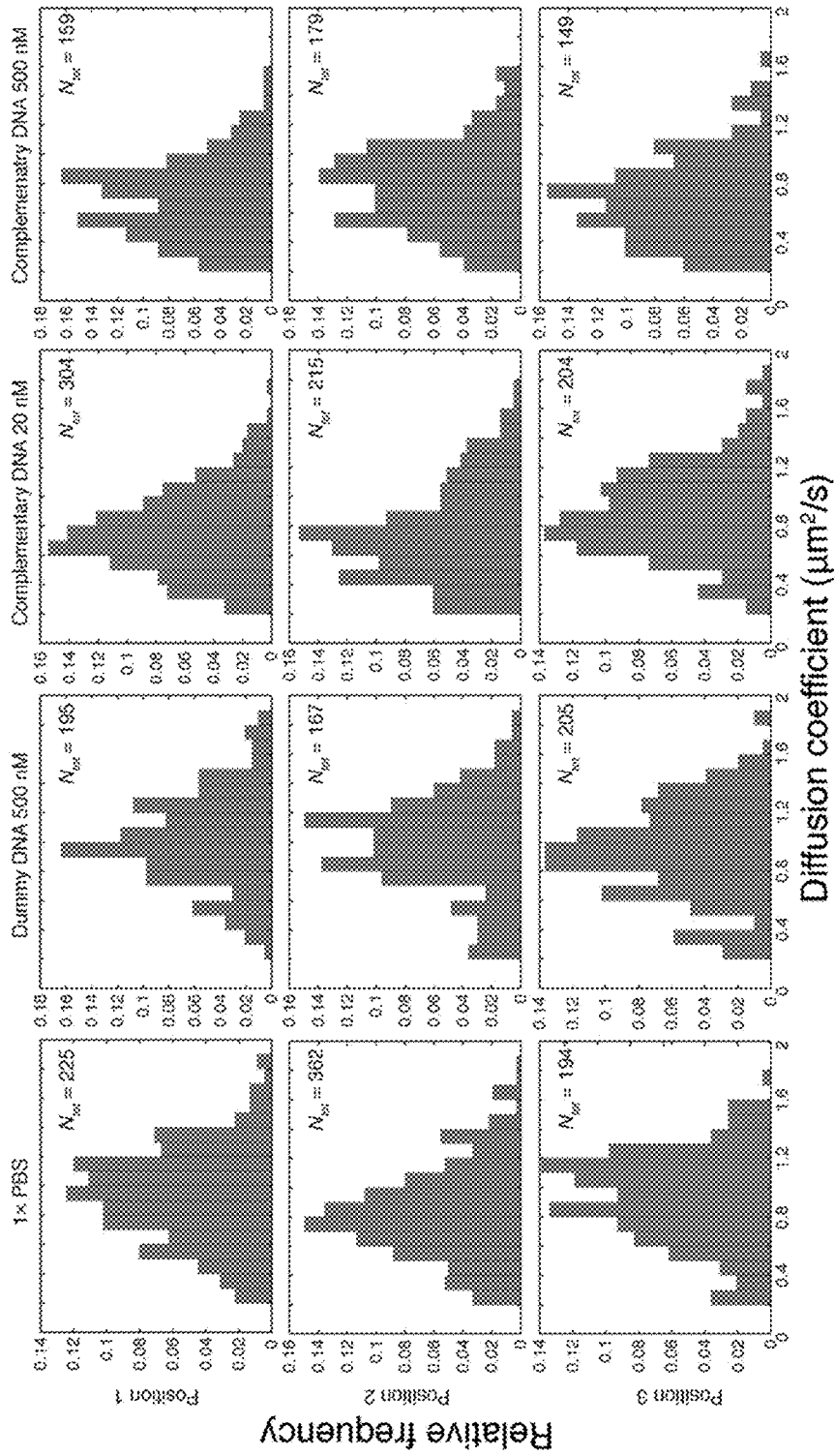
FIG. 33A to FIG. 33C show an analysis with respect to robustness of floater diffusion.
Figure 33B:
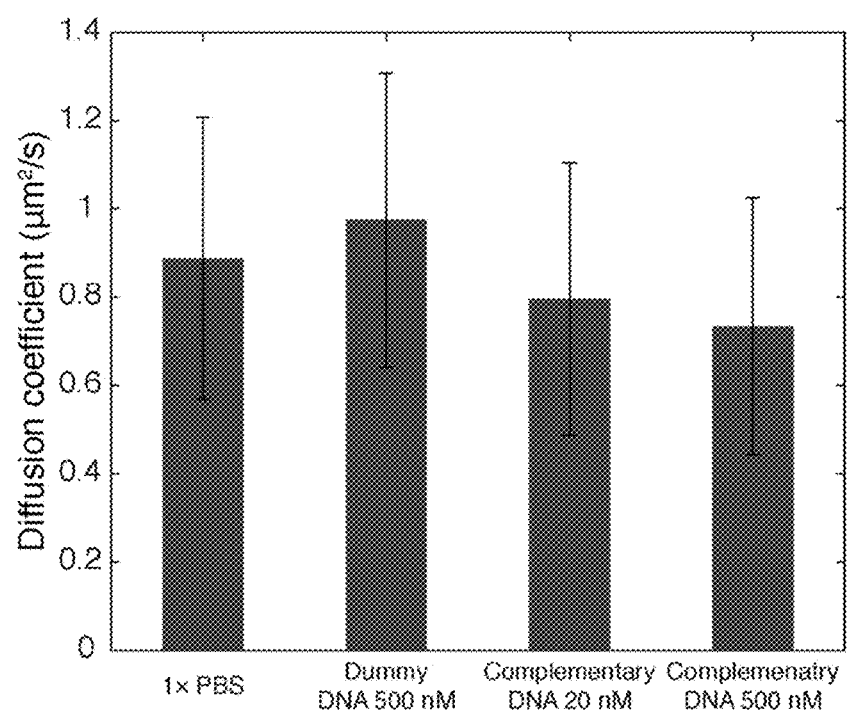
Figure 33C:
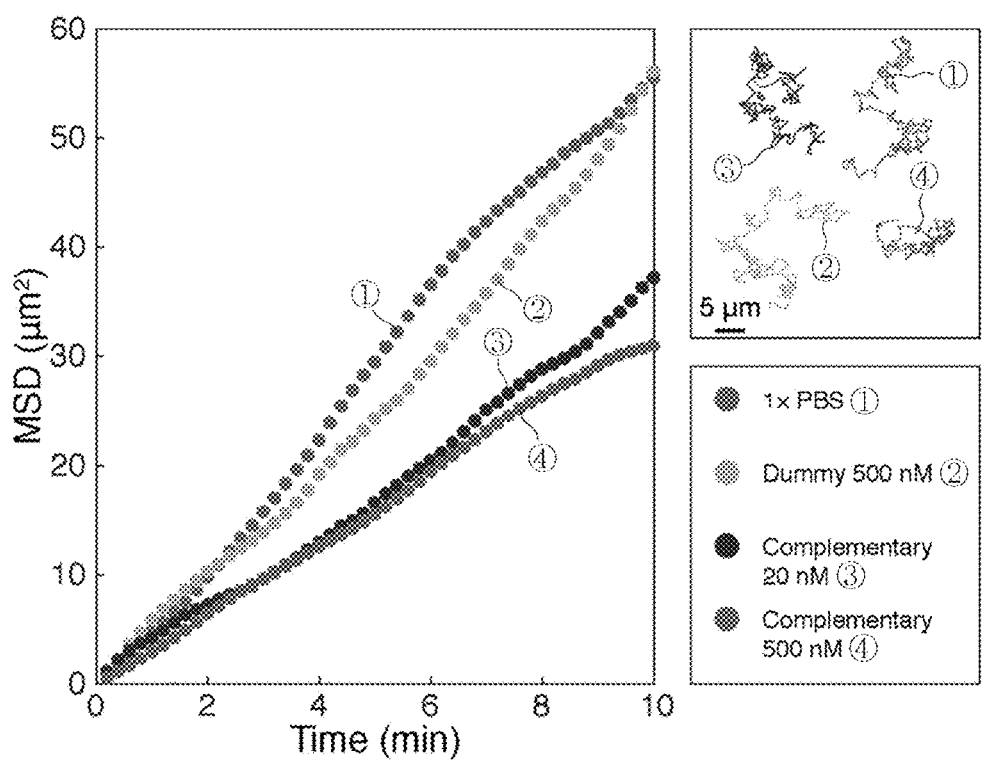

FIG. 33A to FIG. 33C show an analysis with respect to robustness of floater diffusion.

As shown in FIG. 33A to FIG. 33C, diffusion dynamics of the floater G-NFs is analyzed in various conditions. For example, in a 1× PBS buffer, a floater diffusion process can be analyzed under diverse conditions together with dummy DNA of a high concentration (500 nM), a complementary DNA input of a low concentration (20 nM), and a complementary DNA input of a high concentration (500 nM).

There is no complementarity between the surface ligand of the floater G-NF and a dummy DNA 5'-GTTTAAGAT-TTATGGTTAAGCGTAGATTAAGTATTAAG-3'. AG-NF used in a single input Assembly YES gate is used in analysis of the G-NF (refer to Table 1). Analysis in each solution is repeated at three different positions in the lipid nanotablet.

FIG. 33A is a bar graph of the diffusion coefficient of G-NF under each condition. FIG. 33B shows a diffusion coefficient of the G-NF, and FIG. 33C shows a mean square displacement with respect to time to plot four representative diffusion trajectories. The analysis results show that the overall diffusion behavior of G-NFs is robust to the chemical environment of a solution.

Third, a spatial constraint is exploited to control the flow of molecular information in nanoparticle "signaling" networks. As shown in the multiplexer, an undesired interaction can be modularly controlled. Then, complex digital local operations can be implemented using a relatively small number of particles and ligand types. Through the integration with a lipid bilayer, nanoparticles are programmed, controlled, and visualized at the single-particle level, thereby designing and implementing a desired circuit according to digital principles. Such a function was not possible in the existing method, which relied only on nanoparticles "passively" clustered on a solution. The scope of molecular information that can be processed on LNT can be expanded several ways.

First, solution-phase molecular circuits that release single-stranded DNA as outputs can be synergistically interfaced with an LNT platform because only DNA molecules are needed to operate nanoparticle circuits on the NLT. In this case, a molecule circuit on the solution can additionally process molecular information. This approach can mediate communications across different nanoparticle circuit modules on a lipid bilayer as well as those with external environments.

Second, particle modifications based on diverse chemical ligands other than DNA can be readily introduced to process diverse chemical information. When introducing new surface chemistries on nanoparticles, the design constraints (that may arise from crosstalk between different surface ligands) can be reduced because particle-by-particle interactions are spatially or temporarily controlled on LNTs.

Third, integration of lipid bilayers with DNA nanostructures may provide a path toward a new type of molecular circuits. For example, by tethering DNA origami scaffolds that contain spatially localized DNA circuits to an SLB, a dynamic network of inter-origami interactions can be utilized. The principles used to construct or connect nanoparticle logic gates (interface programming and network programming) can be applied to construct a DNA origami scaffold circuit. This method may enable the implementation of more complex and even practical molecular computation.

Despite such potentials, further scaling up complexity of nanoparticle circuits on LNT will lead to a challenge because the input (DNA) and output (state-switching floaters) are of different forms. Currently, this intrinsic difference limits the construction of arbitrarily large circuits. This challenge can be potentially solved in two ways.

First, introducing new modes of nanoparticle reaction and ligand activation, such as dynamic reconfiguration, communication, DNA walker, and light-induced DNA release will be able to provide a much broader design space for circuit design, as this allows the nanoparticle interface and network to be controlled by more sophisticated mechanisms.

Second, increasing the number of different nanoparticle computing units per LNT will enhance the overall processing power of LNT. The different nanoparticle computing units can operate either in a parallel manner or assembled into a combinational circuit through network programming. This approach is similar to how an increase in integrated circuit density has led to the improvement in computing capacity of silicon-based computers. Ultimately, each nanoparticle independently performs a different computation on its own by using parallel processing.

As spatial constraints such as localization and encapsulation result in the modular execution of molecular circuits tethering nanoparticles to a lipid bilayer provides a systematic method to build complex nanoparticle circuits. The LNT-based approach according to the present disclosure may play a pivotal role in constructing highly functional "autonomous" nanostructures. Such devices may have broad impacts on molecular diagnostics and smart sensors. A nanosystem in the device should be able to exploit internal computational algorithms to sense multiple stimuli and trigger the most appropriate responses.

In addition, information-processing nanosystems on lipid bilayers can be applied to reconstituting artificial cell-cell junctions and used as tools for studying membrane-associated phenomenon in living cells. Unlike existing methods that rely on immutable materials such as patterned membranes, the LNT-based approach may allow networks of nanostructures on an SLB to autonomously form clusters or structural motifs and to be analyzed in response to signaling molecules from the cells. Allowing each nano- and cellular system to communicate with one another, such "active" SLB-cell junctions can also be employed to test how individual theranostic nanorobots navigate complex and dynamic environments.

A Supported Lipid Bilayer (SLB) "Chip" for Use in the Lipid Nanotablet Shown in FIG. 1A can be Manufactured as Follows.

A lipid solution (in chloroform) was mixed in a round-bottomed flask, a mixture containing diol-oil phosphatidylcholine (DOPC) at 97.2 mol %, biotinylated dioleoylphosphatidylethanolamine (DOPE) at 0.3 mol %, and poly(ethylene glycol) (1K)-DOPE at 2.5 mol % was obtained. The chloroform was removed by a rotary evaporator, and a lipid film formed inside the flask was completely dried for 15 minutes under a $N_2$ stream. The dried mixture was resuspended in deionized water (DI water) so that the total concentration became 2 mg/mL. For the obtained lipid solution, a freeze-thaw cycle was repeated 3 times at a temperature between 78° C. and 40° C. The lipid solution obtained as described above can be stored in a liquid nitrogen tank for up to 2 weeks. The lipid solution was extruded 11 times at 30° C. through a polycarbonate membrane having 100 nm pores, and then subjected to ultrasonic wave treatment for 15 minutes to produce small unilamellar vesicles (SUVs) from the lipid solution. The SUV solution obtained as described above was stored at 4° C. until use.

SLBs were formed by a vesicle fusion method inside a glass chamber composed of upper and lower glass and parafilm spacers (4 mm×50 mm×200 μm).

The operating volume of the glass chamber is less than 40 uL (~40 uL). After washing an upper slideglass (Paul Marienfeld GmbH) having an inflow port and an outflow port by ultrasonic wave treatment for 5 minutes in deionized water and piranha etching for 2 minutes, SLB formation was blocked by passivating with 10 mg/ml of bovine serum albumin (BSA) dissolved in 150 mM NaCl phosphoric acid buffer saline (1× PBS). The lower coverglass (Co. KG, Germany) was subjected to ultrasonic wave treatment in acetone and deionized water for 5 minutes, immersed in a piranha etching solution for 2 minutes, and washed, and then cleaned with deionized water. After that, a two-fold parafilm spacer was placed between two glass slides and heat-sealed at 100° C. The newly extruded SUV solution was diluted to 1 mg/mL in a 1× PBS solution, and then subjected to ultrasonic wave treatment for 15 minutes until use. SLB was formed by introducing a vesicle solution into a flow chamber at 30° C. After 60 minutes, the flow chamber was gently washed with deionized water (2 times) and 1× PBS. Then, 100 μg/mL BSA dissolved in 1× PBS was used to block defects on the SLB surface for 45 minutes. 17 nM streptavidin (STV) dissolved in 1× PBS was injected into the flow chamber to transform biotinylated lipids for 45 minutes. After BSA blocking and streptavidin transformation, the flow cell in the flow chamber was washed twice with 1× PBS. The flow chamber with STV-modified SLB can be stored in a humidified refrigerator at 4° C. for up to 3 days. Air-bubbles must be avoided in all processes related to the lipid chamber.

The Synthesis Method of Nanoparticles is as Follows.

Gold nanorods are synthesized with silver nanoshells, gold nanospheres and silver nanospheres on gold seeds that mainly exhibit red R, green G, and blue B scattering signals, and they were used throughout the following example. First, a gold nano-rod with an aspect ratio of 4 was synthesized by a seed-mediated growth mechanism. Seeds were mixed with a $HAuCl_4 \cdot 3H_2O$ solution (5 mL, 0.5 mM) with a cetyltrimethylammonium bromide (CTAB) solution (5 mL, 0.2 M), and then an ice-cooled $NaBH_4$ solution (600 μl, 10 mM) was rapidly injected. The seed solution was left for 2 hours after the reduction step. The $HAuCl_4 \cdot 3H_2O$ solution (5 mL, 1 mM) was mixed with the CTAB solution (5 mL, 0.2 M), and then an L-ascorbic acid solution (70 μl, 78 mM) was added after adding a $AgNO_3$ solution (250 μl, 4 mM). 12 μl of the seed solution was added thereto and gently mixed. The obtained solution was incubated at 60° C. for 4 hours, centrifuged, and re-dispersed in deionized water 3 times. A gold nanorod solution (1 mL, 100 nM) was mixed with a cetyltrimethylammonium chloride (CTAC) solution (1 mL, 10 mM), $AgNO_3$ (1 mL, 0.2 mM), and ascorbic acid (1 mL, 50 mM), and then the gold nanorod was coated with about 5 nm silver shells. After incubation at 60° C. for 4 hours, the solution was washed by centrifugation, the supernatant was removed, and then re-dispersed three times in deionized water to obtain red (R) nanoparticles. Gold nanoparticles (50 nm) of a spherical shape were purchased from BBI Solutions (Cardiff, UK) and used as green (G) nanoparticles. Blue (B) nanoparticles were prepared by growing a 17 nm silver shell on a 20 nm spherically shaped gold seed. A sodium ascorbate solution (100 μl, 50 mM) was rapidly injected to a mixture containing 150 pM 20-nm gold nanoparticles, 0.2% polyvinylpyrrolidone (PVP), and 0.24 mM nitric acid to form a silver shell on the gold seed.

A Manufacturing Method of Nanoparticle Receptors and Floaters is as Follows.

Synthetic DNA oligonucleotides (Bioneer, Daejeon, Korea) having a thiol functional group were reduced with a solution of 100 mM dithiothreitol (DTT) dissolved in 100 mM pH 8.0 phosphate buffers (PB) for 1 hour, and then separated by using a NAP-5 column (GE Healthcare, Buckinghamshire, UK). The sequence, modification, and density of the surface DNA ligand used in the following example are summarized in Table 2 to Table 12. Table 2 to Table 12 show the sequence of thiolated DNA strands used in functionalizing nanoparticles (r: a spacer used in a ligand and a linker having a surface density of 5' thiol group of a thiolated ENA strand: a space used in a ligand and a linker having 5'-A15 to $EG_6$-3'3' thiol group: and 5'-EG to $A_{15}$-3' sequence numbers disclosed in the following tables correspond to sequences of ligands and linkers excluding spacers).

TABLE 2

| Logic Circuit | NP (Nano Particle) | Ligand Sequence | SEQ ID NO | r (%) | Linker Sequence | SEQ ID NO | r (%) |
|---|---|---|---|---|---|---|---|
| Single-input Assembly YES gate | $R_a$ (G-NR) | 5'-CTATAAACTATTTC CTTTGCTATT-Spacer-SH-3' | 1 | 65 | 5'-biotin-CTCTCTGCCTCGTTC AGACAAAACTCATCCTACT-Spacer-SH-3' | 25 | 35 |
|  | $F_a$ (G-NF) | 5'-HS-Spacer-CGCAAAGACACTAATAA CAAATTC-3' | 2 | 99.5 | 5'-HS-Spacer-TTACTACACTGT CACTGATCATCGCATGCTATAC-biotin-3' | 26 | 0.5 |
| Single-input Disassembly YES gate | $R_d$ (G-NR) | 5'-CTATAAACTATTTC CTTTGCTATT-Spacer-SH-3' | 1 | 65 | 5'-biotin-CTCTCTGCCTCGTTC AGACAAAACTCATCCTACT-Spacer-SH-3' | 27 | 35 |
|  | $F_d$ (G-NF) | 5'-SH-Spacer-CGCAAAGACACTAATAA CAAATTC-3' | 2 | 99.5 | 5'-HS-Spacer-TTACTACACTGT CACTGATCATCGCATGCTATAC-biotin-3' | 28 | 0.5 |

TABLE 3

| Logic Circuit | NP | Ligand Sequence | SEQ ID NO | r (%) | Linker Sequence | SEQ ID NO | r (%) |
|---|---|---|---|---|---|---|---|
| Two-input Assembly AND gate | $R_1$ (G-NR) | 5'-HS-Spacer-ACTTCAG AAAGTGTACTTGTAGATTCC AAATCTACTACAAGTACACT TTG-3' | 3 | 65 | 5'-HS-Spacer-TTACTAC ACTGTCACTGATCATCGCAT GCTATAC-biotin-3' | 28 | 35 |
|  | $F_1$ (G-NF) | 5'-HS-Spacer-CTTCTAA GTACACTTTGTAGGATTTCC AACTAACCTACAAAGTGTA CTT-3' | 4 | 65 | 5'-HS-Spacer-TTACTAC ACTGTCACTGATCATCGCAT GCTATAC biotin-3' | 28 | 0.5 |
|  |  | 5'-HS-Spacer-TTACTAC ACTGTCACTGATCATCGCAT GCTATAC-3' | 5 | 34.5 |  |  |  |
| Two-input Assembly OR gate | $R_2$ (G-NR) | 5'-CAAATAACTAATACACA TTCATCT-Spacer-SH-3' | 6 | 32.5 | 5'-biotin-CTCTCTGCCT CGTTCAGACAAAACTCATCC TACT-Spacer-SH-3' | 27 | 35 |
|  |  | 5'-CATAATCTATAATCATC CTCATAA-Spacer-SH-3' | 7 | 32.5 |  |  |  |
|  | $F_2$ (B-NF) | 5'-HS-Spacer-TACTCAC TATCTAAAAACAATTAC-3' | 8 | 49.75 | 5'-HS-Spacer-TTACTAC ACTGTCACTGATCATCGCAT GCTATAC-biotin-3' | 28 | 0.5 |
|  |  | 5'-HS-Spacer-CTTAGCC TAACATTTTCTAAATAC-3' | 9 | 49.75 |  |  |  |
| Two-input Disassembly AND gate | $R_3$ (B-NR) | 5'-CAAATAACTAATACACA TTCATCT-Spacer-SH-3' | 10 | 25 | 5'-biotin-CTCTCTGCCT CGTTCAGACAAAACTCATCC TACT-Spacer-SH-3' | 27 | 50 |
|  |  | 5'-CATAATCTATAATCATC CTCATAA-Spacer-SH-3' | 7 | 25 |  |  |  |
|  | $F_3$ (G-NF) | 5'-HS-Spacer-TACTCAC TATCTAAAAACAATTAC-3' | 8 | 49.75 | 5'-HS-Spacer-TTACTAC ACTGTCACTGATCATCGCAT GCTATAC-biotin-3' | 28 | 0.5 |
|  |  | 5'-HS-Spacer-CTTAGCC TAACATTTTCTAAATAC-3' | 9 | 49.75 |  |  |  |
| Two-input Disassembly OR gate | $R_4$ (B-NR) | 5'-CTATAAACTATTTCCTT TGCTATT-Spacer-SH-3' | 1 | 50 | 5'-biotin-CTCTCTGCCT CGTTCAGACAAAACTCATCC TACT-Spacer-SH-3' | 27 | 50 |
|  | $F_4$ (B-NF) | 5'-HS-Spacer-CGCAAAG A CACTAATAACAAATT C-3' | 11 | 99.5 | 5'-HS-Spacer-TTACTAC ACTGTCACTGATCATCGCAT GCTATAC-biotin-3' | 5 | 0.5 |
| Two-input Assembly AND gate | $R_1$ (G-NR) | 5'-HS-Spacer-ACTTCAC AAAGTGTACTTGTAGATTCA AATCTACTACAAGTACACT TTG-3' | 3 | 65 | 5'-HS-Spacer-TTACTAC ACTGTCACTGATCATCGCAT GCTATAC-biotin-3' | 28 | 35 |
|  | $F_1$ (G-NF) | 5'-HS-Spacer-CTTCTAA GTACACTTTGTAGGATTTCC AACTAACCTACAAAGTGTA CTT-3' | 4 | 65 | 5'-HS-Spacer-TTACTAC ACTGTCACTGATCATCGCAT GCTATAC-biotin-3' | 28 | 0.5 |
|  |  | 5'-HS-Spacer-TTACTAC ACTGTCACTGATCATCGCAT GCTATAC-3' | 5 | 34.5 |  |  |  |

TABLE 3-continued

| Logic Circuit | NP | Ligand Sequence | SEQ ID NO | r (%) | Linker Sequence | SEQ ID NO | r (%) |
|---|---|---|---|---|---|---|---|
| Two-input Assembly OR gate | $R_2$ (G-NR) | 5'-CAAATAACTAATACACA TTCATCT-Spacer-SH-3' | 6 | 32.5 | 5'-biotin-CTCTCTGCCT CGTTCAGACAAAACTCATCC TACT-Spacer-SH-3' | 27 | 35 |
| | | 5'-CATAATCTATAATCATC CTCATAA-Spacer-SH-3' | 7 | 32.5 | | | |
| | $F_2$ (B-NF) | 5'-HS-Spacer-TACTCAC TATCTAAAAACAATTAC-3' | 8 | 49.75 | 5'-HS-Spacer-TTACTAC ACTGTCACTGATCATCGCAT GCTATAC-biotin-3' | 28 | 0.5 |
| | | 5'-HS-Spacer-CTTAGCC TAACATTTTCTAAATAC-3' | 9 | 49.75 | | | |
| Two-input Disassembly AND gate | $R_3$ (B-NR) | 5'-CAAATAACTAATACACA TTCATCT-Spacer-SH-3' | 10 | 25 | 5'-biotin-CTCTCTGCCT CGTTCAGACAAAACTCATCC TACT-Spacer-SH-3' | 27 | 50 |
| | | 5'-CATAATCTATAATCATC CTCATAA-Spacer-SH-3' | 7 | 25 | | | |
| | $F_3$ (G-NF) | 5'-HS-Spacer-TACTCAC TATCTAAAAACAATTAC-3' | 8 | 49.75 | 5'-HS-Spacer-TTACTAC ACTGTCACTGATCATCGCAT GCTATAC-biotin-3' | 28 | 0.5 |
| | | 5'-HS-Spacer-CTTAGCC TAACATTTTCTAAATAC-3' | 9 | 49.75 | | | |
| Two-input Disassembly OR gate | $R_4$ (B-NR) | 5'-CTATAAACTATTTCCTT TGCTATT-Spacer-SH-3' | 1 | 50 | 5'-biotin-CTCTCTGCCT CGTTCAGACAAAACTCATCC TACT-Spacer-SH-3' | 27 | 50 |
| | $F_4$ (B-NF) | 5'-HS-Spacer-CGCAAAG ACTAATAACAAATTC-3' | 11 | 99.5 | 5'-HS-Spacer-TTACTAC ACTGTCACTGATCATCGCAT GCTATAC-biotin-3' | 5 | 0.5 |

TABLE 4-1

| Logic Circuit | NP | Ligand Sequence | SEQ ID NO | r (%) | Linker Sequence | SEQ ID NO | r (%) |
|---|---|---|---|---|---|---|---|
| Two-input Disassembly INHIBIT gene | $R_1$ (G-NR) | 5'-CAAATAACTAATACACA TTCATCT-Spacer-SH-3' | 10 | 32.5 | 5'-biotin-CTCTCTGCCT CGTTCAGACAAAACTCATCC TACT-Spacer-SH-3' | 27 | 35 |
| | | 5'-CATAATCTATAATCATC CTCATAA-Spacer-SH-3' | 7 | 32.5 | | | |
| | $F_1$ (G-NF) | 5'-HS-Spacer-TACTCAC TATCTAAAAACAATTAC-3' | 8 | 49.75 | 5'-HS-Spacer-TTACTAC ACTGTCACTGATCATCGCAT GCTATAC-biotin-3' | 26 | 0.5 |
| | | 5'-HS-Spacer-CTTAGCC TAACATTTTCTAAATAC-3' | 12 | 49.75 | | | |
| Six-input Disassembly gate (fan-in) | $R_2$ (G-NR) | 5'-CTATAAACTATTTCCTT TGCTATT-Spacer-SH-3' | 1 | 22 | 5'-biotin-CTCTCTGCCT CGTTCAGACAAAACTCATCC TACT-Spacer-SH-3' | 27 | 34 |
| | | 5'-CAAATAACTAATACACA TTCATCT-Spacer-SH-3' | 10 | 22 | | | |
| | | 5'-CATAATCTATAATCATC CTCATAA-Spacer-SH-3' | 7 | 22 | | | |
| | $F_2$ (G-NF) | 5'-HS-Spacer-CGCAAAG ACTAATAACAAATTC-3' | 11 | 33.2 | 5'-HS-Spacer-TTACTAC ACTGTCACTGATCATCGCAT GCTATAC-biotin-3' | 26 | 0.4 |
| | | 5'-HS-Spacer-TACTCAC TATCTAAAAACAATTAC-3' | 8 | 33.2 | | | |
| | | 5'-HS-Spacer-CTTAGCC TAACATTTTCTAAATAC-3' | 9 | 33.2 | | | |
| Two-input Disassembly Gate with three outputs (fan-out) | $R_3$ (G-NR) | 5'-CAAATAACTAATACACA TTCATCT-Spacer-SH-3' | 10 | 32.5 | 5'-biotin-CTCTCTGCCT CGTTCAGACAAAACTCATCC TACT-Spacer-SH-3' | 29 | 35 |
| | | 5'-CATAATCTATAATCATC CTCATAA-Spacer-SH-3' | 7 | 32.5 | | | |
| | $F_3$ (R-NF) | 5'-HS-Spacer-TACTCAC TATCTAAAAACAATTAC-3' | 8 | 49.75 | 5'-HS-Spacer-TTACTAC ACTGTCACTGATCATCGCAT GCTATAC-biotin-3' | 28 | 0.5 |
| | | 5'-HS-Spacer-CTTAGCC TAACATTTTCTAAATAC-3' | 9 | 49.75 | | | |
| | $F_4$ (G-NF) | 5'-HS-Spacer-TACTCAC TATCTAAAAACAATTAC-3' | 8 | 49.75 | 5'-HS-Spacer-TTACTAC ACTGTCACTGATCATCGCAT GCTATAC-biotin-3' | 26 | 0.5 |
| | | 5'-HS-Spacer-CTTAGCC TAACATTTTCTAAATAC-3' | 9 | 49.75 | | | |

TABLE 4-1-continued

| Logic Circuit | NP | Ligand Sequence | SEQ ID NO | r (%) | Linker Sequence | SEQ ID NO | r (%) |
|---|---|---|---|---|---|---|---|
| | $F_5$ (B-NF) | 5'-HS-Spacer-TACTCAC TATCTAAAACAATTAC-3' | 8 | 49.75 | 5'-HS-Spacer-TTACTAC ACTGTCACTGATCATCGCAT GCTATAC-biotin-3' | 30 | 0.5 |
| | | 5'-HS-Spacer-CTTAGCC TAACATTTTCTAAATAC-3' | 9 | 49.75 | | | |

TABLE 5

| Logic Circuit | NP | Ligand Sequence | SEQ ID NO | r (%) | Linker Sequence | SEQ ID NO | r (%) |
|---|---|---|---|---|---|---|---|
| AND-AND Cascade | $R_1$ (G-NR) | 5'-CAAATAACTAATACACA TTCATCT-Spacer-SH-3' | 10 | 32.5 | 5'-biotin-CTCTCTGCCT CGTTCAGACAAAACTCATCC TACT-Spacer-SH-3' | 25 | 35 |
| | | 5'-CATAATCTATAATCATC CTCATAA-Spacer-SH-3' | 7 | 32.5 | | | |
| | $F_1$ (G-NF) | 5'-HS-Spacer-TACTCAC TATCTAAAACAATTAC-3' | 8 | 33.2 | 5'-HS-Spacer-TTACTAC ACTGTCACTGATCATCGCAT GCTATAC-biotin-3' | 26 | 0.4 |
| | | 5'-HS-Spacer-CTTAGCC TAACATTTTCTAAATAC-3' | 9 | 33.2 | | | |
| | | 5'-HS-Spacer-CGCAAAG ACACTAATAACAAATTC-3' | 2 | 33.2 | | | |
| | $R_2$ (B-NR) | 5'-CTATAAACTATTTCCTT TGCTATT-Spacer-SH-3' | 1 | 50 | 5'-biotin-CTCTCTGCCT CGTTCAGACAAAACTCATCC TACT-Spacer-SH-3' | 27 | 50 |
| AND-OR Cascade | $R_3$ (B-NR) | 5'-CATAATCTATAATCATC CTCATAA-Spacer-SH-3' | 7 | 25 | 5'-biotin-CTCTCTGCCT CGTTCAGACAAAACTCATCC TACT-SH-3' | 25 | 50 |
| | | 5'-CATTATCATATAACTCA ACGTCAC-Spacer-SH-3' | 13 | 25 | | | |
| | $F_2$ (G-NF) | 5'-HS-Spacer-CTTAGCC TAACATTTTCTAAATAC-3' | 9 | 49.75 | 5'-HS-TTACTACACTGTCA CTGATCATCGCATGCTATA C-biotin-3' | 31 | 0.5 |
| | | 5'-HS-Spacer-AATCAGC ATCCTATTACATAATTC-3' | 14 | 49.75 | | | |
| | $R_4$ (G-NR) | 5'-CTATAAACTATTTCCTT TGCTATT-Space-SH-3' | 1 | 65 | 5'-biotin-CTCTCTGCCT CGTTCAGACAAAACTCATCC TACT-PEG$_6$-A$_{15}$-(CH$_2$)$_3$- SH-3' | 25 | 35 |
| | $F_3$ (G-NF) | 5'-HS-Spacer-CGCAAAG ACACTAATAACAAATTC-3' | 2 | 99.5 | 5'-HS-TTACTACACTGTCA CTGATCATCGCATGCTATA C-biotin-3' | 31 | 0.5 |

TABLE 6

| Logic Circuit | NP | Ligand Sequence | SEQ ID NO | r (%) | Linker Sequence | SEQ ID NO | r (%) |
|---|---|---|---|---|---|---|---|
| Multiplexer | $R_1$ (B-NR) | 5'-HS-Spacer-CGCAAAG ACACTAATAACAAATTC-3' | 2 | 32.5 | 5'-HS-TTACTACACTGTCA CTGATCATCGCATGCTATA C-biotin-3 | 32 | 35 |
| | | 5'-HS-Spacer-CTGCACA TTAGTATTAGTTATTTG | 15 | 32.5 | | | |
| | $F_1$ (G-NF) | 5'-CTATAAACTATTTCCTT TGCTATT-Spacer-SH-3' | 1 | 49.75 | 5'-biotin-CTCTCTGCCT CGTTCAGACAAAACTCATCC TACT-SH-3' | 27 | 0.5 |
| | | 5'-GTAATTGTTTTTAGTAT TCTTCTC-Spacer-SH-3' | 16 | 49.75 | | | |
| | $R_2$ (G-NR) | 5'-CAAATAACTAATACACA TTCATCT-Spacer-SH-3' | 10 | 32.5 | 5'-biotin-CTCTCTGCCT CGGTAGACAAAACTCATCCT ACT-SH-3' | 25 | 35 |
| | | 5'-CATAATCTATAATCATC CCTCATAA-Spacer- SH-3' | 17 | 32.5 | | | |

TABLE 6-continued

| Logic Circuit | NP | Ligand Sequence | SEQ ID NO | r (%) | Linker Sequence | SEQ ID NO | r (%) |
|---|---|---|---|---|---|---|---|
| | $R_2$ (G-NF) | 5'-HS-Spacer-TACTCAC TATCTAAAAACAATTAC-3' 5'-HS-Spacer-CTTAGCC TAACATTTTCTAAATAC-3' | 8 | 49.75 | 5'-HS-TTACTACACTGTCA CTGATCATCGCATGCTATA C-biotin-3 | 32 | 0.5 |

TABLE 7

| Logic Circuit | NP | Ligand Sequence | SEQ ID NO | r (%) | Linker Sequence | SEQ ID NO | r (%) |
|---|---|---|---|---|---|---|---|
| Two-input Assembly AND gate | $R_1$ (G-NR) | 5'-HS-Spacer-ACTTCAC AAAGTGTACTTGTAGATTCC AAATCTACTACAAGTACACT TTG-3' | 3 | 65 | 5'-HS-Spacer-TTACTAC ACTGTCACTGATCATCGCAT GCTATAC-biotin-3' | 26 | 35 |
| | $F_1$ (G-NF) | 5'-HS-Spacer-CTTCTAA GTACACTTTGTAGGATTTCC AACTAACCTACAAAGTGTAC TT-3' | 18 | 49.75 | 5'-HS-Spacer-TTACTAC ACTGTCACTGATCATCGCAT GCTATAC-biotin-3' | 26 | 0.5 |
| | | 5'-HS-Spacer-CTTAGCC TAACATTTTCTAAATAC-3' | 9 | 49.75 | | | |

TABLE 8

| Logic Circuit | NP | Ligand Sequence | SEQ ID NO | r (%) | Linker Sequence | SEQ ID NO | r (%) |
|---|---|---|---|---|---|---|---|
| Two-input Assembly AND gate | $R_1$ (G-NR) | 5'-CATAATCTATAATC ATCCTCATAA-Spacer-SH-3' | 7 | 65 | 5'-biotin-CTCTCTGCCTCGTT CAGACAAAACTCATCCTAC T-Spacer-SH-3' | 27 | 35 |
| | $F_1$ (G-NF) | 5'-HS-Spacer-CTTCTA AAG TAC ACTTTG TAGG ATTTC CAACT AA CCTA CAAAGT GTA CTT-3' | 19 | 49.75 | 5'-HS-Spacer-TTACTACACTG TCACTGATCATCGCATGCT ATAC-biotin-3' | 26 | 0.5 |
| | | 5'-HS-Spacer-CTTAGCCTAA CATTTTCTAAATAC-3' | 9 | 49.75 | | | |

TABLE 9

| Dual-rail NAND | NP | Ligand Sequence | SEQ ID NO | r (%) | Linker Sequence | SEQ ID NO | r (%) |
|---|---|---|---|---|---|---|---|
| Two-input Assembly OR ($Y^0$) | $R_1$ (B-NR) | 5'-CATAATCTATAATC ATCCTCATAA-Spacer-SH-3' | 7 | 25 | 5'-biotin-CTCTCTGCCTCGTT CAGACAAAACTCATCCTAC T-Spacer-SH-3' | 27 | 50 |
| | | 5'-CATTATCATATAACTCA ACGTCAC-Spacer-SH-3' | 20 | 25 | | | |

TABLE 9-continued

| Dual-rail NAND | NP | Ligand Sequence | SEQ ID NO | r (%) | Linker Sequence | SEQ ID NO | r (%) |
|---|---|---|---|---|---|---|---|
| | $F_1$ (G-NF) | 5'-HS-Spacer-CTTAGCCTAA CATTTTCTAAATAC-3' | 9 | 49.75 | 5'-HS-Spacer-TTACTACACTG TCACTGATCATCGCATGCT ATAC-biotin-3' | 26 | 0.5 |
| | | 5'-HS-Spacer-AATCAGCA TCCTATTACATAATTC-3' | 21 | 49.75 | | | |
| Two-input Disassembly OR ($Y^1$) | $R_2$ (G-NR) | 5'-CTATAAACTATTTC CTTTGCTATT-Spacer-SH-3' | 1 | 32.5 | 5'-biotin-CTCTCTGCCTCGTT CAGACAAAACTCATCCTAC T-Spacer-SH-3' | 27 | 35 |
| | | 5'-CAAATAACTAATAC ACATTCATCT-Spacer-SH-3' | 10 | 32.5 | | | |
| | $F_2$ (G-NF) | 5'-HS-Spacer-CGCAAAGAC A CTAATAACAAATTC-3' | 22 | 49.75 | 5'-HS-Spacer-TTACTACACTG TCACTGATCATCGCATGCT ATAC-biotin-3' | 26 | 0.5 |
| | | 5'-HS-Spacer-TACTCACTAT CTAAAAACAATTAC-3' | 8 | 49.75 | | | |

TABLE 10

| Logic Circuit | NP | Ligand Sequence | SEQ ID NO | r (%) | Linker Sequence | SEQ ID NO | r (%) |
|---|---|---|---|---|---|---|---|
| CR-AND Cascade | $R_1$ (G-NR) | 5'-CATAATCTATAATC ATCCTCATAA-Spacer-SH-3' | 7 | 65 | 5'-biotin-CTCTCTGCCTCGTT CAGACAAAACTCATCCTAC T-Spacer-SH-3' | 27 | 35 |
| | $F_1$ (G-NF) | 5'-HS-Spacer-CTTAGCCTAA CATTTTCTAAATAC-3' | 9 | 49.75 | 5'-HS-Spacer-TTACTACACTG TCACTGATCATCGCATGCT ATAC-biotin-3' | 26 | 0.5 |
| | | 5'-HS-Spacer-CGCAAAGA CA CTAATAACAAATTC-3' | 11 | 49.75 | | | |
| | $R_2$ (B-NR) | 5'-CTATAAACTATTTC CTTTGCTATT-Spacer-SH-3' | 1 | 50 | 5'-biotin-CTCTCTGCCTCGTT CAGACAAAACTCATCCTAC T-Spacer-SH-3' | 27 | 50 |

TABLE 11

| Logic Circuit | NP | Ligand Sequence | SEQ ID NO | r (%) | Linker Sequence | SEQ ID NO | r (%) |
|---|---|---|---|---|---|---|---|
| INHIBIT-AND Cascade | $R_1$ (G-NR) | 5'-CAAATAACTAATAC ACATTCATCT-Spacer-SH-3' | 10 | 32.5 | 5'-biotin-CTCTCTGCCTCGTT CAGACAAAACTCATCCTAC T-Spacer-SH-3' | 27 | 35 |
| | | 5'-CATAATCTATAATC ATCCTCATAA-Spacer-SH-3' | 7 | 32.5 | | | |
| | $F_1$ (G-NF) | 5'-HS-Spacer-TACTCACTAT CTAAAAACAATTAC-3' | 8 | 33.2 | 5'-HS-Spacer-TTACTACACTG TCACTGATCATCGCATGCT ATAC-biotin-3' | 26 | 0.4 |
| | | 5'-HS-Spacer-CTTAGCCTAA CATTTTCTAAATAC-3' | 9 | 33.2 | | | |
| | | 5'-HS-Spacer-CGCAAAGA CA CTAATAACAAATTC-3' | 11 | 33.2 | | | |

TABLE 11-continued

| Logic Circuit | NP | Ligand Sequence | SEQ ID NO | r (%) | Linker Sequence | SEQ ID NO | r (%) |
|---|---|---|---|---|---|---|---|
| | R$_2$ (B-NR) | 5'-CTATAAACTATTTC CTTTGCTATT-Spacer-SH-3' | 1 | 50 | 5'-biotin-CTCTCTGCCTCGTT CAGACAAAACTCATCCTAC T-Spacer-SH-3' | 27 | 50 |

TABLE 12

| Logic Circuit | NP | Ligand Sequence | SEQ ID NO | r (%) | Linker Sequence | SEQ ID NO | r (%) |
|---|---|---|---|---|---|---|---|
| OR-OR Cascade | R$_1$ (B-NR) | 5'-CATAATCTATAATC ATCCTCATAA-Spacer-SH-3' | 7 | 50 | 5'-biotin-CTCTCTGCCTCGT TCAGACAAAACTCATCCTA CT-Spacer-SH-3' | 29 | 50 |
| | F$_1$ (G-NF) | 5'-HS-Spacer-CTTAGCCTAA CATTTTCTAAATAC-3' | 9 | 99.5 | 5'-HS-Spacer-TTACTACACTG TCACTGATCATCGCATGCT ATAC-biotin-3' | 26 | 0.5 |
| | R$_2$ (G-NR) | 5'-CATTATCATATAAC TCA ACGTCAC-Spacer-SH-3' | 23 | 65 | 5'-biotin-CTCTCTGCCTCGT TCAGACAAAACTCATCCTA CT-Spacer-SH-3' | 29 | 35 |
| | F$_2$ (G-NF) | 5'-HS-Spacer-AATCAGC ATC CTATTACATAATTC-3' | 24 | 99.5 | 5'-HS-Spacer-TTACTACACTG TCACTGATCATCGCATGCT ATAC-biotin-3' | 26 | 0.5 |

The mixture of thiolated DNA was incubated with nanoparticles (final concentration: 15 PM) for 1 hour at room temperature. The entire concentration of thiolated DNA was used so as to exceed 14,400 times and 19,200 times with respect to R nanoparticles and G nanoparticles, respectively. The ratios of biotinylated DNA linker to the entire surface DNA ligand were 0.5% (w/v), 0.5% (w/v), 0.5% (w/v), 35% (w/v), and 50% (w/v), respectively with respect to a red nano-floater (R-NF), a green nano-floater (G-NF), a blue nano-floater (B-NF), a green nano-receptor (G-NR), and a blue nano-receptor (B-NR). After that, in the case of gold nanorods (R nanoparticles), the solution was adjusted to 0.1% (w/v) PVP in 10 mM PB, and in the case of spherically shaped gold nanoparticles (G nanoparticles), the solution was adjusted to 0.1% (w/v) sodium dodecyl sulfate (SDS) in 10 mM PB, and the spherical shape was adjusted in a solution of 10 mM PB for nanoparticles (B nanoparticles). Three aliquots of a 1M NaCl, 0.1% SDS, and 10 mM PB salt solution were added at intervals of 1 hour so that the final concentration of NaCl was 0.3M. After each salt was added, the mixture was heated at 50° C. for 10 minutes and incubated at room temperature. Two hours after reaching the final concentration, the nanorod solution was centrifuge-washed and re-dispersed in 1× PBS. Another nanoparticle solution was incubated for 12 hours, centrifuge-washed, and re-dispersed in deionized water (spherical-shaped gold nanoparticles) or 1× PBS (spherical-shaped nanoparticles). Features of modified nanoparticles were observed by using a transmission electron microscope (JEM-2100, JEOL Ltd, Japan), a UV-Vis spectrophotometer (Agilent 8453, Agilent Technologies, USA), and a dark field microscope (Axiovert 200M, Carl Zeiss, Gottingen, Germany) (FIG. 3A to FIG. 3C). Single particle scattering signals from three nanoparticles were analyzed by correlated SEM-DFM images (FIG. 4A to FIG. 4C). Nanoparticles were loaded onto a glass substrate and imaged with a dark field microscope. After that, the same position was imaged by a field emission scanning electron microscope (FE-SEM, JSM-7600F, JEOL Ltd, Japan) after Pt coating (Cressington 108auto, Cressington Scientific Instruments Ltd, UK). TEM and FE-SEM measurements were performed at the National Center for Inter-University Research Facilities and Research Institute of Advanced Materials (all Seoul National University, Seoul).

Experimental Conditions for Hallmark Analysis of Nanoparticle Circuits on the Lipid Nanotablet are as Follows.

In order to completely assemble a lipid nanotablet, a solution containing DNA-modified nanoparticles with a biotinylated linker (1 to 10 pM) was introduced into a flow chamber of which a lower glass substrate was coated with a streptavidin-modified lipid bilayer surface. The solution was incubated for 1 to 5 minutes to obtain a desired particle density. Under these conditions, the particle density was linearly proportional to the incubation time (FIG. 8A and FIG. 8B). After loading the lipid nanotablet, it was washed twice with 1× PBS. After that, the tethered particles take DNA inputs contained in the 1× PBS buffer and function as logic gates. DNA input sequences and density, and experimental conditions for pre-dimerization (Disassembly gates) are summarized in Table 13 to Table 22. Table 13 to Table 22 show experimental conditions and DNA input sequences used in logic circuit computations (DNA sequence is disclosed in the direction from 5' to 3' N/A: not applicable).

TABLE 13

| Logic Circuit | Operation (input) | | | | Pre-dimerization | | |
|---|---|---|---|---|---|---|---|
| | Name | Sequence | SEQ ID NO | Condition | Sequence | SEQ ID NO | Condition |
| Single-input Assembly YES gate | $X_a$ | GAAATAGTTTATAG CTGCGACTGT GAATTTGTTATTAG | 33 | 20 nM, 15 min | | N/A | |
| Single-input Disassembly YES gate | $X_d$ | CTAATAACAAATTC ACAGTCGCAG CTATAAACTATTTC | 34 | 500 nM, 15 min | GAAATAGTTTATAG CTGCGACTGT GAATTTGTTATTAG | 33 | 10 nM, 15 min |

TABLE 14

| Logic Circuit | Operation (input) | | | | Pre-dimerization | | |
|---|---|---|---|---|---|---|---|
| | Name | Sequence | SEQ ID NO | Condition | Sequence | SEQ ID NO | Condition |
| Two-input Assembly AND gate | X1 | AGTTGGAAAT CCTACAAAGTGTA | 35 | 100 nM, 30 min | | N/A | |
| | X2 | GATTTGGAAT CTACAAGTACACT | 36 | 100 nM, 30 min | | | |
| Two-input Assembly OR gate | X3 | GTATTAGTTATTTG TAGACGTAGG GTAATTGTTTTTAG | 37 | 40 nM, 20 min | | N/A | |
| | X4 | GATTATAGATTATG TGTTAGCTGTGTA TTTAGAAAATG | 38 | 40 nM, 20 min | | | |
| Two-input Disassembly AND gate | X5 | CTAAAAACAATTAC CCTACGTCTACAA ATAACTAATAC | 39 | 500 nM, 15 min | GTATTAGTTATTTG TAGACGTAGGGT AATTGTTTTTAG | 40 | 40 nM, 15 min |
| | X6 | CATTTTCTAAATAC ACAGCTAACACAT AATCTATAATC | 41 | 500 nM, 15 min | GATTATAGATTATG TGTTAGCTGTGTA TTTAGAAAATG | 38 | 40 nM, 15 min |
| Two-input Disassembly OR gate | X7 | CTAATAACAAATTC CTCACGAACT | 42 | 500 nM, 15 min | GAAATAGTTTATAG CTGCGACTGTAGT TCGTGAGGAATTT GTTATTAG | 44 | 10 nM, 15 min |
| | X8 | ACAGTCGCAG CTATAAACTATTTC | 43 | 500 nM, 15 min | | | |

TABLE 15

| Logic Circuit | Operation (input) | | | | Pre-dimerization | | |
|---|---|---|---|---|---|---|---|
| | Name | Sequence | SEQ ID NO | Condition | Sequence | SEQ ID NO | Condition |
| Two-input Disassembly INHIBIT gate | X1 | CTAAAAACAATTAC CCTACGTCTA CAAATAACTAATAC | 45 | 200 nM, 15 min | GTATTAGTTATTTG TAGACGTAGG GTAATTGTTTTTAG | 37 | 10 nM, 15 min |
| | X2 | GATTATAGATTATG TGTTAGCTGT GTATTTAGAAAATG | 46 | 100 nM, 15 min | | | |
| Six-input Disassembly gate (fan-in) | X3 | CTAATAACAAATTC CTCACGAACT | 42 | 200 nM, 15 min | GAAATAGTTTATAG CTGCGACTGT AGTTCGTGAG GAATTTGTTATTAG | 47 | 20 nM, 15 min |
| | X4 | ACAGTCGCAG CTATAAACTATTTC | 43 | 200 nM, 15 min | | | |
| | X5 | CTAAAAACAATTAC CCTACGTCTA | 48 | 200 nM, 15 min | GTATTAGTTATTTG GAAGTGTATT | 50 | 20 nM, 15 min |

TABLE 15-continued

| Logic Circuit | Operation (input) | | | | Pre-dimerization | | |
|---|---|---|---|---|---|---|---|
| | Name | Sequence | SEQ ID NO | Condition | Sequence | SEQ ID NO | Condition |
| | X6 | AATACACTTC CAAATAACTAATAC | 49 | 200 nM, 15 min | TAGACGTAGG GTAATTGTTTTTAG | | |
| | X7 | CATTTTCTAAATAC ACAGCTAACA | 51 | 200 nM, 15 min | GATTATAGATTATG TGGGATCTGT | 53 | 20 nM, 15 min |
| | X8 | ACAGATCCCA CATAATCTATAATC | 52 | 200 nM, 15 min | TGTTAGCTGT GTATTTAGAAAATG | | |
| Two-input Disassembly Gate with three outputs (fan-out) | X9 | CTAAAAACAATTAC CCTACGTCTA CAAATAACTAATAC | 45 | 500 nM, 15 min | GTATTAGTTATTTG TAGACGTAGG GTAATTGTTTTTAG | 37 | 40 nM, 15 min |
| | X10 | CATTTTCTAAATAC ACAGCTAACA CATAATCTATAATC | 54 | 500 nM, 15 min | GATTATAGATTATG TGTTAGCTGT GTATTTAGAAAATG | 46 | 40 nM, 15 min |

TABLE 16

| Logic Circuit | Operation (input) | | | | Pre-dimerization | | |
|---|---|---|---|---|---|---|---|
| | Name | Sequence | SEQ ID NO | Condition | Sequence | SEQ ID NO | Condition |
| AND-AND Cascade (X1 AND X2) AND X3 | X1 | CTAAAAACAATTAC CCTACGTCTA CAAATAACTAATAC | 45 | 500 nM, 30 min | GTATTAGTTATTTG TAGACGTAGG GTAATTGTTTTTAG | 37 | 40 nM, 15 min |
| | X2 | CATTTTCTAAATAC ACAGCTAACA CATAATCTATAATC | 54 | 500 nM, 30 min | GATTATAGATTATG TGTTAGCTGT GTATTTAGAAAATG | 46 | 40 nM, 15 min |
| | X3 | GAAATAGTTTATAG CTGCGACTGT GAATTTGTTATTAG | 33 | 100 nM, 30 min | | N/A | |
| AND-OR Cascade (X4 AND X5) OR X6 | X4 | CATTTTCTAAATAC ACAGCTAACA CATAATCTATAATC | 54 | 500 nM, 15 min | GATTATAGATTATG TGTTAGCTGT GTATTTAGAAAATG | 46 | 40 nM, 15 min |
| | X5 | CTATTACATAATTC TGCATTCTTC CATTATCATATAAC | 55 | 500 nM, 15 min | GTTATATGATAATG GAAGAATGCA GAATTATGTAATAG | 56 | 40 nM, 15 min |
| | X6 | CTAATAACAAATTC ACAGTCGCAG CTATAAACTATTTC | 34 | 500 nM, 15 min | GAAATAGTTTATAG CTGCGACTGT GAATTTGTTATTAG | 33 | 10 nM, 15 min |

TABLE 17

| Logic Circuit | Operation (input) | | | | Pre-dimerization | | |
|---|---|---|---|---|---|---|---|
| | Name | Sequence | SEQ ID NO | Condition | Sequence | SEQ ID NO | Condition |
| Multiplexer | X7 | CTAATAACAAATTC ACAGTCGCAG CTATAAACTATTTC | 34 | 200 nM, 15 min | GAAATAGTTTATAG CTGCGACTGT GAATTTGTTATTAG | 33 | 10 nM, 15 min |
| | X8 | CATTTTCTAAATAC ACAGCTAACA CATAATCTATAATC | 54 | 500 nM, 15 min | GATTATAGATTATG TGTTAGCTGT GTATTTAGAAAATG | 46 | 40 nM, 15 min |

TABLE 17-continued

| Logic Circuit | Operation (input) | | | | Pre-dimerization | | |
|---|---|---|---|---|---|---|---|
| | Name | Sequence | SEQ ID NO | Condition | Sequence | SEQ ID NO | Condition |
| | Selector | TACTCACTAT CTAAAAACAATTAC CCTACGTCTA CAAATAACTAATAC | 57 | 500 nM, 15 min | GTATTAGTTATTTG TAGACGTAGG GTAATTGTTTTTAG ATAGTGAGTA (Sel*) | 37 | 40 nM, 15 min |
| | | | | | GTAATTGTTTTTAG (F5 protection) | 58 | 20 nM, 15 min |

TABLE 18

| Logic Circuit | Operation (input) | | | | Pre-dimerization | |
|---|---|---|---|---|---|---|
| | Name | Sequence | SEQ ID NO | Condition | Sequence | Condition |
| Two-input Assembly AND | X1 | AGTTGGAAATCCT ACAAAGTGTA | 59 | 100 nM, 15 min | N/A | |
| | X2 | GATTTGGAATCTAC AAGTACACT | 60 | 100 nM, 15 min | | |
| | X3 (Simple hybrid-ization) | GATTATAGATTATG TGTTAGCTGT GTAT TTAGAAAATG | 61 | 10 nM 15 min | | |

TABLE 19

| Dual-rail NAND gate | Operation (input) | | | | Pre-dimerization | | |
|---|---|---|---|---|---|---|---|
| | Name | Sequence | SEQ ID NO | Condition | Sequence | SEQ ID NO | Condition |
| Two-input Assembly OR ($Y^0$) | $X^1_1$ | GATTATAGATTATG TGTTAGCTGT GTATTTAGAAAATG | 46 | 50 nM, 10 min | N/A | | |
| | $X^1_2$ | GTTATATGATAATG GAAGAATGCA GAATTATGTAATAG | 56 | 50 nM, 10 min | | | |
| Two-input Disassembly OR ($Y^1$) | $X^0_1$ | CTAATAACAAATTC ACAGTCGCAG CTATAAACTATTTC | 34 | 500 nM, 10 min | GAAATAGTTTATAG CTGCGACTGT GAATTTGTTATTAG | 33 | 40 nM, 15 min |
| | $X^0_2$ | CTAAAAACAATTAC CCTACGTCTA CAAATAACTAATAC | 45 | 500 nM, 10 min | GTATTAGTTATTTG TAGACGTAGG GTAATTGTTTTTAG | 37 | 40 nM, 15 min |

TABLE 20

| Logic Circuit | Input | | | | Pre-dimerization | | |
|---|---|---|---|---|---|---|---|
| | Name | Sequence | SEQ ID NO | Condition | Sequence | SEQ ID NO | Condition |
| OR-AND Cascade (X1 OR X2) AND X3 | X1 | CATTTTCTAAATAC ACAGCTAACA | 51 | 500 nM, 15 min | GATTATAGATTATG TGGGATCTGT TGTTAGCTGT GTATTTAGAAAATG | 53 | 10 nM, 15 min |
| | X2 | ACAGATCCCA CATAATCTATAATC | 52 | 500 nM, 15 min | | | |
| | X3 | GAAATAGTTTATAG CTGCGACTGT GAATTTGTTATTAG | 33 | 100 nM, 15 min | | N/A | |

TABLE 21

| Logic Circuit | Input | | | | Pre-dimerization | | |
|---|---|---|---|---|---|---|---|
| | Name | Sequence | SEQ ID NO | Condition | Sequence | SEQ ID NO | Condition |
| INHIBIT-AND Cascade (X1 AND NOT X2) AND X3 | X1 | CTAAAAACAATTAC CCTACGTCTA CAAATAACTAATAC | 45 | 200 nM, 15 min | GTATTAGTTATTTG TAGACGTAGG GTAATTGTTTTTAG | 37 | 10 nM, 30 min |
| | X2 | GATTATAGATTATG TGTTAGCTGT GTATTTAGAAAATG | 46 | 100 nM, 15 min | | N/A | |
| | X3 | GAAATAGTTTATAG CTGCGACTGT GAATTTGTTATTAG | 33 | 100 nM, 15 min | | | |

TABLE 22

| Logic Circuit | Input | | | | Pre-dimerization | | |
|---|---|---|---|---|---|---|---|
| | Name | Sequence | SEQ ID NO | Condition | Sequence | SEQ ID NO | Condition |
| OR-OR Cascade (X1 OR X2) OR X3 | X1 | CATTTTCTAAATAC ACAGCTAACA | 51 | 500 nM, 15 min | GATTATAGATTATG TGGGATCTGT TGTTAGCTGT GTATTTAGAAAATG | 53 | 10 nM, 15 min |
| | X2 | ACAGATCCCA CATAATCTATAATC | 52 | 500 nM, 15 min | | | |
| | X3 | CTATTACATAATTC TGCATTCTTC CATTATCATATAAC | 55 | 500 nM, 15 min | GTTATATGATAATG GAAGAATGCA GAATTATGTAATAG | 56 | 10 nM, 15 min |

During dark-field imaging, 500 µl of an input solution was injected into the flow chamber to test the performance of each nanoparticle circuit at 25° C. Dark-field imaging was performed using a 40× objective lens (NA 0.6) and a dark-field microscope (Dail Systems, South Korea) equipped with an AxiCam HRC color camera on an optical table. Before the injection of the input solution, 31 images were acquired with a 200 ms imaging time step to confirm receptor nanoparticles. Circuit performance was recorded during and after the input solution injection at 2.5 s imaging intervals. Two image sequences were acquired in a fixed position.

The Dark-Field Time-Lapse Data Analysis Method is as Follows.

Image data obtained from time-lapse dark field images were processed and analyzed to quantify an output of the nanoparticle circuit. The quantification of the logic gate output is based on three steps: signal identification, tracking, and classification.

After time-lapse imaging with a dark field microscope, an optical scattering signal from the nanoparticle logic gate is verified and traced with ImageJ software and custom MATLAB code. In ImageJ, the image is first registered by the StackReg plug-in to correct transverse drift during imaging. The drift-corrected image sequence is processed by an image analysis algorithm capable of detecting and tracking particles. This procedure is described in FIG. 10A to FIG. 10C. The analysis process is as follows: (1) a signal detection step that enables segmentation of a spot (pixel) with a signal much higher than the threshold intensity and each nanoparticle signal is performed; (2) a particle localization step for determining a representative portion of each segmented signal is performed; and (3) a particle tracking step to identify receptor nanoparticles and classify signals is performed. In order to confirm the receptor position stably, a short video in the initial state (a video taken at a recording frame speed of 5 fps before input addition) was used. Subsequently, only receptor nanoparticles were tracked because the high particle density used in typical experimental conditions (more than 4000 nanoparticles captured in the field of view in the area (180 µm×180 µm)) interfered with reliable tracking of the mobile floater nanoparticles. After imaging, a portion of the field of view (128×128 μm$^2$) was selected for analysis because a non-uniform focal point and illumination across the field of view (usually observed along the image boundary) hindered acquisition of a consistent nanoparticle scattering signal profile.

Receptor signal tracking provided sufficient information for quantitative logic gates, as changes in the receptor signal depend on the signal of the floater with which the receptor interacts. (4) Finally, a scattering signal from 3×3 pixels around the local position of each receptor was sampled and averaged, and one average scattered signal was assigned to the receptor at a given time. This process is repeated for all receptors and frames, and thus traces of scattered signals were obtained for all receptors identified in the field of view. The stepwise change of the receptor signal due to the increase by the floater assembly and the increase by the floater disassembly was confirmed as assembly and disassembly events, respectively. Transient interactions (short and transient increase or decrease in receptor signal) were eliminated. Homebuilt code excludes intensity changes that do not last until imaging is complete. That is, only the receptors showing signal traces similar to the step function were identified as output produce particles.

Each assembly/disassembly event corresponding to the desired logic gate was classified according to how the receptor signal changes over time. Signal profiles of R, G, and B nanoparticles were used for classification (FIG. 11A to 11C). The classification process is as follows: (1) the receptors representing individual signal changes were identified from the signal traces of the receptors obtained from parallel imaging and analysis. The step-wise increase in the receptor signal indicated particle assembly, and the stepwise decrease in the receptor signal indicated particle disassembly (from the pre-dimerized nanoparticle pair). (2) For the assembly reaction, the signal of the indicated receptor was compared with the signal profile shown in FIG. 11A to FIG. 11C. Based on its position in the 3D signal profile, the receptor was classified into one of R, G, or B nanoparticle monomers. In the case of disassembly reaction, the original identity of the pre-dimer receptor can be determined by comparing the final signal of the displayed receptor with the 3D signal profile. (3) Since the signal change induced by the R, G, and B floaters is specific to a combination of particles involved in each reaction, the change in signal tracking was used to classify the floaters that interacted with the identified receptors. (4) A reaction type between the receptor-floater pair is completely classified by using the receptor type (obtained in step (2)) and signal change (obtained in step (3)).

In FIG. 7, (i) a signal trace with discrete stepwise reduction indicates a disassembly reaction, (ii) a signal after disassembly indicates B-NR, and (iii) the signal change represents a sharp decrease in G intensity (representing the release of G-NF from B-NR) and thus the disassembly of G-NF from B-NR can be discerned. In the experiment, the receptor-floater ratio was set to about 10 to minimize the formation of a multimer.

For each circuit, the number of receptors that generate a correct output was calculated over time. Recording continued until the kinetic plot became constant. The final number of events was normalized for each type of logical gate to minimize the effect of the variability of the particle population. For the assembly gate, the event count was standardized by the number of floaters detected in the initial 31 images. In the case of the disassembly gate, the disassembly event count was standardized by the number of dimers formed in the pre-dimerization. The ON/OFF level is calculated by dividing the lowest output count obtained in the TRUE condition by the highest output count obtained in the FALSE condition (when the output count in the FALSE condition is 0, the output count is set to 1).

The diffusion behavior of the nanoparticle logic gate, particularly, diffusion behavior of the floater particle, was analyzed as follows. (1) The particle density (~200 particles per total field of view) of the floater particles loaded on the SLB is sufficiently low, and thus long-term tracking is provided without orbital overlap. (2) A signal is detected from each frame, and a position of each floater particle is localized based on the same algorithm described above. (3) The determined position is used to generate a trajectory of each floater, and then used in calculation of diffusion coefficients. For each particle, the mean squared displacement (MSD) value is obtained as a function of time. The MSD plot of this trajectory is fitted to the equation $<r^2>=4Dt$, where $<r^2>$ is the MSD, D is the diffusion coefficient, and t is the time interval.

A Simulation Method of Nanoparticle Assembly Reaction for a Lipid Bilayer is as Follows.

An assembly reaction of SLB-tethered nanoparticles was modeled and simulated by using MATLAB. Such a calculation method was developed to evaluate how an NR/NF ratio affects a degree of dimer formation. In this model, given numbers of NR and NF were randomly dispersed in an area of 128×128 μm$^2$ with periodic boundary conditions. A diffusion constant of NF was specified to have a normal distribution with an average of 0.9 μm$^2$/s and a standard deviation of 0.3 μm$^2$/s. This approximation is shown in FIG. 5A and FIG. 5B, and is based on experimental data related to the diffusion profile of NF shown in FIG. 33A to FIG. 33C. The diffusion of the floater is influenced by a two-dimensional random walk, and a step size of each floater is assumed to be 4Dt when t=5 ms. The position of NR is fixed. In order to effectively perform the simulation, nanoparticles were set to be diffused at the grid point by interplanar spacing of the nanoparticle (including the length of the surface ligand). A binding event between NR and NF occurs with a probability of 0.3 for each collision. In the simulation, "collide" was defined as an event that occurred when a cross-section of a floater overlaps a cross-section of a receptor. In the formation of a multimer, it was speculated that adding another floater to a receptor-plotter dimer would be less sterically preferred than adding floater to the receptor, and thus a low binding potential (0.18 for trimer formation, 0.09 for tetramer formation) was used. The scaling factor is introduced based on the geometric constraint condition, and this simulation result is shown in FIG. 9.

An Oligonucleotide Design Method is as Follows.

Nanoparticles were functionalized with single-stranded DNA strands containing thiol modifications at the 3' end or the 5' end. The DNA sequence was designed at domain-level by using DomainDesign ("D. Y. Zhang, A. J. Turberfield, B. Yurke, E. Winfree, Engineering Entropy-Driven Reactions and Networks Catalyzed by DNA. Science. 318, 1121-1125 2007", and "D. Y. Zhang, in DNA Computing and Molecular Programming, Y. Sakakibara, Y. Mi, Eds. (Springer Berlin Heidelberg, 2010. Lecture Notes in Computer Science, pp. 162-175"), which is a free source code. The thiolated DNA strand includes (1) a biotinylated "linker" DNA strand for use in tethering a nanoparticle to a streptavidin-modified SLB surface, and (2) a "ligand" DNA strand that is directly involved in nanoparticle computation through hybridization with surface ligands of other nanoparticles on SLBs and an input DNA strand in a solution.

A linker strand having a 5'-thiol modification includes (i) a 15-based polyA domain after the 5'-thiol group, (ii) 6 ethylene glycol EG units (PEG moiety), and (iii) a 34-base linker domain followed by biotin modification A linker strand with 3'-thiol modification (with biotin modification at the 5'-end) is followed by (i) a 34-base linker domain, (ii) a PEG moiety, and (iii) 3'-thiol modification followed by a 15-based polyA domain.

A surface ligand DNA strand used in the following example is classified into the following two types: (1) a "normal" single-stranded DNA strand that does not form a hairpin loop; and (2) a hairpin-type DNA ligand used in an Assembly AND gate.

Normal ligand types are further classified into two groups: a group with 3'-thiol modification; and a group with 5'-thiol modification.

The 5'-thiol ligand includes (i) a PEG moiety (after 5'-thiol), (ii) a 10-base spacer domain, and (iii) a 14-base binding domain. The 3'-thiol ligand includes (i) a 14-base binding domain, (ii) a 10-base spacer domain, and (iii) a PEG moiety (which later included 3'-thiol modification). Unless otherwise stated, the 3'-thiol ligand and the 5'-thiol ligand were used for receptors and floaters, respectively. The hairpin-type DNA ligand was thiolated at the 5' end. In the following example, the 10-base toehold domain was used.

While this invention has been described in connection with what is presently considered to be practical exemplary embodiments, it is to be understood that the invention is not limited to the disclosed embodiments. On the contrary, it is intended to cover various modifications and equivalent arrangements included within the spirit and scope of the appended claims.

The invention claimed is:

1. A lipid nanotablet comprising:
a supported lipid bilayer to which a plurality of nanoparticles are integrated in nanoparticle units;
an immobile nano-receptor that includes at least one first surface molecule tethered to a surface and is immobile among the plurality of nanoparticles; and
a nano-floater that includes at least one second surface molecule tethered to a surface and is mobile among the plurality of nanoparticles,
wherein a logic result based on at least one interaction is provided, and
wherein the at least one interaction comprises at least one of
an assembly reaction in which the at least one first surface molecule and the at least one second surface molecule are combined by a first input,
a disassembly reaction that removes the tethering between the nano-receptor and the nano-floater by a second input,
tethering of the nano-receptor and the nano-floater by combinations of a third input to the at least one first surface molecule and a fourth input to the at least one second surface molecule, and
removing a combination between the at least one first surface molecule and the at least one second surface molecule by at least one of a fifth input and a sixth input.

2. The lipid nanotablet of claim 1, wherein the first input comprises a DNA input, and the at least one first surface molecule and the at least second surface molecule respectively comprise surface DNA ligands, and
the lipid nanotablet further comprises a YES gate that generates a logic result based on the assembly reaction in which the surface DNA ligand of the nano-receptor and the surface DNA ligand of the nano-floater are hybridized in response to the DNA input.

3. The lipid nanotablet of claim 1, wherein the second input comprises a DNA input, and
the lipid nanotablet further comprises a YES gate that generates a logic result based on the disassembly reaction where the DNA input removes a DNA bond through a toehold-mediated strand displacement in pre-dimerization of the nano-receptor and the nano-floater tethered through the DNA bond.

4. The lipid nanotablet of claim 1, wherein the at least one first surface molecule and the at least one second surface molecule comprise conformation-switchable first and second DNA hairpins, and
the lipid nanotablet further comprises an AND gate that generates a logic result based on tethering in which the first DNA hairpin is opened by hybridization with the third input and thus a first binding domain is exposed, the second DNA hairpin is opened by hybridization with the fourth input and thus a second binding domain is exposed, and the nano-receptor and the nano-floater are tethered through hybridization of the first binding domain and the second binding domain.

5. The lipid nanotablet of claim 1, wherein the at least one first surface molecule comprises third and fourth surface molecules,
the at least one second surface molecule comprises fifth and sixth surface molecules, and
the lipid nanotablet further comprises an OR gate that generates a logic result from tethering of the nano-receptor and the nano-floater by at least one of a combination of the third input and the third and fifth surface molecules and a combination of the fourth input and the fourth and sixth surface molecules.

6. The lipid nanotablet of claim 5, wherein the third to sixth surface molecules are DNA ligands, and comprise first to fourth binding domains, and
the third input is hybridized with the first and third binding domains and the fourth input is hybridized with the second and fourth binding domains.

7. The lipid nanotablet of claim 1,
wherein the at least one first surface molecule comprises third and fourth surface molecules,
the at least one second surface molecule comprises fifth and sixth surface molecules,
the third surface molecule and the fifth surface molecule are combined, the fourth surface molecule and the sixth surface molecule are combined, and
the lipid nanotablet comprises an AND gate that generates a logic result by removing the combination of the third and fifth surface molecules by the fifth input and removing the combination of the fourth and sixth surface molecules by the sixth input.

8. The lipid nanotablet of claim 7, wherein first DNA binding between the third surface molecule and the fifth surface molecule and second DNA binding between the fourth surface molecule and the sixth surface molecule expose a first toehold domain and a second toehold domain,
the first toehold domain is a recognition area of the fifth input, the fifth input removes the first DNA binding through strand displacement, the second toehold domain is a recognition area of the sixth input, and the sixth input removes the second DNA binding through strand displacement.

9. The lipid nanotablet of claim 1, wherein the at least one first surface molecule and the at least one second surface molecule are combined, and
the lipid nanotablet comprises an OR gate that generates a logic result by removing the at least one first surface molecule and the at least one second surface molecule by at least one of the fifth input and the sixth input.

10. The lipid nanotablet of claim 9, wherein the combination of the at least one first surface molecule and the at least one second surface molecule is DNA binding, the DNA binding comprises first and second toehold domains,
when the first toehold recruits the fifth input, the fifth input cleaves the DNA bonding through strand displacement with at least one first surface molecule, or
when the second toehold domain recruits the sixth input, the sixth input cleaves the DNA binding through strand displacement with the at least one second surface molecule.

11. The lipid nanotablet of claim 1, wherein interaction between the nano-receptor and the nano-floater is a first logic gate that is controlled by a seventh input and an eighth input,
interaction between another one first nano-receptor and another one first nano -floater among the plurality of nanoparticles is a second logic gate that is controlled by a ninth input and a tenth input, and
the lipid nanotablet comprises a third logic gate that generates a logic result based on a first logic result of the first logic gate and a second logic result of the second logic gate.

12. The lipid nanotablet of claim 11, wherein the nano-receptor and the nano-floater are tethered by at least one of the seventh input and the eighth input,
the tethering of the first nano-receptor and the first nano-floater is disassembled by the ninth input and the tenth input, and
the first logic output is a logic OFF output of the third logic gate and the second logic output is a logic ON output of the third logic gate.

13. The lipid nanotablet of claim 1, wherein the at least one first surface molecule comprises third and fourth surface molecules,
the at least one second surface molecule comprises fifth and sixth surface molecules, and
the lipid nanotablet comprises an INHIBIT gate that generates a logic result by removing the combination between the third surface molecule and the fifth surface molecule by the fifth input.

14. The lipid nanotablet of claim 1, wherein interaction of the nano -receptor and the nano-floater is controlled as third and fourth surface molecules tethered to the at least one first surface molecule and the surface of the nano-receptor and fifth and sixth surface molecules tethered to the at least one second surface molecule and the surface of the nano-floater interact with each other.

15. The lipid nanotablet of claim 1, wherein a first interaction between the nano-receptor and the nano-floater is controlled by a seventh input and an eighth input,
among the plurality of nanoparticles, a second interaction between another one first nano-receptor and another one first nano-floater is controlled by a ninth input and a tenth input, and
the seventh input and the ninth input are of the same type and the eighth input and the tenth input are of the same type.

16. A lipid nanotablet in a supported lipid bilayer to which a plurality of nanoparticles are integrated in nanoparticle units, comprising:
a first nano-receptor;
a second nano-receptor;
a first nano-floater that interacts according to at least one input for the first nano -receptor; and
a second nano-floater that interacts according to a first input for the second nano -receptor,
wherein wiring between a first logic gate including the first nano-receptor and a second logic gate including the second nano-receptor is determined based on the first nano-floater and the second nano-floater.

17. The lipid nanotablet of claim 16, wherein the first nano-floater and the second nano-floater are of the same type, and
the first logic gate and the second logic gate are AND wired.

18. The lipid nanotablet of claim 16, wherein the first nano-floater and the second nano-floater are of different types, and
the first logic gate and the second logic gate are OR wired.

19. A lipid nanotablet in a supported lipid bilayer to which a plurality of nanoparticles are integrated in nanoparticle units, comprising:
- a first logic gate configured to interact a first nano-receptor and a first nano-floater with each other according to a selected input and a first input; and
- a second logic gate configured to interact a second nano-receptor and a second nano-floater with each other according to the selected input and a second input,
- wherein one of the first logic gate and the second logic gate is configured to release a nano-floater that corresponds according to a corresponding input among the first input and the second input according to the selected input.

20. A nanobio computing method in a supported lipid bilayer to which a plurality of nanoparticles are integrated in nanoparticle units, comprising:
- generating a plurality of interactions between a plurality of immobile nano-receptors in the lipid bilayer and a plurality of mobile nano-floaters in the lipid bilayer according to inputs;
- generating a plurality of signals based on the plurality of interactions;
- tracking signals generated only from the plurality of nano-receptors among the plurality of signals; and
- determining a logic result based on the tracking result wherein the tracking comprises:
- detecting a signal higher than a detection parameter in generated image data by dark-field microscopy;
- generating a segmented signal by distinguishing a boundary of the detected signal:
- providing positions of nanoparticles by localizing a center of the segmented signal:
- identifying a nano-receptor by comparing the positions of the nanoparticles through a plurality of frames; and
- sampling a signal corresponding to the identified nano-receptor.

* * * * *

SEQUENCE LISTING

```
<160> NUMBER OF SEQ ID NOS: 61

<210> SEQ ID NO 1
<211> LENGTH: 24
<212> TYPE: DNA
<213> ORGANISM: Artificial Sequence
<220> FEATURE:
<223> OTHER INFORMATION: Synthetic

<400> SEQUENCE: 1
ctataaacta tttcctttgc tatt                                            24

<210> SEQ ID NO 2
<211> LENGTH: 24
<212> TYPE: DNA
<213> ORGANISM: Artificial Sequence
<220> FEATURE:
<223> OTHER INFORMATION: Synthetic

<400> SEQUENCE: 2
cgcaaagaca ctaataacaa attc                                            24

<210> SEQ ID NO 3
<211> LENGTH: 50
<212> TYPE: DNA
<213> ORGANISM: Artificial Sequence
<220> FEATURE:
<223> OTHER INFORMATION: Synthetic

<400> SEQUENCE: 3
acttcacaaa gtgtacttgt agattccaaa tctactacaa gtacactttg                50

<210> SEQ ID NO 4
<211> LENGTH: 50
<212> TYPE: DNA
<213> ORGANISM: Artificial Sequence
<220> FEATURE:
<223> OTHER INFORMATION: Synthetic

<400> SEQUENCE: 4
cttctaaagt acactttgta ggatttccaa ctaacctaca aagtgtactt                50

<210> SEQ ID NO 5
<211> LENGTH: 34
<212> TYPE: DNA
<213> ORGANISM: Artificial Sequence
<220> FEATURE:
<223> OTHER INFORMATION: Synthetic
```

```
<400> SEQUENCE: 5
ttactacact gtcactgatc atcgcatgct atac                              34

<210> SEQ ID NO 6
<211> LENGTH: 24
<212> TYPE: DNA
<213> ORGANISM: Artificial Sequence
<220> FEATURE:
<223> OTHER INFORMATION: Synthetic

<400> SEQUENCE: 6
caaataacta atacacattc atct                                         24

<210> SEQ ID NO 7
<211> LENGTH: 24
<212> TYPE: DNA
<213> ORGANISM: Artificial Sequence
<220> FEATURE:
<223> OTHER INFORMATION: Synthetic

<400> SEQUENCE: 7
cataatctat aatcatcctc ataa                                         24

<210> SEQ ID NO 8
<211> LENGTH: 24
<212> TYPE: DNA
<213> ORGANISM: Artificial Sequence
<220> FEATURE:
<223> OTHER INFORMATION: Synthetic

<400> SEQUENCE: 8
tactcactat ctaaaaacaa ttac                                         24

<210> SEQ ID NO 9
<211> LENGTH: 24
<212> TYPE: DNA
<213> ORGANISM: Artificial Sequence
<220> FEATURE:
<223> OTHER INFORMATION: Synthetic

<400> SEQUENCE: 9
cttagcctaa cattttctaa atac                                         24

<210> SEQ ID NO 10
<211> LENGTH: 24
<212> TYPE: DNA
<213> ORGANISM: Artificial Sequence
<220> FEATURE:
<223> OTHER INFORMATION: Synthetic

<400> SEQUENCE: 10
caaataacta atacacattc atct                                         24

<210> SEQ ID NO 11
<211> LENGTH: 24
<212> TYPE: DNA
<213> ORGANISM: Artificial Sequence
<220> FEATURE:
<223> OTHER INFORMATION: Synthetic

<400> SEQUENCE: 11
cgcaaagaca ctaataacaa attc                                         24

<210> SEQ ID NO 12
<211> LENGTH: 24
```

```
<212> TYPE: DNA
<213> ORGANISM: Artificial Sequence
<220> FEATURE:
<223> OTHER INFORMATION: Synthetic

<400> SEQUENCE: 12
cttagcctaa cattttctaa atac                                              24

<210> SEQ ID NO 13
<211> LENGTH: 24
<212> TYPE: DNA
<213> ORGANISM: Artificial Sequence
<220> FEATURE:
<223> OTHER INFORMATION: Synthetic

<400> SEQUENCE: 13
cattatcata taactcaacg tcac                                              24

<210> SEQ ID NO 14
<211> LENGTH: 24
<212> TYPE: DNA
<213> ORGANISM: Artificial Sequence
<220> FEATURE:
<223> OTHER INFORMATION: Synthetic

<400> SEQUENCE: 14
aatcagcatc ctattacata attc                                              24

<210> SEQ ID NO 15
<211> LENGTH: 24
<212> TYPE: DNA
<213> ORGANISM: Artificial Sequence
<220> FEATURE:
<223> OTHER INFORMATION: Synthetic

<400> SEQUENCE: 15
ctgcacatta gtattagtta tttg                                              24

<210> SEQ ID NO 16
<211> LENGTH: 24
<212> TYPE: DNA
<213> ORGANISM: Artificial Sequence
<220> FEATURE:
<223> OTHER INFORMATION: Synthetic

<400> SEQUENCE: 16
gtaattgttt ttagtattct tctc                                              24

<210> SEQ ID NO 17
<211> LENGTH: 24
<212> TYPE: DNA
<213> ORGANISM: Artificial Sequence
<220> FEATURE:
<223> OTHER INFORMATION: Synthetic

<400> SEQUENCE: 17
cataatctat aatcatcctc ataa                                              24

<210> SEQ ID NO 18
<211> LENGTH: 50
<212> TYPE: DNA
<213> ORGANISM: Artificial Sequence
<220> FEATURE:
<223> OTHER INFORMATION: Synthetic

<400> SEQUENCE: 18
```

```
cttctaaagt acactttgta ggatttccaa ctaacctaca aagtgtactt          50

<210> SEQ ID NO 19
<211> LENGTH: 50
<212> TYPE: DNA
<213> ORGANISM: Artificial Sequence
<220> FEATURE:
<223> OTHER INFORMATION: Synthetic

<400> SEQUENCE: 19
cttctaaagt acactttgta ggatttccaa ctaacctaca aagtgtactt          50

<210> SEQ ID NO 20
<211> LENGTH: 24
<212> TYPE: DNA
<213> ORGANISM: Artificial Sequence
<220> FEATURE:
<223> OTHER INFORMATION: Synthetic

<400> SEQUENCE: 20
cattatcata taactcaacg tcac                                     24

<210> SEQ ID NO 21
<211> LENGTH: 24
<212> TYPE: DNA
<213> ORGANISM: Artificial Sequence
<220> FEATURE:
<223> OTHER INFORMATION: Synthetic

<400> SEQUENCE: 21
aatcagcatc ctattacata attc                                     24

<210> SEQ ID NO 22
<211> LENGTH: 24
<212> TYPE: DNA
<213> ORGANISM: Artificial Sequence
<220> FEATURE:
<223> OTHER INFORMATION: Synthetic

<400> SEQUENCE: 22
cgcaaagaca ctaataacaa attc                                     24

<210> SEQ ID NO 23
<211> LENGTH: 24
<212> TYPE: DNA
<213> ORGANISM: Artificial Sequence
<220> FEATURE:
<223> OTHER INFORMATION: Synthetic

<400> SEQUENCE: 23
cattatcata taactcaacg tcac                                     24

<210> SEQ ID NO 24
<211> LENGTH: 24
<212> TYPE: DNA
<213> ORGANISM: Artificial Sequence
<220> FEATURE:
<223> OTHER INFORMATION: Synthetic

<400> SEQUENCE: 24
aatcagcatc ctattacata attc                                     24

<210> SEQ ID NO 25
<211> LENGTH: 34
<212> TYPE: DNA
<213> ORGANISM: Artificial Sequence
```

```
<220> FEATURE:
<223> OTHER INFORMATION: Synthetic

<400> SEQUENCE: 25
ctctctgcct cgttcagaca aaactcatcc tact                                34

<210> SEQ ID NO 26
<211> LENGTH: 34
<212> TYPE: DNA
<213> ORGANISM: Artificial Sequence
<220> FEATURE:
<223> OTHER INFORMATION: Synthetic

<400> SEQUENCE: 26
ttactacact gtcactgatc atcgcatgct atac                                34

<210> SEQ ID NO 27
<211> LENGTH: 34
<212> TYPE: DNA
<213> ORGANISM: Artificial Sequence
<220> FEATURE:
<223> OTHER INFORMATION: Synthetic

<400> SEQUENCE: 27
ctctctgcct cgttcagaca aaactcatcc tact                                34

<210> SEQ ID NO 28
<211> LENGTH: 34
<212> TYPE: DNA
<213> ORGANISM: Artificial Sequence
<220> FEATURE:
<223> OTHER INFORMATION: Synthetic

<400> SEQUENCE: 28
ttactacact gtcactgatc atcgcatgct atac                                34

<210> SEQ ID NO 29
<211> LENGTH: 34
<212> TYPE: DNA
<213> ORGANISM: Artificial Sequence
<220> FEATURE:
<223> OTHER INFORMATION: Synthetic

<400> SEQUENCE: 29
ctctctgcct cgttcagaca aaactcatcc tact                                34

<210> SEQ ID NO 30
<211> LENGTH: 34
<212> TYPE: DNA
<213> ORGANISM: Artificial Sequence
<220> FEATURE:
<223> OTHER INFORMATION: Synthetic

<400> SEQUENCE: 30
ttactacact gtcactgatc atcgcatgct atac                                34

<210> SEQ ID NO 31
<211> LENGTH: 34
<212> TYPE: DNA
<213> ORGANISM: Artificial Sequence
<220> FEATURE:
<223> OTHER INFORMATION: Synthetic

<400> SEQUENCE: 31
ttactacact gtcactgatc atcgcatgct atac                                34
```

<210> SEQ ID NO 32
<211> LENGTH: 34
<212> TYPE: DNA
<213> ORGANISM: Artificial Sequence
<220> FEATURE:
<223> OTHER INFORMATION: Synthetic

<400> SEQUENCE: 32
ttactacact gtcactgatc atcgcatgct atac                              34

<210> SEQ ID NO 33
<211> LENGTH: 38
<212> TYPE: DNA
<213> ORGANISM: Artificial Sequence
<220> FEATURE:
<223> OTHER INFORMATION: Synthetic

<400> SEQUENCE: 33
gaaatagttt atagctgcga ctgtgaattt gttattag                          38

<210> SEQ ID NO 34
<211> LENGTH: 38
<212> TYPE: DNA
<213> ORGANISM: Artificial Sequence
<220> FEATURE:
<223> OTHER INFORMATION: Synthetic

<400> SEQUENCE: 34
ctaataacaa attcacagtc gcagctataa actatttc                          38

<210> SEQ ID NO 35
<211> LENGTH: 23
<212> TYPE: DNA
<213> ORGANISM: Artificial Sequence
<220> FEATURE:
<223> OTHER INFORMATION: Synthetic

<400> SEQUENCE: 35
agttggaaat cctacaaagt gta                                          23

<210> SEQ ID NO 36
<211> LENGTH: 23
<212> TYPE: DNA
<213> ORGANISM: Artificial Sequence
<220> FEATURE:
<223> OTHER INFORMATION: Synthetic

<400> SEQUENCE: 36
gatttggaat ctacaagtac act                                          23

<210> SEQ ID NO 37
<211> LENGTH: 38
<212> TYPE: DNA
<213> ORGANISM: Artificial Sequence
<220> FEATURE:
<223> OTHER INFORMATION: Synthetic

<400> SEQUENCE: 37
gtattagtta tttgtagacg tagggtaatt gttttag                           38

<210> SEQ ID NO 38
<211> LENGTH: 38
<212> TYPE: DNA
<213> ORGANISM: Artificial Sequence
<220> FEATURE:
<223> OTHER INFORMATION: Synthetic

<400> SEQUENCE: 38
gattatagat tatgtgttag ctgtgtattt agaaaatg					38

<210> SEQ ID NO 39
<211> LENGTH: 38
<212> TYPE: DNA
<213> ORGANISM: Artificial Sequence
<220> FEATURE:
<223> OTHER INFORMATION: Synthetic

<400> SEQUENCE: 39
ctaaaaacaa ttaccctacg tctacaaata actaatac					38

<210> SEQ ID NO 40
<211> LENGTH: 38
<212> TYPE: DNA
<213> ORGANISM: Artificial Sequence
<220> FEATURE:
<223> OTHER INFORMATION: Synthetic

<400> SEQUENCE: 40
gtattagtta tttgtagacg tagggtaatt gtttttag					38

<210> SEQ ID NO 41
<211> LENGTH: 38
<212> TYPE: DNA
<213> ORGANISM: Artificial Sequence
<220> FEATURE:
<223> OTHER INFORMATION: Synthetic

<400> SEQUENCE: 41
cattttctaa atacacagct aacacataat ctataatc					38

<210> SEQ ID NO 42
<211> LENGTH: 24
<212> TYPE: DNA
<213> ORGANISM: Artificial Sequence
<220> FEATURE:
<223> OTHER INFORMATION: Synthetic

<400> SEQUENCE: 42
ctaataacaa attcctcacg aact					24

<210> SEQ ID NO 43
<211> LENGTH: 24
<212> TYPE: DNA
<213> ORGANISM: Artificial Sequence
<220> FEATURE:
<223> OTHER INFORMATION: Synthetic

<400> SEQUENCE: 43
acagtcgcag ctataaacta tttc					24

<210> SEQ ID NO 44
<211> LENGTH: 48
<212> TYPE: DNA
<213> ORGANISM: Artificial Sequence
<220> FEATURE:
<223> OTHER INFORMATION: Synthetic

<400> SEQUENCE: 44
gaaatagttt atagctgcga ctgtagttcg tgaggaattt gttattag					48

<210> SEQ ID NO 45

```
<211> LENGTH: 38
<212> TYPE: DNA
<213> ORGANISM: Artificial Sequence
<220> FEATURE:
<223> OTHER INFORMATION: Synthetic

<400> SEQUENCE: 45
ctaaaaacaa ttaccctacg tctacaaata actaatac                              38

<210> SEQ ID NO 46
<211> LENGTH: 38
<212> TYPE: DNA
<213> ORGANISM: Artificial Sequence
<220> FEATURE:
<223> OTHER INFORMATION: Synthetic

<400> SEQUENCE: 46
gattatagat tatgtgttag ctgtgtattt agaaaatg                              38

<210> SEQ ID NO 47
<211> LENGTH: 48
<212> TYPE: DNA
<213> ORGANISM: Artificial Sequence
<220> FEATURE:
<223> OTHER INFORMATION: Synthetic

<400> SEQUENCE: 47
gaaatagttt atagctgcga ctgtagttcg tgaggaattt gttattag                   48

<210> SEQ ID NO 48
<211> LENGTH: 24
<212> TYPE: DNA
<213> ORGANISM: Artificial Sequence
<220> FEATURE:
<223> OTHER INFORMATION: Synthetic

<400> SEQUENCE: 48
ctaaaaacaa ttaccctacg tcta                                             24

<210> SEQ ID NO 49
<211> LENGTH: 24
<212> TYPE: DNA
<213> ORGANISM: Artificial Sequence
<220> FEATURE:
<223> OTHER INFORMATION: Synthetic

<400> SEQUENCE: 49
aatacacttc caaataacta atac                                             24

<210> SEQ ID NO 50
<211> LENGTH: 48
<212> TYPE: DNA
<213> ORGANISM: Artificial Sequence
<220> FEATURE:
<223> OTHER INFORMATION: Synthetic

<400> SEQUENCE: 50
gtattagtta tttggaagtg tatttagacg tagggtaatt gtttttag                   48

<210> SEQ ID NO 51
<211> LENGTH: 24
<212> TYPE: DNA
<213> ORGANISM: Artificial Sequence
<220> FEATURE:
<223> OTHER INFORMATION: Synthetic

<400> SEQUENCE: 51
```

```
cattttctaa atacacagct aaca                                          24

<210> SEQ ID NO 52
<211> LENGTH: 24
<212> TYPE: DNA
<213> ORGANISM: Artificial Sequence
<220> FEATURE:
<223> OTHER INFORMATION: Synthetic

<400> SEQUENCE: 52
acagatccca cataatctat aatc                                          24

<210> SEQ ID NO 53
<211> LENGTH: 48
<212> TYPE: DNA
<213> ORGANISM: Artificial Sequence
<220> FEATURE:
<223> OTHER INFORMATION: Synthetic

<400> SEQUENCE: 53
gattatagat tatgtgggat ctgttgttag ctgtgtattt agaaaatg                48

<210> SEQ ID NO 54
<211> LENGTH: 38
<212> TYPE: DNA
<213> ORGANISM: Artificial Sequence
<220> FEATURE:
<223> OTHER INFORMATION: Synthetic

<400> SEQUENCE: 54
cattttctaa atacacagct aacacataat ctataatc                           38

<210> SEQ ID NO 55
<211> LENGTH: 38
<212> TYPE: DNA
<213> ORGANISM: Artificial Sequence
<220> FEATURE:
<223> OTHER INFORMATION: Synthetic

<400> SEQUENCE: 55
ctattacata attctgcatt cttccattat catataac                           38

<210> SEQ ID NO 56
<211> LENGTH: 38
<212> TYPE: DNA
<213> ORGANISM: Artificial Sequence
<220> FEATURE:
<223> OTHER INFORMATION: Synthetic

<400> SEQUENCE: 56
gttatatgat aatggaagaa tgcagaatta tgtaatag                           38

<210> SEQ ID NO 57
<211> LENGTH: 48
<212> TYPE: DNA
<213> ORGANISM: Artificial Sequence
<220> FEATURE:
<223> OTHER INFORMATION: Synthetic

<400> SEQUENCE: 57
tactcactat ctaaaaacaa ttaccctacg tctacaaata actaatac                48

<210> SEQ ID NO 58
<211> LENGTH: 14
<212> TYPE: DNA
```

```
<213> ORGANISM: Artificial Sequence
<220> FEATURE:
<223> OTHER INFORMATION: Synthetic

<400> SEQUENCE: 58
gtaattgttt ttag                                                         14

<210> SEQ ID NO 59
<211> LENGTH: 23
<212> TYPE: DNA
<213> ORGANISM: Artificial Sequence
<220> FEATURE:
<223> OTHER INFORMATION: Synthetic

<400> SEQUENCE: 59
agttggaaat cctacaaagt gta                                               23

<210> SEQ ID NO 60
<211> LENGTH: 23
<212> TYPE: DNA
<213> ORGANISM: Artificial Sequence
<220> FEATURE:
<223> OTHER INFORMATION: Synthetic

<400> SEQUENCE: 60
gatttggaat ctacaagtac act                                               23

<210> SEQ ID NO 61
<211> LENGTH: 38
<212> TYPE: DNA
<213> ORGANISM: Artificial Sequence
<220> FEATURE:
<223> OTHER INFORMATION: Synthetic

<400> SEQUENCE: 61
gattatagat tatgtgttag ctgtgtattt agaaaatg                               38
```